United States Patent
Payne et al.

(10) Patent No.: US 10,233,148 B2
(45) Date of Patent: Mar. 19, 2019

(54) AROMATIC IONIZABLE CATIONIC LIPID

(71) Applicant: Arcturus Therapeutics, Inc., San Diego, CA (US)

(72) Inventors: Joseph E. Payne, San Diego, CA (US); Padmanabh Chivukula, San Diego, CA (US); Steven P. Tanis, Carlsbad, CA (US)

(73) Assignee: Arcturus Therapeutics, Inc., San Diego, CA (US)

( * ) Notice: Subject to any disclaimer, the term of this patent is extended or adjusted under 35 U.S.C. 154(b) by 0 days.

(21) Appl. No.: 15/799,098

(22) Filed: Oct. 31, 2017

(65) Prior Publication Data

US 2018/0050987 A1 Feb. 22, 2018

Related U.S. Application Data

(63) Continuation of application No. 15/393,840, filed on Dec. 29, 2016, now Pat. No. 9,834,510.

(60) Provisional application No. 62/273,212, filed on Dec. 30, 2015.

(51) Int. Cl.
*C07C 333/04* (2006.01)
*C07C 271/22* (2006.01)

(52) U.S. Cl.
CPC .......... *C07C 333/04* (2013.01); *C07C 271/22* (2013.01)

(58) Field of Classification Search
CPC .................. C07C 333/04; C07C 271/22
See application file for complete search history.

(56) References Cited

U.S. PATENT DOCUMENTS

| | | | |
|---|---|---|---|
| 9,308,267 B2 | 4/2016 | Payne et al. | |
| 9,365,610 B2 | 6/2016 | Payne et al. | |
| 9,567,296 B2 | 2/2017 | Payne et al. | |
| 9,593,077 B2 | 3/2017 | Payne et al. | |
| 9,670,152 B2 | 6/2017 | Payne et al. | |
| 9,834,510 B2 * | 12/2017 | Payne | C07C 271/22 |
| 9,850,202 B2 * | 12/2017 | Payne | C07C 323/52 |
| 9,896,413 B2 * | 2/2018 | Payne | C07C 323/25 |
| 2014/0308304 A1 | 10/2014 | Manoharan et al. | |
| 2015/0239926 A1 | 8/2015 | Payne et al. | |

FOREIGN PATENT DOCUMENTS

WO     WO 2015/074085 A1     5/2015

OTHER PUBLICATIONS

International Patent Application No. PCT/US2016/069493; Int'l Search Report and the Written Opinion; dated Mar. 22, 2017; 14 pages.

Sase et al.; "One-Pot Negishi Cross-Coupling Reactions of in Situ Zinc Reagents with Aryl Chlorides, Bromides, and Triflates"; J. Org. Chem.; vol. 73 No. 18; 2008; p. 7380-7382.

Nodes et al.; "Enantioselective Intramolecular Michael Addition of Nitronates onto Conjugates Esters: Access to Cyclic y-Amino Acids with up to Three Stereocentres"; American Chemical Society; 2009; 89 pages.

Nodes et al.; "Enantioselective Intramolecular Michael Addition of Nitronates onto Conjugates Esters: Access to Cyclic y-Amino Acids with up to Three Stereocenters"; J. Am. Chem. Soc.; vol. 131; 2009; p. 16016-16017.

Taylor et al.; "A New and Efficient Synthesis of Pyrrolo [2,3-d]pyrimidine Anticancer Agents: Alimta (LY231514, MTA), Homo-Alimta, TNP-351, and Some Aryl 5-Substituted Pyrrolo[2,3-d]pyrimidines"; J. Org. Chem.; vol. 68, 2003; p. 9938-9947.

Taylor et al.; "A Convergent Synthesis of 5,10-Dideaza-5,6,7,8-tetrahydrofolic Acid and 5,10-Dideaza-5,6,7,8-tetrahydrohomfolic Acid. An Effective Principle for Carbonyl Group Activation"; J. Org. Chem.; vol. 55; 1990; p. 3222-3227.

Medran-Navarrete et al.; "Preparation and evaluation of novel pyrazolo[1,5-a]pyrimidine acetamides, closely related to DPA-714, as potent ligands for imaging the TSPO 18 kDa with PET"; Bioorganic & Medicinal Chemistry Letters; vol. 24; 2014; p. 1550-1556.

Fischer et al.; "Umpolung of Michael Acceptors Catalyzed by N-Heterocyclic Carbenes"; J. Am. Chem. Soc.; vol. 128; 2006; p. 1472-1473.

Gericke et al.; "The versatile role of norbornene in C—H functionalization processes: concise synthesis of tetracyclic fused pyrroles via a threefold domino reaction"; Tetrahedron; vol. 64; 2008; p. 6002-6014.

Enders et al.; "Diastereo- and Enantioselective Synthesis of 1,2-trans-substituted Cycloalkanecarboxylates and Sulfones by Michael Initiated Cyclisation via SAMP / RAMP Hydrazones"; Chem. Ber.; vol. 126; 1993; p. 1929-1944 (contains English Abstract).

(Continued)

*Primary Examiner* — Golam M Shameem
(74) *Attorney, Agent, or Firm* — Baker & Hostetler LLP

(57) ABSTRACT

What is described is a compound of formula I

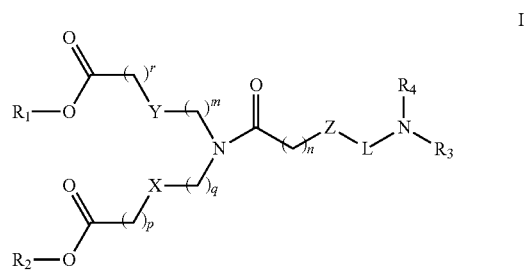

wherein
X is an alkylene or an alkenylene;
Y is a monocyclic, bicyclic, or tricyclic arene or heteroarene;
Z is S or O;
L is a linear or branched alkylene of 1 to 6 carbons;
$R_1$ is a branched alkyl or alkenyl of 1 to 25 carbons;
$R_2$ is a alkyl or alkenyl of 1 to 20 carbons;
$R_3$ and $R_4$ are independently a linear or branched alkyl of 1 to 6 carbons;
n is 0 to 6; and
m, p, q, and r are independently 1-18;
or a pharmaceutically acceptable salt thereof.

20 Claims, 9 Drawing Sheets

(56) References Cited

OTHER PUBLICATIONS

Passarella et al.; "Histone deacetylase and microtubes as targets for the synthesis of releasable conjugate compounds"; Bioorganic & Medicinal Chemistry Letters; vol. 19; 2009; p. 6358-6363.
Passarella et al.; "Histone deacetylase and microtubes as targets for the synthesis of releasable conjugate compounds"; Bioorganic & Medicinal Chemistry Letters; 2009 Supplementary Material; 16 pages.
Fushimi et al.; "Design, synthesis, and structure-activity relationships of a series of 4-benzyl-5-isopropyl-1H-pyrazol-3-yl b-D-glycopyranosides substituted with novel hydrophilic groups as highly potent inhibitors of sodium glucose co-transporter 1 (SGLT1)"; Bioorganic & Medicinal Chemistry; vol. 21; 2013; p. 748-765.
Koley et al.; "Organocatalytic Asymmetric Mannich Cyclization of Hydroxylactams with Acetals: Total Syntheses of (−)-Epilupininie, (−)-Tashiromine, and (−)-Trachelanthamidine"; Angew. Chem. Int. Ed.; vol. 53; 2014; p. 13196-13200.
Koley et al.; "Organocatalytic Asymmetric Mannich Cyclization of Hydroxylactams with Acetals: Total Syntheses of (−)-Epilupininie, (−)-Tashiromine, and (−)-Trachelanthamidine"; Angew. Chem. Int. Ed.; 2014; Supporting Information; 110 pages.
Jamison et al.; "Syntheses and Antifungal Activity of Pseudomycin Side-Chain Analogues. Part 1"; Bioorganic & Medicinal Chemistry Letters; vol. 10; 2000; p. 2101-2105.
Collington et al.; "A Facile and Specific Conversion of Allylic Alcohols to Allylic Chlorides without Rearrangement"; J. Org. Chem.; vol. 36 No. 20; 1971; p. 3044-3045.
Guan et al.; "Catalytic Asymmetric Synthesis of Alkynyl Aziridines: Both Enantiomers of cis-Aziridines from One Enantiomer of the Catalyst"; Chem. Eur. J.; vol. 20; 2014; p. 13894-13900.
Christiansen et al.; "Structure-Activity Study of Dihydrocinnamic Acids and Discovery of the Potent FFA1 (GPR40) Agonist TUG-469"; ACS Med. Chem. Letter; vol. 1; 2010; p. 345-349.
Christiansen et al.; "Structure-Activity Study of Dihydrocinnamic Acids and Discovery of the Potent FFA1 (GPR40) Agonist TUG-469"; ACS Med. Chem. Letter; 2010; Supporting Information; 27 pages.
Dvorak et al.; "Diamine-based human histamine H3 receptor antagonists: (4-Aminobutyn-1-yl)benzylamines"; European Journal of Medicinal Chemistry; vol. 44; 2009; p. 4098-4106.
Kirkman et al.; "Synthesis of 3-(carboxyarylalkyl)imidazo[2,1-f][1,2,4]triazines as potential inhibitors of AMP deaminase"; Org. Biomol. Chem.; vol. 6; 2008; p. 4452-4459.
Radeke et al.; "Synthesis and Biological Evaulation of the Mitochondrial Complex 1 Inhibitor 2-[4-(4-Fluorobutyl)benzylsulfanyl]-3-methylchromene-4-one as a Potential Cardiac Positron Emission Tomography Tracer"; J. Med. Chem.; vol. 50 2007; p. 4304-4315.
Gossett et al.; "Synthesis and Biological Evaluation of a New Series of Dihydrofolate Reductase Inhibitors Based on the 4-(2,6-Diamino-5-Pyrimidinyl)Alkyl-L-Glutamic Acid Structure"; Bioorganic & Medicinal Chemistry Letters; vol. 6 No. 4; 1996; p. 473-476.
Khanapure et al.; "An Efficient Approach to the synthesis of LTB4 and w-substituted LTB4 Metabolites"; Tetrahedron Letters; vol. 43; 2002; p. 6063-6066.
Tilley et al.; "Tyrosine-Selective Protein Alkylation Usine .pi.-Allylpalladium Complexes"; J. Am. Chem. Soc.; vol. 128 No. 4; 2006; p. 1080-1081.
Tilley et al.; "Tyrosine-Selective Protein Alkylation Usine .pi.-Allylpalladium Complexes"; J. Am. Chem. Soc.; 2006; Supporting Information; 8 pages.
Tellitu et al.; "Intramolecular PIFA-Mediated Alkyne Amidation and Carboxylation Reaction"; J. Org. Chem.; vol. 72; 2007; p. 1526-1529.
Tellitu et al.; "Intramolecular PIFA-Mediated Alkyne Amidation and Carboxylation Reaction"; J. Org. Chem.; 2007; Supporting Information; 25 pages.
Bellina et al.; "Reaction of Alkynes with Iodine Monochloride Revisited"; J. Org. Chem.; vol. 68; 2003; p. 10175-10177.
Bellina et al.; "Reaction of Alkynes with Iodine Monochloride Revisited"; J. Org. Chem.; 2003; Supporting Information; 9 pages.
Long et al.; "Metathesis Depolymerization for Removable Surfactant Templates"; Langmuir; vol. 21 No. 20, 2005; p. 9365-9373.
International Patent Application No. PCT/US2016/069493; Int'l Preliminary Report on Patentability; dated Jul. 12, 2018; 9 pages.

\* cited by examiner

AROMATIC IONIZABLE CATIONIC LIPID

CROSS REFERENCE TO RELATED APPLICATIONS

This application is a continuation of U.S. patent application Ser. No. 15/393,840, filed Dec. 29, 2016, now U.S. Pat. No. 9,834,510, issued Dec. 5, 2017, which claims benefit under 35 U.S.C. § 119(e) of Provisional U.S. Patent Application 62/273,212, filed Dec. 30, 2015, the contents of which are incorporated herein by reference in their entirety.

BACKGROUND

A number of different types of nucleic acids are currently being developed as therapeutics for the treatment of a number of diseases. These nucleic acids include DNA in gene therapy, plasmids-based interfering nucleic acids, small interfering nucleic acids for use in RNA interference (RNAi), including siRNA, miRNA, antisense molecules, ribozymes and aptamers. As these molecules are being developed, there has been developed a need to produce them in a form that is stable and has a long shelf-life and that can be easily incorporated into an anhydrous organic or anhydrous polar aprotic solvent to enable encapsulations of the nucleic acids without the side-reactions that can occur in a polar aqueous solution or nonpolar solvents.

The delivery of a therapeutic compound to a subject is important for its therapeutic effects and usually it can be impeded by limited ability of the compound to reach targeted cells and tissues. Improvement of such compounds to enter the targeted cells of tissues by a variety of means of delivery is crucial. The present invention relates the novel lipids, in compositions and methods for preparation that facilitate the targeted intracellular delivery of biological active molecules.

Additional examples of biologically active molecules for which effective targeting to a patient's tissues is often not achieved include numerous proteins, including immunoglobins, and many low molecular weight compounds, whether synthetic or naturally occurring, such as the peptide hormones and antibiotics.

SUMMARY

What is described is a compound of formula I

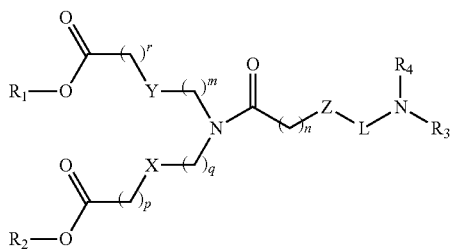

wherein
X is an alkylene or an alkenylene;
Y is a monocyclic, bicyclic, or tricyclic arene or heteroarene;
Z is S or O;
L is a linear or branched alkylene of 1 to 6 carbons;
$R_3$ and $R_4$ are independently a linear or branched alkyl of 1 to 6 carbons;
$R_1$ is a branched alkyl or alkenyl of 1 to 25 carbons;
$R_2$ is an alkyl or an alkenyl of 1 to 20 carbons;
r is 0 to 6; and
m, n, p, and q are independently 1 to 18;
or a pharmaceutically acceptable salt thereof.

Preferably the compound of formula 1 consists of an arene, most preferably a benzene, naphthalene, or anthracene. Preferably, the compound of formula 1 consists of r=0 and/or has Z=S. The compound of formula 1 preferably consists of L=$C_2$, $C_3$, $C_4$, $C_5$, or $C_6$ alkylene. The compound of formula 1 preferably consists of $R_3$ and $R_4$ as methyl, ethyl or propyl.

Another aspect of the disclosure is a compound of formula II or formula III

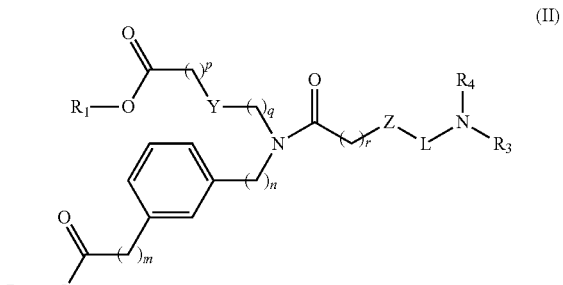

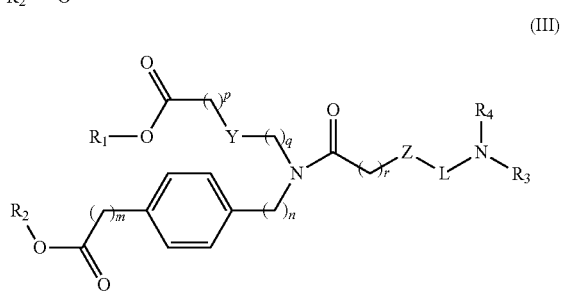

wherein
Y is an alkylene;
Z is S or O;
L is a linear or branched alkylene of 2, 3, 4, 5 or 6 carbons;
$R_3$ and $R_4$ are independently a linear alkyl of 1, 2, 3, 4, 5, or 6 carbons;
$R_1$ is a branched alkyl of 1 to 24 carbons;
$R_2$ is a linear alkyl or alkenyl of 1 to 20 carbons;
r is 0 to 6; and
m, n, p, and q are independently 1 to 18;
or a pharmaceutically acceptable salt thereof.

The compound of formula II or III preferably consists of n and m each 1, 2, 3 or 4. Preferably the compound of formula II or III consists of $R_1$ as a branched alkyl of 3, 4, 5, 6, 7, 8, 9, 10, 11, 12, 13, 14, 15, 16, 17, 18, 19, 20, 21, 22, 23, or 24 carbons, most preferably with both alkyl branches of the same length. Preferably, the compound of formula II or II consists of Y as a bond, r=0, and/or Z=S.

DETAILED DESCRIPTION OF THE DRAWINGS

DETAILED DESCRIPTION OF ILLUSTRATIVE EMBODIMENTS

Definitions

Figure 1:
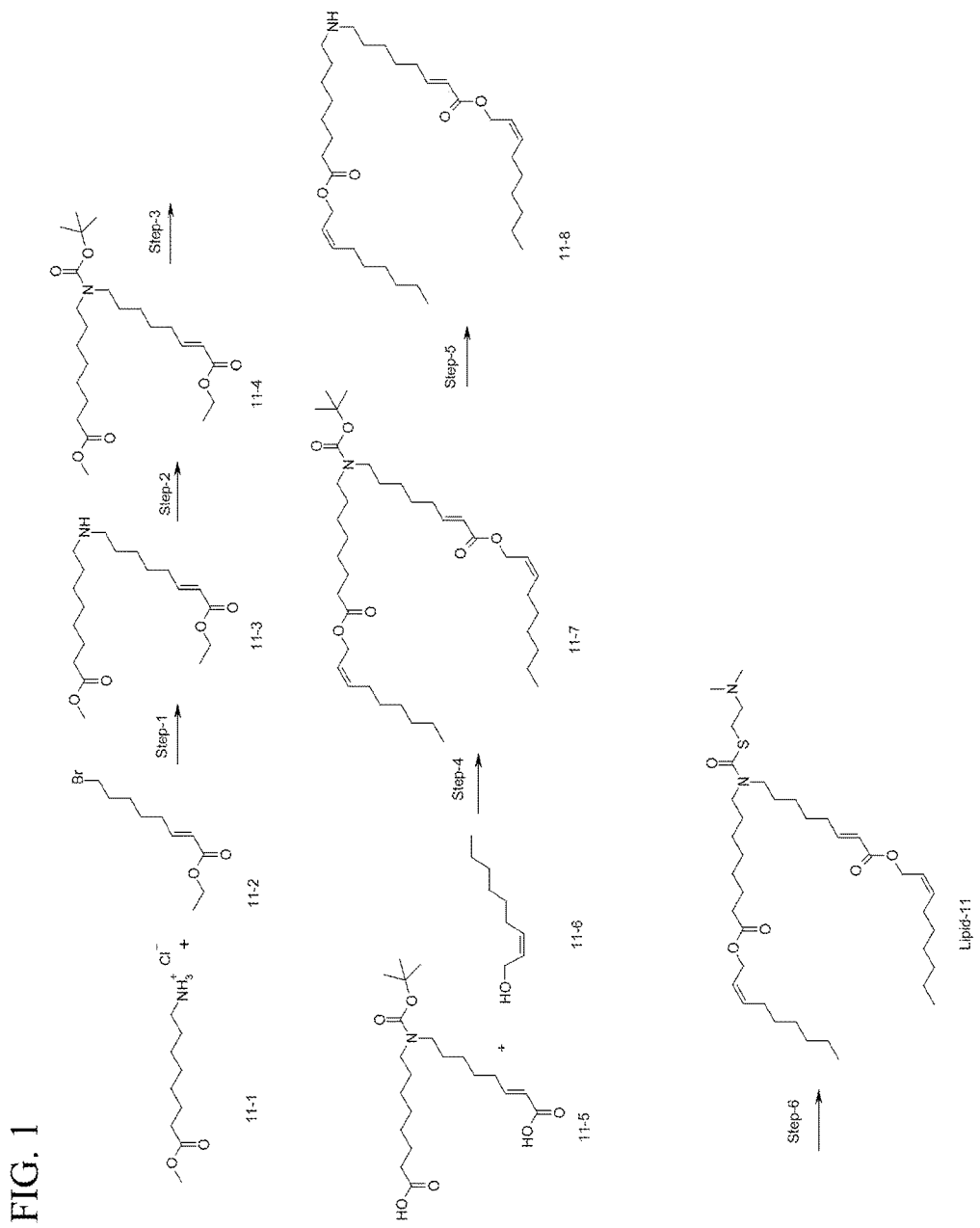
FIG. 1 shows the preparation of Lipid 11, showing intermediates 11-1 to 11-8. 11-1 and 11-6 are commercial starting materials. The reactions are described in detail in Example 2.

"At least one" means one or more (e.g., 1-3, 1-2, or 1).

"Composition" includes a product comprising the specified ingredients in the specified amounts, as well as any product that results, directly or indirectly, from combination of the specified ingredients in the specified amounts.

"In combination with" as used to describe the administration of a compound of formulas 1, I, and II with other medicaments in the methods of treatment of this invention, means—that the compounds of formulas 1, I, and II and the other medicaments are administered sequentially or concurrently in separate dosage forms, or are administered concurrently in the same dosage form.

"Mammal" means a human or other mammal, or means a human being.

"Patient" includes both human and other mammals, preferably human.

"Alkyl" is a monovalent saturated or unsaturated, straight or branched, hydrocarbon chain. In various embodiments, the alkyl group has 1-30 carbon atoms, i.e. is a $C_1$-$C_{18}$ group, or is a $C_1$-$C_{12}$ group, a $C_1$-$C_6$ group, or a $C_1$-$C_4$ group. Independently, in various embodiments, the alkyl group has zero branches (i.e., is a straight chain), one branch, two branches, or more than two branches. "Alkenyl" is an unsaturated alkyl that may have one double bond, two double bonds, more than two double bonds. "Alkynal" is an unsaturated alkyl that may have one triple bond, two triple bonds, or more than two triple bonds. Alkyl chains may be optionally substituted with 1 substituent (i.e., the alkyl group is mono-substituted), or 1-2 substituents, or 1-3 substituents, or 1-4 substituents, etc. The substituents may be selected from the group consisting of hydroxy, amino, alkylamino, boronyl, carboxy, nitro, cyano, esters, acids, amides, esterified alcohol or amides formed from amines, and the like. When the alkyl group incorporates one or more heteroatoms, the alkyl group is referred to herein as a heteroalkyl group. When the substituents on an alkyl group are hydrocarbons, then the resulting group is simply referred to as a substituted alkyl. In various aspects, the alkyl group including substituents has less than 25, 24, 23, 22, 21, 20, 19, 18, 17, 16, 15, 14, 13, 12, 11, 10, 9, 8, or 7 carbons.

"Alkylene" is a bivalent saturated straight or branched, hydrocarbon chain of 1-30 carbon atoms. An "alkenylene" is a bivalent, unsaturated hydrocarbon chain that may have one double bond, two double bonds, more than two double bonds, and zero branches, one branch, or two or more branches.

"Lower alkyl" means a group having one to six carbon atoms in the chain which chain may be straight or branched. Non-limiting examples of suitable alkyl groups include methyl, ethyl, n-propyl, isopropyl, n-butyl, t-butyl, n-pentyl, and hexyl.

"Alkoxy" means an alkyl-O-group wherein alkyl is as defined above. Non-limiting examples of alkoxy groups include: methoxy, ethoxy, n-propoxy, isopropoxy, n-butoxy and heptoxy. The bond to the parent moiety is through the ether oxygen.

"Alkoxyalkyl" means an alkoxy-alkyl-group in which the alkoxy and alkyl are as previously described. Preferred alkoxyalkyl comprise a lower alkyl group. The bond to the parent moiety is through the alkyl.

"Alkylaryl" means an alkyl-aryl-group in which the alkyl and aryl are as previously described, including alkylheteroaryl. Preferred alkylaryls comprise a lower alkyl group. The bond to the parent moiety is through the aryl.

"Aminoalkyl" means an $NH_2$-alkyl-group, wherein alkyl is as defined above, bound to the parent moiety through the alkyl group.

"Aromatic ring" means a monocyclic, bicyclic, or tricyclic arene or heteroarene.

"Arenes" and "heteroarenes" mean a moiety selected from group consisting of furan, benzofuran, isobenzofuran, pyrrole, indole, isoindole, thiophene, benzothiophene, benzo[c]thiophene, imidazole, benzimidazole, purine, pyrazole, indazol, oxazole, benzoxazole, isoxazole, benzisoxazole, thiazole, benzothiazole, benzene, naphthalene, anthracene, pyridine, quinolone, isoquinoline, pyrazine, quinoxaline, acridine, pyrimidine, quinazoline, pyridazine, pyridazine, cinnoline phthalazin, 1,2,3-triazine, 1,2,4-triazine, and 1,3,5-triazine (s-triazine).

Arene "substituents" means halo, alkyl, alkenyl, alkynyl, aryl, heterocyclyl, thiol, alkylthio, oxo, thioxy, alkylthioalkyl, alkylsulfonyl, alkylsulfonylalkyl, alkoxy, aryloxy, aralkoxy, aminocarbonyl, alkylaminocarbonyl, alkoxycarbonyl, haloalkyl, amino, trifluoromethyl, cyano, nitro, alkylamino, alkylaminoalkyl, aminoalkylamino, hydroxy, alkoxyalkyl, carboxyalkyl, alkoxycarbonylalkyl, aminocarbonylalkyl, acyl, carboxylic acid, sulfonic acid, sulfonyl, phosphonic acid, and aliphatic.

"Carboxyalkyl" means an HOOC-alkyl-group, wherein alkyl is as defined above, bound to the parent moiety through the alkyl group.

"Halo" and "halogen" means fluoro, chloro, bromo, or iodo groups. Preferred are fluoro, chloro or bromo, and more preferred are fluoro and chloro.

"Heteroalkyl" is a saturated or unsaturated, straight or branched, chain containing carbon and at least one heteroatom. The heteroalkyl group may, in various embodiments, have on heteroatom, or 1-2 heteroatoms, or 1-3 heteroatoms, or 1-4 heteroatoms. In one aspect the heteroalkyl chain contains from 1 to 18 (i.e., 1-18) member atoms (carbon and heteroatoms), and in various embodiments contain 1-12, or 1-6, or 1-4 member atoms. Independently, in various embodiments, the heteroalkyl group has zero branches (i.e., is a straight chain), one branch, two branches, or more than two branches. Independently, in one embodiment, the heteroalkyl group is saturated. In another embodiment, the heteroalkyl group is unsaturated. In various embodiments, the unsaturated heteroalkyl may have one double bond, two double bonds, more than two double bonds, and/or one triple bond, two triple bonds, or more than two triple bonds. Heteroalkyl chains may be substituted or unsubstituted. In one embodiment, the heteroalkyl chain is unsubstituted. In another embodiment, the heteroalkyl chain is substituted. A substituted heteroalkyl chain may have 1 substituent (i.e., by monosubstituted), or may have, e.g., 1-2 substituents, or 1-3 substituents, or 1-4 substituents. Exemplary heteroalkyl substituents include esters (—C(O)—O—R), amides (—C(O)—NH—R), carbonyls (—C(O)—), ethers (—C—O—C), and amines (—C—NR$_1$R$_2$), in which R, R$_1$, and R$_2$ are each an alkyl group.

"Hydroxyalkyl" means an HO-alkyl-group, in which alkyl is previously defined. Preferred hydroxyalkyls contain lower alkyl. Non-limiting examples of suitable hydroxyalkyl groups include hydroxymethyl and 2-hydroxyethyl.

"Hydrate" is a solvate wherein the solvent molecule is H$_2$O.

"Lipid" means an organic compound that comprises an ester of fatty acid and is characterized by being insoluble in water, but soluble in many organic solvents. Lipids are usually divided into at least three classes: (1) "simple lipids," which include fats and oils as well as waxes; (2) "compound lipids," which include phospholipids and glycolipids; and (3) "derived lipids" such as steroids.

"Lipid particle" means a lipid formulation that can be used to deliver a therapeutic nucleic acid (e.g., mRNA) to a target site of interest (e.g., cell, tissue, organ, and the like). In preferred embodiments, the lipid particle is a nucleic acid-lipid particle, which is typically formed from a cationic lipid, a non-cationic lipid (e.g., a phospholipid), a conjugated lipid that prevents aggregation of the particle (e.g., a PEG-lipid), and optionally cholesterol. Typically, the therapeutic nucleic acid (e.g., mRNA) may be encapsulated in the lipid portion of the particle, thereby protecting it from enzymatic degradation.

Lipid particles typically have a mean diameter of from 30 nm to 150 nm, from 40 nm to 150 nm, from 50 nm to 150 nm, from 60 nm to 130 nm, from 70 nm to 110 nm, from 70 nm to 100 nm, from 80 nm to 100 nm, from 90 nm to 100 nm, from 70 to 90 nm, from 80 nm to 90 nm, from 70 nm to 80 nm, or 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. In addition, nucleic acids, when present in the lipid particles of the present invention, are resistant in aqueous solution to degradation with a nuclease.

"Solvate" means a physical association of a compound of this disclosure with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like.

"Lipid encapsulated" can mean a lipid particle that provides a therapeutic nucleic acid such as an mRNA with full encapsulation, partial encapsulation, or both. In a preferred embodiment, the nucleic acid (e.g., mRNA) is fully encapsulated in the lipid particle.

"Lipid conjugate" means a conjugated lipid that inhibits aggregation of lipid particles. Such lipid conjugates include, but are not limited to, PEG-lipid conjugates such as, e.g., PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides, cationic PEG lipids, polyoxazoline (POZ)-lipid conjugates, polyamide oligomers (e.g., ATTA-lipid conjugates), and mixtures thereof. PEG or POZ can be conjugated directly to the lipid or may be linked to the lipid via a linker moiety. Any linker moiety suitable for coupling the PEG or the POZ to a lipid can be used including, e.g., non-ester-containing linker moieties and ester-containing linker moieties. In certain preferred embodiments, non-ester-containing linker moieties, such as amides or carbamates, are used.

"Amphipathic lipid" means the material in which the hydrophobic portion of the lipid material orients into a hydrophobic phase, while the hydrophilic portion orients toward the aqueous phase. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). Examples of amphipathic compounds include, but are not limited to, phospholipids, aminolipids, and sphingolipids.

Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, and dilinoleoylphosphatidylcholine. Other compounds lacking in phosphorus, such as sphingolipid, glycosphingolipid families, diacylglycerols, and β-acyloxyacids, are also within the group designated as amphipathic lipids. Additionally, the amphipathic lipids described above can be mixed with other lipids including triglycerides and sterols.

"Neutral lipid" means a lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

"Non-cationic lipid" means an amphipathic lipid or a neutral lipid or anionic lipid, and are described in more detail below.

"Anionic lipid" means a lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

The term "hydrophobic lipid" means a compound having apolar groups that include, but are not limited to, long-chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N—N-dialkylamino, 1,2-diacyloxy-3-aminopropane, and 1,2-dialkyl-3-aminopropane.

The terms "cationic lipid" and "amino lipid" are used interchangeably herein to include those lipids and salts thereof having one, two, three, or more fatty acid or fatty alkyl chains and a pH-titratable amino head group (e.g., an alkylamino or dialkylamino head group). The cationic lipid is typically protonated (i.e., positively charged) at a pH below the $pK_a$ of the cationic lipid and is substantially neutral at a pH above the $pK_a$. The cationic lipids of the invention may also be termed titratable cationic lipids. In some embodiments, the cationic lipids comprise: a protonatable tertiary amine (e.g., pH-titratable) head group; $C_{18}$ alkyl chains, wherein each alkyl chain independently has 0 to 3 (e.g., 0, 1, 2, or 3) double bonds; and ether, ester, or ketal linkages between the head group and alkyl chains. Such cationic lipids include, but are not limited to, 1,2-distearyloxy-N,N-dimethyl-3-aminopropane (DSDMA), 2-dioleyloxy-N,N-dimethyl-3-aminopropane (DODMA), 1,2-dilinoleyloxy-N,N-dimethyl-3-aminopropane (DLinDMA), and 1,2-dilinolenyloxy-N,N-dimethyl-3-aminopropane (DLenDMA).

The term "substituted" means substitution with specified groups other than hydrogen, or with one or more groups, moieties, or radicals which can be the same or different, with each, for example, being independently selected.

By "antisense nucleic acid", it is meant a non-enzymatic nucleic acid molecule that binds to target RNA by means of RNA-RNA or RNA-DNA or RNA-PNA (protein nucleic acid. Typically, antisense molecules are complementary to a target sequence along a single contiguous sequence of the antisense molecule. However, in certain embodiments, an antisense molecule can bind to substrate such that the substrate molecule forms a loop, and/or an antisense molecule can bind such that the antisense molecule forms a loop. Thus, the antisense molecule can be complementary to two (or even more) non-contiguous substrate sequences or two (or even more) non-contiguous sequence portions of an antisense molecule can be complementary to a target sequence or both. In addition, antisense DNA can be used to target RNA by means of DNA-RNA interactions, thereby activating RNase H, which digests the target RNA in the duplex. The antisense oligonucleotides can comprise one or more RNAse H activating region, which is capable of activating RNAse H cleavage of a target RNA. Antisense DNA can be synthesized chemically or expressed via the use of a single stranded DNA expression vector or equivalent thereof. "Antisense RNA" is an RNA strand having a sequence complementary to a target gene mRNA, that can induce RNAi by binding to the target gene mRNA. "Antisense RNA" is an RNA strand having a sequence complementary to a target gene mRNA, and thought to induce RNAi by binding to the target gene mRNA. "Sense RNA" has a sequence complementary to the antisense RNA, and annealed to its complementary antisense RNA to form iNA. These antisense and sense RNAs have been conventionally synthesized with an RNA synthesizer.

"Nucleic acid" refers to deoxyribonucleotides or ribonucleotides and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2'-O-methyl ribonucleotides, peptide-nucleic acids (PNAs).

By "RNA" is meant a molecule comprising at least one ribonucleotide residue. By "ribonucleotide" is meant a nucleotide with a hydroxyl group at the 2' position of a β-D-ribo-furanose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution, and/or alteration of one or more nucleotides. Such alterations can include addition of non-nucleotide material, such as to the end(s) of an interfering RNA or internally, for example at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA. As used herein, the terms "ribonucleic acid" and "RNA" refer to a molecule containing at least one ribonucleotide residue, including siRNA, antisense RNA, single stranded RNA, microRNA, mRNA, noncoding RNA, and multivalent RNA. A ribonucleotide is a nucleotide with a hydroxyl group at the 2' position of a β-D-ribo-furanose moiety. These terms include double-stranded RNA, single-stranded RNA, isolated RNA such as partially purified RNA, essentially pure RNA, synthetic RNA, recombinantly produced RNA, as well as modified and altered RNA that differs from naturally occurring RNA by the addition, deletion, substitution, modification, and/or alteration of one or more nucleotides. Alterations of an RNA can include addition of non-nucleotide material, such as to the end(s) of an interfering RNA or internally, for example at one or more nucleotides of an RNA nucleotides in an RNA molecule include non-standard nucleotides, such as non-naturally occurring nucleotides or chemically synthesized nucleotides or deoxynucleotides. These altered RNAs can be referred to as analogs.

By "nucleotide" as used herein is as recognized in the art to include natural bases (standard), and modified bases well known in the art. Such bases are generally located at the 1' position of a nucleotide sugar moiety. Nucleotides generally comprise a base, sugar, and a phosphate group. The nucleotides can be unmodified or modified at the sugar, phosphate, and/or base moiety, (also referred to interchangeably as nucleotide analogs, modified nucleotides, non-natural nucleotides, non-standard nucleotides and other. There are several examples of modified nucleic acid bases known in the art as summarized. Some of the non-limiting examples of base modifications that can be introduced into nucleic acid molecules include: inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g., 6-methyluridine), propyne, and others. By "modified bases" in this aspect is meant nucleotide bases other than adenine, guanine, cytosine, and uracil at 1' position or their equivalents.

As used herein complementary nucleotide bases are a pair of nucleotide bases that form hydrogen bonds with each other. Adenine (A) pairs with thymine (T) or with uracil (U) in RNA, and guanine (G) pairs with cytosine (C). Complementary segments or strands of nucleic acid that hybridize (join by hydrogen bonding) with each other. By "complementary" is meant that a nucleic acid can form hydrogen bond(s) with another nucleic acid sequence either by traditional Watson-Crick or by other non-traditional modes of binding.

MicroRNAs (miRNA) are single-stranded RNA molecules of 21-23 nucleotides in length, which regulate gene expression miRNAs are encoded by genes that are transcribed from DNA but not translated into protein (noncoding RNA); instead they are processed from primary transcripts known as pri-miRNA to short stem-loop structures called pre-miRNA and finally to functional miRNA. Mature miRNA molecules are partially complementary to one or more messenger RNA (mRNA) molecules, and their main function is to downregulate gene expression As used herein the term "small interfering RNA (siRNA)", sometimes known as short interfering RNA or silencing RNA, is used to refer to a class of double-stranded RNA molecules, 16-40 nucleotides in length, that play a variety of roles in biology. Most notably, siRNA is involved in the RNA interference (RNAi) pathway, where it interferes with the expression of a specific gene. In addition to their role in the RNAi pathway, siRNAs also act in RNAi-related pathways, e.g., as an antiviral mechanism or in shaping the chromatin structure of a genome; the complexity of these pathways is only now being elucidated.

As used herein, the term RNAi refers to an RNA-dependent gene silencing process that is controlled by the RNA-induced silencing complex (RISC) and is initiated by short double-stranded RNA molecules in a cell, where they interact with the catalytic RISC component argonaute. When the double-stranded RNA or RNA-like iNA or siRNA is exogenous (coming from infection by a virus with an RNA genome or from transfected iNA or siRNA), the RNA or iNA is imported directly into the cytoplasm and cleaved to short fragments by the enzyme dicer. The initiating dsRNA can also be endogenous (originating in the cell), as in pre-microRNAs expressed from RNA-coding genes in the genome. The primary transcripts from such genes are first processed to form the characteristic stem-loop structure of pre-miRNA in the nucleus, then exported to the cytoplasm to be cleaved by dicer. Thus, the two dsRNA pathways, exogenous and endogenous, converge at the RISC complex. The active components of an RNA-induced silencing complex (RISC) are endonucleases called argonaute proteins, which cleave the target mRNA strand complementary to their bound siRNA or iNA. As the fragments produced by dicer are double-stranded, they could each in theory produce a functional siRNA or iNA. However, only one of the two strands, which is known as the guide strand, binds the argonaute protein and directs gene silencing. The other anti-guide strand or passenger strand is degraded during RISC activation.

Ionizable Cationic Lipid Molecules Having Aromatic Side Chains

What is described is a compound of formula I

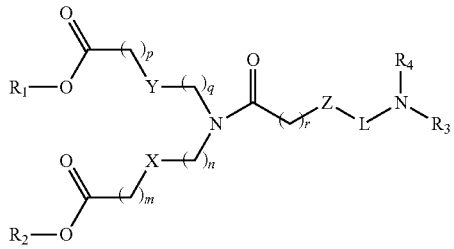

wherein
X is an alkylene or an alkenylene;
Y is a monocyclic, bicyclic, or tricyclic arene or heteroarene;
Z is S or O;
L is a linear or branched alkylene of 1 to 6 carbons;
$R_3$ and $R_4$ are independently a linear or branched alkyl of 1, 2, 3, 4, 5, or 6 carbons;
$R_1$ is a branched alkyl or alkenyl of 1, 2, 3, 4, 5, 6, 7, 8, 9, 10, 11, 12, 13, 14, 15, 16, 17, 18, 19, 20, 21, 22, 23, 24, or 25 carbons;
$R_2$ is an alkyl or an alkenyl of 1 to 20 carbons;
r is 0 to 6; and
m, n, p, and q are independently 1, 2, 3, 4, 5, 6, 7, 8, 9, 10, 11, 12, 13, 14, 15, 16, 17, or 18;
or a pharmaceutically acceptable salt thereof.

In one aspect of the compound of formula I, $R_1$ is methyl, Y is a bond, and p+q=6, 7, 8, 9, 10, 11, 12, 13, 14, 15, 16, 17, 18, 19, or 20. Preferably p+q=8. Preferably, r=0 and Z is S, and most preferably $R_3$ and $R_4$ are methyl. Preferably, *—Z-L-NR$_3$R$_4$ consists of a moiety selected from

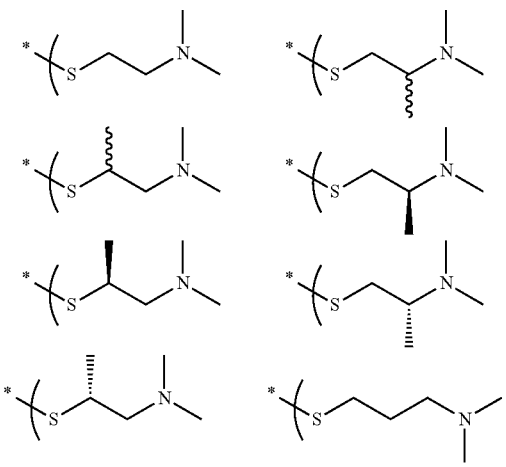

In another aspect of the compound of formula I, X is a monocyclic, bicyclic, or tricyclic aromatic hydrocarbon ring (e.g., a benzene, naphthalene, or anthracene), including a heteroaromatic ring in which at least one ring atom is substituted by a nitrogen, sulfur, or oxygen. The aromatic hydrocarbon ring and heteroaromatic ring may be phenyl, furan, benzofuran, isobenzofuran, pyrrole, indole, isoindole, thiophene, benzothiophene, benzo[c]thiophene, imidazole, benzimidazole, purine, pyrazole, indazol, oxazole, benzoxazole, isoxazole, benzisoxazole, thiazole, benzothiazole, benzene, naphthalene, anthracene, pyridine, quinolone, isoquinoline, pyrazine, quinoxaline, acridine, pyrimidine, quinazoline, pyridazine, pyridazine, cinnoline phthalazin, 1,2,3-triazine, 1,2,4-triazine, and 1,3,5-triazine (s-triazine). The aromatic or heteroaromatic hydrocarbon ring may include a substituent, e.g., a halo (fluoro, chloro, bromo or iodo), alkyl, alkenyl, alkynyl, aryl, heterocyclyl, thiol, alkylthio, oxo, thioxy, alkylthioalkyl, alkylsulfonyl, alkylsulfonylalkyl, alkoxy, aryloxy, aralkoxy, aminocarbonyl, alkylaminocarbonyl, alkoxycarbonyl, haloalkyl, amino, trifluoromethyl, cyano, nitro, alkylamino, alkylaminoalkyl, aminoalkylamino, hydroxy, alkoxyalkyl, carboxyalkyl, alkoxycarbonylalkyl, aminocarbonylalkyl, acyl, carboxylic acid, sulfonic acid, sulfonyl, phosphonic acid, or aliphatic. The alkyl substituent may be a straight chain or branched, noncyclic or cyclic, saturated aliphatic hydrocarbon of 1, 2, 3, 4, 5, 6, 7, 8, 9, or 10 carbon atoms, preferably a methyl, ethyl, n-propyl, n-butyl, n-pentyl, or n-hexyl.

In another embodiment, the compound is formula II.

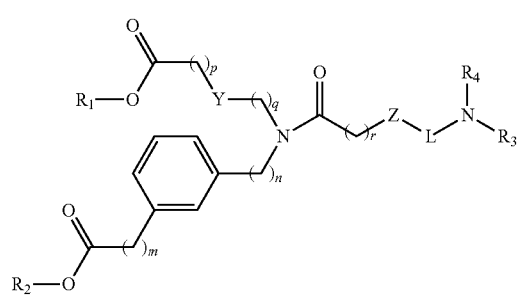

wherein
Y is an alkylene;
Z is S or O;
L is a linear or branched alkylene of 2, 3, 4, 5 or 6 carbons;
$R_3$ and $R_4$ are independently a linear alkyl of 1, 2, 3, 4, 5, or 6 carbons;
$R_1$ is a branched alkyl of 1, 2, 3, 4, 5, 6, 7, 8, 9, 10, 11, 12, 13, 14, 15, 16, 17, 18, 19, 20, 21, 22, 23, or 24 carbons;
$R_2$ is a linear alkyl or alkenyl of 1, 2, 3, 4, 5, 6, 7, 8, 9, 10, 11, 12, 13, 14, 15, 16, 17, 18, 19, or 20 carbons;
r is 0 to 6; and
m, n, p, and q are independently 1, 2, 3, 4, 5, 6, 7, 8, 9, 10, 11, 12, 13, 14, 15, 16, 17, or 18.

In one aspect of the compound formula II, n is preferably 1, 2, 3, or 4, and m is 1 2, 3, 4, or 5. In another aspect, $R_1$ and $R_2$ are preferably a linear or branched alkyl or alkenyl of carbons. In another aspect, preferably Y is a bond and p+q=8. In another aspect, preferably $R_3$ and $R_4$ are methyl, r is 0, and Z is S. The compound of claim 30, wherein *—Z-L-NR$_3$R$_4$ consists of a moiety selected from In another embodiment, the compound is formula III.

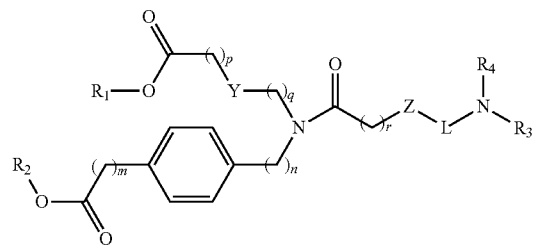

wherein
Y is an alkylene;
Z is S or O;
L is a linear or branched alkylene of 2, 3, 4, 5 or 6 carbons;
$R_3$ and $R_4$ are independently a linear alkyl of 1, 2, 3, 4, 5, or 6 carbons;
$R_1$ is a branched alkyl of 1, 2, 3, 4, 5, 6, 7, 8, 9, 10, 11, 12, 13, 14, 15, 16, 17, 18, 19, 20, 21, 22, 23, or 24 carbons;
$R_2$ is a linear alkyl or alkenyl of 1, 2, 3, 4, 5, 6, 7, 8, 9, 10, 11, 12, 13, 14, 15, 16, 17, 18, 19, or 20 carbons;
r is 0 to 6; and
m, n, p, and q are independently 1, 2, 3, 4, 5, 6, 7, 8, 9, 10, 11, 12, 13, 14, 15, 16, 17, or 18.

In another aspect Y preferably is a bond and p+q=8. In another aspect, $R_3$ and $R_4$ are preferably methyl, r is 0, and Z is S.

The compounds of formula I, II, or III form may be a pharmaceutically acceptable salt thereof, in a lipid composition, comprising a nanoparticle or a bilayer of lipid molecules. The lipid bilayer preferably further comprises a neutral lipid or a polymer. The lipid composition preferably comprises a liquid medium. The composition preferably further encapsulates a nucleic acid. The nucleic acid preferably has an activity of suppressing the expression of the target gene by utilizing RNA interference (RNAi). The lipid composition preferably further comprises a nucleic acid and a neutral lipid or a polymer. The lipid composition preferably encapsulates the nucleic acid.

The compounds of formula I, II, or III form salts that are also within the scope of this disclosure. Reference to a compound of formula I herein is understood to include reference to salts thereof, unless otherwise indicated. The term "salt(s)" as employed herein denotes acidic salts formed with inorganic and/or organic acids, as well as basic salts formed with inorganic and/or organic bases. In addition, such salts of a compound of formula I may contains a basic moiety, such as, but not limited to, a pyridine or imidazole, or an acidic moiety, such as, but not limited to, a carboxylic acid, and zwitterions ("inner salts"). The salts can be pharmaceutically acceptable (i.e., non-toxic, physiologically acceptable) salts, although other salts are also useful. Salts of the compounds of the formula I may be formed, for example, by reacting a compound of formula I with an amount of acid or base, such as an equivalent amount, in a medium such as one in which the salt precipitates or in an aqueous medium followed by lyophilization.

Exemplary acid addition salts of the compounds of formula I, II, or III include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-napthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates) undecanoates, and the like. Additionally, acids which are generally considered suitable for the formation of pharmaceutically useful salts from basic pharmaceutical compounds are discussed, for example, by S. Berge et al, *J. Pharmaceutical Sciences* (1977) 66(1)1-19; P. Gould, International *J. Pharmaceutics* (1986) 33 201-217; Anderson et al, The Practice of Medicinal Chemistry (1996), Academic Press, New York; and in The Orange Book (Food & Drug Administration, Washington, D.C. on their website). These disclosures are incorporated by reference herein.

Exemplary basic salts of the compounds of formula I, II, or III include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine or lysine. Basic nitrogen-containing groups may be quarternized with agents such as lower alkyl halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

All such acid and base salts are intended to be pharmaceutically acceptable salts within the scope of the disclosure and all acid and base salts are considered equivalent to the free forms of the corresponding compounds of formula I for purposes of the disclosure.

Compounds of formula I, II, or III can exist in unsolvated and solvated forms, including hydrated forms. In general, the solvated forms, with pharmaceutically acceptable solvents such as water, ethanol, and the like, are equivalent to the unsolvated forms for the purposes of this disclosure.

Compounds of formula I, II, or III and salts, solvates thereof, may exist in their tautomeric form (for example, as an amide or imino ether). All such tautomeric forms are contemplated herein as part of the present disclosure.

Also within the scope of the present disclosure are polymorphs of the compounds of this disclosure (i.e., polymorphs of the compounds of formula I are within the scope of this disclosure).

All stereoisomers (for example, geometric isomers, optical isomers, and the like) of the present compounds (including those of the salts, solvates, and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this disclosure. Individual stereoisomers of the compounds of this disclosure may, for example, be substantially free of other isomers, or may be admixed, for example, as racemates or with all other, or other selected, stereoisomers. The chiral centers of the compounds herein can have the S or R configuration as defined by the IUPAC 1974 Recommendations. The use of the terms "salt", "solvate", and the like, is intended to equally apply to the salt and solvate of enantiomers, stereoisomers, rotamers, tautomers, racemates, or prodrugs of the disclosed compounds.

Classes of compounds that can be used as the chemotherapeutic agent (antineoplastic agent) include: alkylating agents, antimetabolites, natural products and their derivatives, hormones and steroids (including synthetic analogs), and synthetics. Examples of compounds within these classes are given below.

Lipid Particles

The description provides lipid particles comprising one or more therapeutic mRNA molecules encapsulated within the lipid particles.

In some embodiments, the mRNA is fully encapsulated within the lipid portion of the lipid particle such that the mRNA in the lipid particle is resistant in aqueous solution to nuclease degradation. In other embodiments, the lipid particles described herein are substantially non-toxic to mammals such as humans. The lipid particles typically have a mean diameter of from 30 nm to 150 nm, from 40 nm to 150 nm, from 50 nm to 150 nm, from 60 nm to 130 nm, from 70 nm to 110 nm, or from 70 to 90 nm. The lipid particles of the invention also typically have a lipid:RNA ratio (mass/mass ratio) of from 1:1 to 100:1, from 1:1 to 50:1, from 2:1 to 25:1, from 3:1 to 20:1, from 5:1 to 15:1, or from 5:1 to 10:1, or from 10:1 to 14:1, or from 9:1 to 20:1. In one embodiment, the lipid particles have a lipid: RNA ratio (mass/mass ratio) of 12:1. In another embodiment, the lipid particles have a lipid: mRNA ratio (mass/mass ratio) of 13:1.

In preferred embodiments, the lipid particles comprise an mRNA, a cationic lipid (e.g., one or more cationic lipids or salts thereof described herein), a phospholipid, and a conjugated lipid that inhibits aggregation of the particles (e.g., one or more PEG-lipid conjugates). The lipid particles can also include cholesterol. The lipid particles may comprise at least 1, 2, 3, 4, 5, 6, 7, 8, 9, 10, or more mRNA that express one or more polypeptides.

In the nucleic acid-lipid particles the mRNA may be fully encapsulated within the lipid portion of the particle, thereby protecting the nucleic acid from nuclease degradation. In preferred embodiments, a lipid particle comprising an mRNA is fully encapsulated within the lipid portion of the particle, thereby protecting the nucleic acid from nuclease degradation. In certain instances, the mRNA in the lipid particle is not substantially degraded after exposure of the particle to a nuclease at 37° C. for at least 20, 30, 45, or 60 minutes. In certain other instances, the mRNA in the lipid particle is not substantially degraded after incubation of the particle in serum at 37° C. for at least 30, 45, or 60 minutes or at least 2, 3, 4, 5, 6, 7, 8, 9, 10, 12, 14, 16, 18, 20, 22, 24, 26, 28, 30, 32, 34, or 36 hours. In other embodiments, the mRNA is complexed with the lipid portion of the particle. One of the benefits of the formulations of the present invention is that the nucleic acid-lipid particle compositions are substantially non-toxic to mammals such as humans.

"Fully encapsulated" means that the nucleic acid (e.g., mRNA) in the nucleic acid-lipid particle is not significantly degraded after exposure to serum or a nuclease assay that would significantly degrade free RNA. When fully encapsulated, preferably less than 25% of the nucleic acid in the particle is degraded in a treatment that would normally degrade 100% of free nucleic acid, more preferably less than 10%, and most preferably less than 5% of the nucleic acid in the particle is degraded. "Fully encapsulated" also means that the nucleic acid-lipid particles do not rapidly decompose into their component parts upon in vivo administration.

In the context of nucleic acids, full encapsulation may be determined by performing a membrane-impermeable fluorescent dye exclusion assay, which uses a dye that has enhanced fluorescence when associated with nucleic acid. Encapsulation is determined by adding the dye to a liposomal formulation, measuring the resulting fluorescence, and comparing it to the fluorescence observed upon addition of a small amount of nonionic detergent. Detergent-mediated disruption of the liposomal bilayer releases the encapsulated nucleic acid, allowing it to interact with the membrane-impermeable dye. Nucleic acid encapsulation may be calculated as $E=(I_0-I)/I_0$, where/and $I_0$ refers to the fluorescence intensities before and after the addition of detergent.

In other embodiments, the present invention provides a nucleic acid-lipid particle composition comprising a plurality of nucleic acid-lipid particles.

The lipid particle comprises mRNA that is fully encapsulated within the lipid portion of the particles, such that from 30% to 100%, from 40% to 100%, from 50% to 100%, from 60% to 100%, from 70% to 100%, from 80% to 100%, from 90% to 100%, from 30% to 95%, from 40% to 95%, from 50% to 95%, from 60% to 95%, from 70% to 95%, from 80% to 95%, from 85% to 95%, from 90% to 95%, from 30% to 90%, from 40% to 90%, from 50% to 90%, from 60% to 90%, from 70% to 90%, from 80% to 90%, or at least 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the particles have the mRNA encapsulated therein.

Depending on the intended use of the lipid particles, the proportions of the components can be varied and the delivery efficiency of a particular formulation can be measured using assays know in the art.

Cationic Lipids

The description includes synthesis of certain cationic lipid compounds. The compounds are particularly suitable for delivering polynucleotides to cells and tissues as demonstrated in subsequent sections. The lipomacrocycle compound described herein may be used for other purposes as well as, for example, recipients and additives.

The synthetic methods for the cationic lipid compounds can be synthesized with the skills in the art. The skilled of the art will recognize other methods to produce these compounds, and to produce also the other compounds of the description.

The cationic lipid compounds may be combined with an agent to form microparticles, nanoparticles, liposomes, or micelles. The agent to be delivered by the particles, liposomes, or micelles may be in the form of a gas, liquid, or solid, and the agent may be a polynucleotide, protein, peptide, or small molecule. The lipomacrocycle compounds may be combined with other cationic lipid compounds, polymers (synthetic or natural), surfactants, cholesterol, carbohydrates, proteins, or lipids, to form the particles. These particles may then optionally be combined with a pharmaceutical excipient to form a pharmaceutical composition.

The present description provides novel cationic lipid compounds and drug delivery systems based on the use of such cationic lipid compounds. The system may be used in the pharmaceutical/drug delivery arts to deliver polynucleotides, proteins, small molecules, peptides, antigen, or drugs, to a patient, tissue, organ, or cell. These novel compounds may also be used as materials for coating, additives, excipients, materials, or bioengineering.

The cationic lipid compounds of the present description provide for several different uses in the drug delivery art.

The amine-containing portion of the cationic lipid compounds may be used to complex polynucleotides, thereby enhancing the delivery of polynucleotide and preventing their degradation. The cationic lipid compounds may also be used in the formation of picoparticles, nanoparticles, microparticles, liposomes, and micelles containing the agent to be delivered. Preferably, the cationic lipid compounds are biocompatible and biodegradable, and the formed particles are also biodegradable and biocompatible and may be used to provide controlled, sustained release of the agent to be delivered. These and their corresponding particles may also be responsive to pH changes given that these are protonated at lower pH. They may also act as proton sponges in the delivery of an agent to a cell to cause endosome lysis.

In certain embodiments, the cationic lipid compounds are relatively non-cytotoxic. The cationic lipid compounds may be biocompatible and biodegradable. The cationic lipid may have a $pK_a$ in the range of approximately 5.5 to approximately 7.5, more preferably between approximately 6.0 and approximately 7.0. It may be designed to have a desired $pK_a$ between approximately 3.0 and approximately 9.0, or between approximately 5.0 and approximately 8.0. The cationic lipid compounds described herein are particularly attractive for drug delivery for several reasons: they contain amino groups for interacting with DNA, RNA, other polynucleotides, and other negatively charged agents, for buffering the pH, for causing endo-osmolysis, for protecting the agent to be delivered, they can be synthesized from commercially available starting materials; and/or they are pH responsive and can be engineered with a desired $pK_a$.

A composition containing a cationic lipid compound may be 30-70% cationic lipid compound, 0-60% cholesterol, 0-30% phospholipid and 1-10% polyethylene glycol (PEG). Preferably, the composition is 30-40% cationic lipid compound, 40-50% cholesterol, and 10-20% PEG. In other preferred embodiments, the composition is 50-75% cationic lipid compound, 20-40% cholesterol, and 5-10% phospholipid, and 1-10% PEG. The composition may contain 60-70% cationic lipid compound, 25-35% cholesterol, and 5-10% PEG. The composition may contain up to 90% cationic lipid compound and 2-15% helper lipid.

The formulation may be a lipid particle formulation, for example containing 8-30% compound, 5-30% helper lipid, and 0-20% cholesterol; 4-25% cationic lipid, 4-25% helper lipid, 2-25% cholesterol, 10-35% cholesterol-PEG, and 5% cholesterol-amine; or 2-30% cationic lipid, 2-30% helper lipid, 1-15% cholesterol, 2-35% cholesterol-PEG, and 1-20% cholesterol-amine; or up to 90% cationic lipid and 2-10% helper lipids, or even 100% cationic lipid.

Non-Cationic Lipids

The non-cationic lipids that are used in lipid particles can be any of a variety of neutral uncharged, zwitterionic, or anionic lipids capable of producing a stable complex.

Non-limiting examples of non-cationic lipids include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleoyl-phosphatidylglycerol (POPG), dioleoylphosphatidylethanolamine 4-(N-maleimidomethyl)-cyclohexane-1- carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having $C_{10}$-$C_{24}$ carbon chains, e.g., lauroyl, myristoyl, palmitoyl, stearoyl, or oleoyl.

Additional examples of non-cationic lipids include sterols such as cholesterol and derivatives thereof. Non-limiting examples of cholesterol derivatives include polar analogues such as 5α-cholestanol, 5α-coprostanol, cholesteryl-(2'-hydroxy)-ethyl ether, cholesteryl-(4'-hydroxy)-butyl ether, and 6-ketocholestanol; non-polar analogues such as 5α-cholestane, cholestenone, 5α-cholestanone, 5α-cholestanone, and cholesteryl decanoate; and mixtures thereof. In preferred embodiments, the cholesterol derivative is a polar analogue such as cholesteryl-(4'-hydroxy)-butyl ether.

In some embodiments, the non-cationic lipid present in lipid particles comprises or consists of a mixture of one or more phospholipids and cholesterol or a derivative thereof. In other embodiments, the non-cationic lipid present in the lipid particles comprises or consists of one or more phospholipids, e.g., a cholesterol-free lipid particle formulation. In yet other embodiments, the non-cationic lipid present in the lipid particles comprises or consists of cholesterol or a derivative thereof, e.g., a phospholipid-free lipid particle formulation.

Other examples of non-cationic lipids include nonphosphorous containing lipids such as, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, and sphingomyelin.

In some embodiments, the non-cationic lipid comprises from 10 mol % to 60 mol %, from 20 mol % to 55 mol %, from 20 mol % to 45 mol %, 20 mol % to 40 mol %, from 25 mol % to 50 mol %, from 25 mol % to 45 mol %, from 30 mol % to 50 mol %, from 30 mol % to 45 mol %, from 30 mol % to 40 mol %, from 35 mol % to 45 mol %, from 37 mol % to 42 mol %, or 35 mol %, 36 mol %, 37 mol %, 38 mol %, 39 mol %, 40 mol %, 41 mol %, 42 mol %, 43 mol %, 44 mol %, or 45 mol % (or any fraction thereof or range therein) of the total lipid present in the particle.

In embodiments where the lipid particles contain a mixture of phospholipid and cholesterol or a cholesterol derivative, the mixture may comprise up to 40 mol %, 45 mol %, 50 mol %, 55 mol %, or 60 mol % of the total lipid present in the particle.

In some embodiments, the phospholipid component in the mixture may comprise from 2 mol % to 20 mol %, from 2 mol % to 15 mol %, from 2 mol % to 12 mol %, from 4 mol % to 15 mol %, or from 4 mol % to 10 mol % (or any fraction thereof or range therein) of the total lipid present in the particle. In certain preferred embodiments, the phospholipid component in the mixture comprises from 5 mol % to 10 mol %, from 5 mol % to 9 mol %, from 5 mol % to 8 mol %, from 6 mol % to 9 mol %, from 6 mol % to 8 mol %, or 5 mol %, 6 mol %, 7 mol %, 8 mol %, 9 mol %, or 10 mol % (or any fraction thereof or range therein) of the total lipid present in the particle.

In other embodiments, the cholesterol component in the mixture may comprise from 25 mol % to 45 mol %, from 25 mol % to 40 mol %, from 30 mol % to 45 mol %, from 30 mol % to 40 mol %, from 27 mol % to 37 mol %, from 25 mol % to 30 mol %, or from 35 mol % to 40 mol % (or any fraction thereof or range therein) of the total lipid present in the particle. In certain preferred embodiments, the cholesterol component in the mixture comprises from 25 mol % to 35 mol %, from 27 mol % to 35 mol %, from 29 mol % to 35 mol %, from 30 mol % to 35 mol %, from 30 mol % to 34 mol %, from 31 mol % to 33 mol %, or 30 mol %, 31 mol %, 32 mol %, 33 mol %, 34 mol %, or 35 mol % (or any fraction thereof or range therein) of the total lipid present in the particle.

In embodiments where the lipid particles are phospholipid-free, the cholesterol or derivative thereof may comprise up to 25 mol %, 30 mol %, 35 mol %, 40 mol %, 45 mol %, 50 mol %, 55 mol %, or 60 mol % of the total lipid present in the particle.

In some embodiments, the cholesterol or derivative thereof in the phospholipid-free lipid particle formulation may comprise from 25 mol % to 45 mol %, from 25 mol % to 40 mol %, from 30 mol % to 45 mol %, from 30 mol % to 40 mol %, from 31 mol % to 39 mol %, from 32 mol % to 38 mol %, from 33 mol % to 37 mol %, from 35 mol % to 45 mol %, from 30 mol % to 35 mol %, from 35 mol % to 40 mol %, or 30 mol %, 31 mol %, 32 mol %, 33 mol %, 34 mol %, 35 mol %, 36 mol %, 37 mol %, 38 mol %, 39 mol %, or 40 mol % (or any fraction thereof or range therein) of the total lipid present in the particle.

In other embodiments, the non-cationic lipid comprises from 5 mol % to 90 mol %, from 10 mol % to 85 mol %, from 20 mol % to 80 mol %, 10 mol % (e.g., phospholipid only), or 60 mol % (e.g., phospholipid and cholesterol or derivative thereof) (or any fraction thereof or range therein) of the total lipid present in the particle.

The percentage of non-cationic lipid present in the lipid particles is a target amount, and that the actual amount of non-cationic lipid present in the formulation may vary, for example, by ±5 mol %.

Lipid Conjugates

In addition to cationic, the lipid particles described herein may further comprise a lipid conjugate. The conjugated lipid is useful in that it prevents the aggregation of particles. Suitable conjugated lipids include, but are not limited to, PEG-lipid conjugates, cationic-polymer-lipid conjugates, and mixtures thereof.

In a preferred embodiment, the lipid conjugate is a PEG-lipid. Examples of PEG-lipids include, but are not limited to, PEG coupled to dialkyloxypropyls (PEG-DAA), PEG coupled to diacylglycerol (PEG-DAG), PEG coupled to phospholipids such as phosphatidylethanolamine (PEG-PE), PEG conjugated to ceramides, PEG conjugated to cholesterol or a derivative thereof, and mixtures thereof.

PEG is a linear, water-soluble polymer of ethylene PEG repeating units with two terminal hydroxyl groups. PEGs are classified by their molecular weights; and include the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH$_2$), monomethoxypolyethylene glycol-tresylate (MePEG-TRES), monomethoxypolyethylene glycol-imidazolyl-carbonyl (MePEG-IM), as well as such compounds containing a terminal hydroxyl group instead of a terminal methoxy group (e.g., HO-PEG-S, HO-PEG-S-NHS, HO-PEG-NH$_2$).

The PEG moiety of the PEG-lipid conjugates described herein may comprise an average molecular weight ranging from 550 daltons to 10,000 daltons. In certain instances, the PEG moiety has an average molecular weight of from 750 daltons to 5,000 daltons (e.g., from 1,000 daltons to 5,000 daltons, from 1,500 daltons to 3,000 daltons, from 750 daltons to 3,000 daltons, from 750 daltons to 2,000 daltons). In preferred embodiments, the PEG moiety has an average molecular weight of 2,000 daltons or 750 daltons.

In certain instances, the PEG can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester-containing linker moieties and ester-containing linker moieties. In a preferred embodiment, the linker moiety is a non-ester-containing linker moiety. Suitable non-ester-containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—O—), succinyl (—(O)CCH$_2$CH$_2$C(O)—), succinamidyl (—NHC(O)CH$_2$CH$_2$C(O)NH—), ether, disulphide, as well as combinations thereof (such as a linker containing both a carbamate linker moiety and an amido linker moiety). In a preferred embodiment, a carbamate linker is used to couple the PEG to the lipid.

In other embodiments, an ester-containing linker moiety is used to couple the PEG to the lipid. Suitable ester-containing linker moieties include, e.g., carbonate (—OC(O)O—), succinoyl, phosphate esters (—O—(O)POH—O—), sulfonate esters, and combinations thereof.

Phosphatidylethanolamines having a variety of acyl chain groups of varying chain lengths and degrees of saturation can be conjugated to PEG to form the lipid conjugate. Such phosphatidylethanolamines are commercially available, or can be isolated or synthesized using conventional techniques known to those of skill in the art. Phosphatidylethanolamines containing saturated or unsaturated fatty acids with carbon chain lengths in the range of $C_{10}$ to $C_{20}$ are preferred. Phosphatidylethanolamines with mono- or di-unsaturated fatty acids and mixtures of saturated and unsaturated fatty acids can also be used. Suitable phosphatidylethanolamines include, but are not limited to, dimyristoyl-phosphatidylethanolamine (DMPE), dipalmitoyl-phosphatidylethanolamine (DPPE), dioleoyl-phosphatidylethanolamine (DOPE), and distearoyl-phosphatidylethanolamine (DSPE).

The term "diacylglycerol" or "DAG" includes a compound having 2 fatty acyl chains, $R^1$ and $R^2$, both of which have independently between 2 and 30 carbons bonded to the 1- and 2-position of glycerol by ester linkages. The acyl groups can be saturated or have varying degrees of unsaturation. Suitable acyl groups include, but are not limited to, lauroyl ($C_{12}$), myristoyl ($C_{14}$), palmitoyl ($C_{16}$), stearoyl ($C_{18}$), and icosoyl ($C_{20}$). In preferred embodiments, $R^1$ and $R^2$ are the same, i.e., $R^1$ and $R^2$ are both myristoyl (i.e., dimyristoyl), $R^1$ and $R^2$ are both stearoyl (i.e., distearoyl).

The term "dialkyloxypropyl" or "DAA" includes a compound having 2 alkyl chains, R and R, both of which have independently between 2 and 30 carbons. The alkyl groups can be saturated or have varying degrees of unsaturation.

Preferably, the PEG-DAA conjugate is a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, or a PEG-distearyloxypropyl ($C_{18}$) conjugate. In these embodiments, the PEG preferably has an average molecular weight of 750 or 2,000 daltons. In particular embodiments, the terminal hydroxyl group of the PEG is substituted with a methyl group.

In addition to the foregoing, other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl methacrylamide, polymethacrylamide and polydimethylacrylamide, polylactic acid, polyglycolic acid, and derivatized celluloses such as hydroxymethylcellulose or hydroxyethylcellulose.

In some embodiments, the lipid conjugate (e.g., PEG-lipid) comprises from 0.1 mol % to 2 mol %, from 0.5 mol % to 2 mol %, from 1 mol % to 2 mol %, from 0.6 mol % to 1.9 mol %, from 0.7 mol % to 1.8 mol %, from 0.8 mol % to 1.7 mol %, from 0.9 mol % to 1.6 mol %, from 0.9 mol % to 1.8 mol %, from 1 mol % to 1.8 mol %, from 1 mol % to 1.7 mol %, from 1.2 mol % to 1.8 mol %, from 1.2 mol % to 1.7 mol %, from 1.3 mol % to 1.6 mol %, or from 1.4 mol % to 1.5 mol % (or any fraction thereof or range therein) of the total lipid present in the particle. In other embodiments, the lipid conjugate (e.g., PEG-lipid) comprises from 0 mol % to 20 mol %, from 0.5 mol % to 20 mol %, from 2 mol % to 20 mol %, from 1.5 mol % to 18 mol %, from 2 mol % to 15 mol %, from 4 mol % to 15 mol %, from 2 mol % to 12 mol %, from 5 mol % to 12 mol %, or 2 mol % (or any fraction thereof or range therein) of the total lipid present in the particle.

In further embodiments, the lipid conjugate (e.g., PEG-lipid) comprises from 4 mol % to 10 mol %, from 5 mol % to 10 mol %, from 5 mol % to 9 mol %, from 5 mol % to 8 mol %, from 6 mol % to 9 mol %, from 6 mol % to 8 mol %, or 5 mol %, 6 mol %, 7 mol %, 8 mol %, 9 mol %, or 10 mol % (or any fraction thereof or range therein) of the total lipid present in the particle.

The percentage of lipid conjugate (e.g., PEG-lipid) present in the lipid particles of the invention is a target amount, and the actual amount of lipid conjugate present in the formulation may vary, for example, by ±2 mol %. One of ordinary skill in the art will appreciate that the concentration of the lipid conjugate can be varied depending on the lipid conjugate employed and the rate at which the lipid particle is to become fusogenic.

By controlling the composition and concentration of the lipid conjugate, one can control the rate at which the lipid conjugate exchanges out of the lipid particle and, in turn, the rate at which the lipid particle becomes fusogenic. In addition, other variables including, e.g., pH, temperature, or ionic strength, can be used to vary and/or control the rate at which the lipid particle becomes fusogenic. Other methods which can be used to control the rate at which the lipid particle becomes fusogenic will become apparent to those of skill in the art upon reading this disclosure. Also, by controlling the composition and concentration of the lipid conjugate, one can control the lipid particle size.

Compositions and Formulations for Administration

The nucleic acid-lipid compositions of this disclosure may be administered by various routes, for example, to effect systemic delivery via intravenous, parenteral, intraperitoneal, or topical routes. In some embodiments, a siRNA may be delivered intracellularly, for example, in cells of a target tissue such as lung or liver, or in inflamed tissues. In some embodiments, this disclosure provides a method for delivery of siRNA in vivo. A nucleic acid-lipid composition may be administered intravenously, subcutaneously, or intraperitoneally to a subject. In some embodiments, the disclosure provides methods for in vivo delivery of interfering RNA to the lung of a mammalian subject.

In some embodiments, this disclosure provides a method of treating a disease or disorder in a mammalian subject. A therapeutically effective amount of a composition of this disclosure containing a nucleic, a cationic lipid, an amphiphile, a phospholipid, cholesterol, and a PEG-linked cholesterol may be administered to a subject having a disease or disorder associated with expression or overexpression of a gene that can be reduced, decreased, downregulated, or silenced by the composition.

The compositions and methods of the disclosure may be administered to subjects by a variety of mucosal administration modes, including by oral, rectal, vaginal, intranasal, intrapulmonary, or transdermal or dermal delivery, or by topical delivery to the eyes, ears, skin, or other mucosal surfaces. In some aspects of this disclosure, the mucosal tissue layer includes an epithelial cell layer. The epithelial cell can be pulmonary, tracheal, bronchial, alveolar, nasal, buccal, epidermal, or gastrointestinal. Compositions of this disclosure can be administered using conventional actuators such as mechanical spray devices, as well as pressurized, electrically activated, or other types of actuators.

Compositions of this disclosure may be administered in an aqueous solution as a nasal or pulmonary spray and may be dispensed in spray form by a variety of methods known to those skilled in the art. Pulmonary delivery of a composition of this disclosure is achieved by administering the composition in the form of drops, particles, or spray, which can be, for example, aerosolized, atomized, or nebulized. Particles of the composition, spray, or aerosol can be in either a liquid or solid form. Such formulations may be conveniently prepared by dissolving compositions according to the present disclosure in water to produce an aqueous solution, and rendering said solution sterile. The formulations may be presented in multi-dose containers. Additional aerosol delivery forms may include, e.g., compressed air-, jet-, ultrasonic-, and piezoelectric nebulizers, which deliver the biologically active agent dissolved or suspended in a pharmaceutical solvent, e.g., water, ethanol, or mixtures thereof.

Nasal and pulmonary spray solutions of the present disclosure typically comprise the drug or drug to be delivered, optionally formulated with a surface active agent, such as a nonionic surfactant (e.g., polysorbate-80), and one or more buffers. In some embodiments of the present disclosure, the nasal spray solution further comprises a propellant. The pH of the nasal spray solution may be from pH 6.8 to 7.2. The pharmaceutical solvents employed can also be a slightly acidic aqueous buffer of pH 4-6. Other components may be added to enhance or maintain chemical stability, including preservatives, surfactants, dispersants, or gases.

In some embodiments, this disclosure is a pharmaceutical product which includes a solution containing a composition of this disclosure and an actuator for a pulmonary, mucosal, or intranasal spray or aerosol.

A dosage form of the composition of this disclosure can be liquid, in the form of droplets or an emulsion, or in the form of an aerosol.

A dosage form of the composition of this disclosure can be solid, which can be reconstituted in a liquid prior to administration. The solid can be administered as a powder. The solid can be in the form of a capsule, tablet, or gel.

To formulate compositions for pulmonary delivery within the present disclosure, the biologically active agent can be combined with various pharmaceutically acceptable additives, as well as a base or carrier for dispersion of the active agent(s). Examples of additives include pH control agents such as arginine, sodium hydroxide (NaOH), glycine, hydrochloric acid (HCl), citric acid, and mixtures thereof. Other additives include local anesthetics (e.g., benzyl alcohol), isotonizing agents (e.g., sodium chloride (NaCl), mannitol, sorbitol), adsorption inhibitors (e.g., Tween 80), solubility enhancing agents (e.g., cyclodextrins and derivatives thereof), stabilizers (e.g., serum albumin), and reducing agents (e.g., glutathione). When the composition for mucosal delivery is a liquid, the tonicity of the formulation, as measured with reference to the tonicity of 0.9% (w/v) physiological saline solution taken as unity, is typically adjusted to a value at which no substantial, irreversible tissue damage will be induced in the mucosa at the site of administration. Generally, the tonicity of the solution is adjusted to a value of ⅓ to 3, more typically ½ to 2, and most often ¾ to 1.7.

The biologically active agent may be dispersed in a base or vehicle, which may comprise a hydrophilic compound having a capacity to disperse the active agent and any desired additives. The base may be selected from a wide range of suitable carriers, including but not limited to, copolymers of polycarboxylic acids or salts thereof, carboxylic anhydrides (e.g., maleic anhydride) with other monomers (e.g., methyl(meth)acrylate, acrylic acid, etc.), hydrophilic vinyl polymers such as polyvinyl acetate, polyvinyl alcohol, polyvinylpyrrolidone, cellulose derivatives such as hydroxymethylcellulose, hydroxypropylcellulose, etc., and natural polymers such as chitosan, collagen, sodium alginate, gelatin, hyaluronic acid, and nontoxic metal salts thereof. Often, a biodegradable polymer is selected as a base or carrier, for example, polylactic acid, poly(lactic acid-glycolic acid) copolymer, polyhydroxybutyric acid, poly (hydroxybutyric acid-glycolic acid) copolymer, and mixtures thereof. Alternatively or additionally, synthetic fatty acid esters such as polyglycerin fatty acid esters, sucrose fatty acid esters, etc., can be employed as carriers. Hydrophilic polymers and other carriers can be used alone or in combination, and enhanced structural integrity can be imparted to the carrier by partial crystallization, ionic bonding, crosslinking, and the like. The carrier can be provided in a variety of forms, including fluid or viscous solutions, gels, pastes, powders, microspheres, and films for direct application to the nasal mucosa. The use of a selected carrier in this context may result in promotion of absorption of the biologically active agent.

Formulations for mucosal, nasal, or pulmonary delivery may contain a hydrophilic low molecular weight compound as a base or excipient. Such hydrophilic low molecular weight compounds provide a passage medium through which a water-soluble active agent, such as a physiologically active peptide or protein, may diffuse through the base to the body surface where the active agent is absorbed. The hydrophilic low molecular weight compound optionally absorbs moisture from the mucosa or the administration atmosphere and dissolves the water-soluble active peptide. The molecular weight of the hydrophilic low molecular weight compound is generally not more than 10,000 and preferably not more than 3,000. Examples of hydrophilic low molecular weight compounds include polyol compounds, such as oligo-, di- and monosaccarides including sucrose, mannitol, lactose, L-arabinose, D-erythrose, D-ribose, D-xylose, D-mannose, D-galactose, lactulose, cellobiose, gentibiose, glycerin, polyethylene glycol, and mixtures thereof. Further examples of hydrophilic low molecular weight compounds include N-methylpyrrolidone, alcohols (e.g., oligovinyl alcohol, ethanol, ethylene glycol, propylene glycol, etc.), and mixtures thereof.

The compositions of this disclosure may alternatively contain as pharmaceutically acceptable carriers substances as required to approximate physiological conditions, such as pH adjusting and buffering agents, tonicity adjusting agents, and wetting agents, for example, sodium acetate, sodium lactate, NaCl, potassium chloride, calcium chloride, sorbitan monolaurate, triethanolamine oleate, and mixtures thereof. For solid compositions, conventional nontoxic pharmaceutically acceptable carriers can be used which include, for example, pharmaceutical grades of mannitol, lactose, starch, magnesium stearate, sodium saccharin, talcum, cellulose, glucose, sucrose, magnesium carbonate, and the like.

In certain embodiments of the disclosure, the biologically active agent may be administered in a time release formulation, for example in a composition which includes a slow release polymer. The active agent can be prepared with carriers that will protect against rapid release, for example a controlled release vehicle such as a polymer, microencapsulated delivery system, or bioadhesive gel. Prolonged delivery of the active agent, in various compositions of the disclosure can be brought about by including in the composition agents that delay absorption, for example, aluminum monostearate hydrogels and gelatin.

While this disclosure has been described in relation to certain embodiments, and many details have been set forth for purposes of illustration, it will be apparent to those skilled in the art that this disclosure includes additional embodiments, and that some of the details described herein may be varied considerably without departing from this disclosure. This disclosure includes such additional embodiments, modifications, and equivalents. In particular, this disclosure includes any combination of the features, terms, or elements of the various illustrative components and examples.

EXAMPLES

Example 1

Unless otherwise mentioned. All starting materials were commercially available research-grade chemicals and used without further purification. All reactions are monitored by thin-layer chromatography (TLC), on 0.25 mm silica gel plates (60F254), and visualized with UV lamp, $KMnO_4$ solution. Reaction mixtures are stirred magnetically. 1H NMR spectra are recorded on Bruker 400 MHz spectrometer. The chemical shifts values are expressed in ppm related to tetramethylsilane as internal standard. Mass spectra were determined on an Agilent technologies-Ion-trap mass spectrometer-LC-MSD TRAPXCT PLUS. Flash column chromatography is carried out using Merck silica gel 230-400 mesh.

Chromatography was done on hand packed columns. Silica gel was wetted with non-polar solvent used for elution prior to packing. Elutions were gradient and details of gradient are given at each step.

The following lipids 11, 13, 14, 15, 16, 17, 18, 19, and 20 were synthesized.

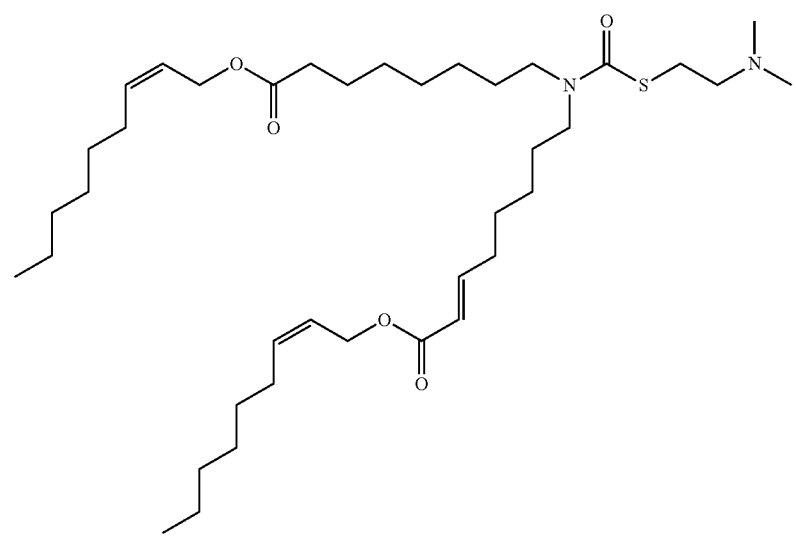

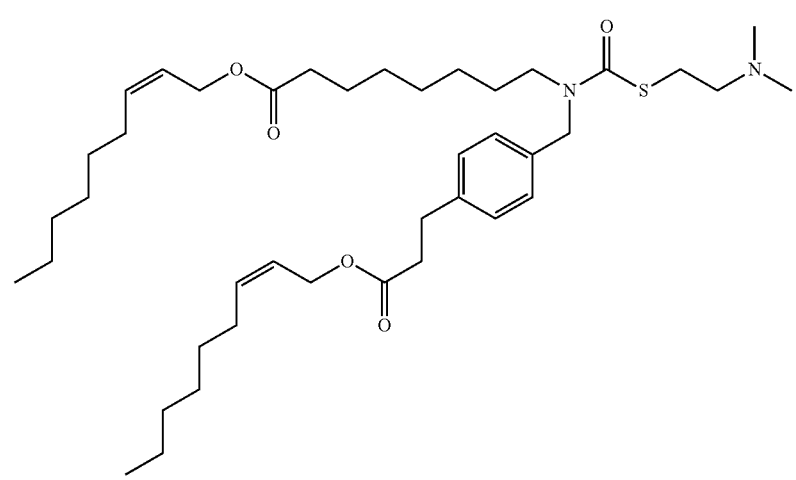

-continued
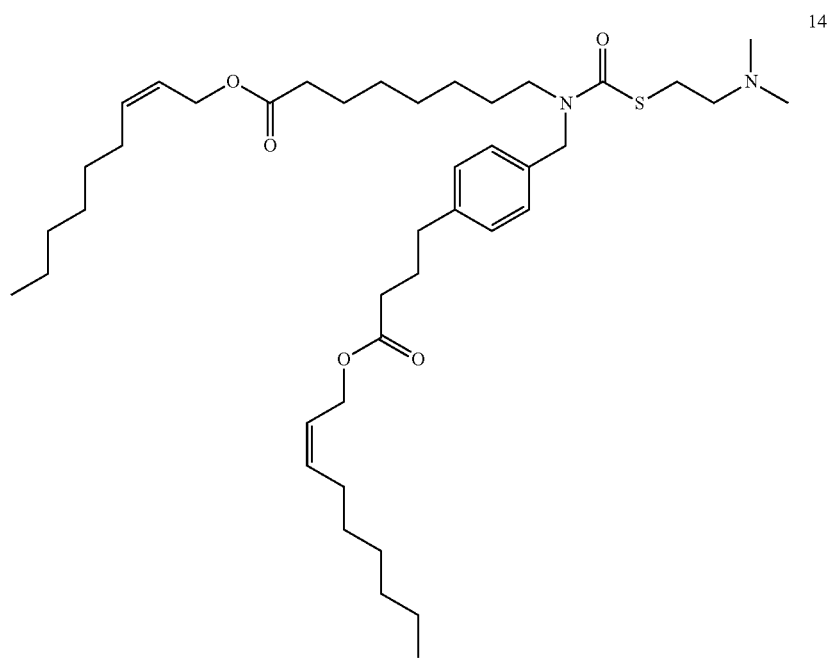
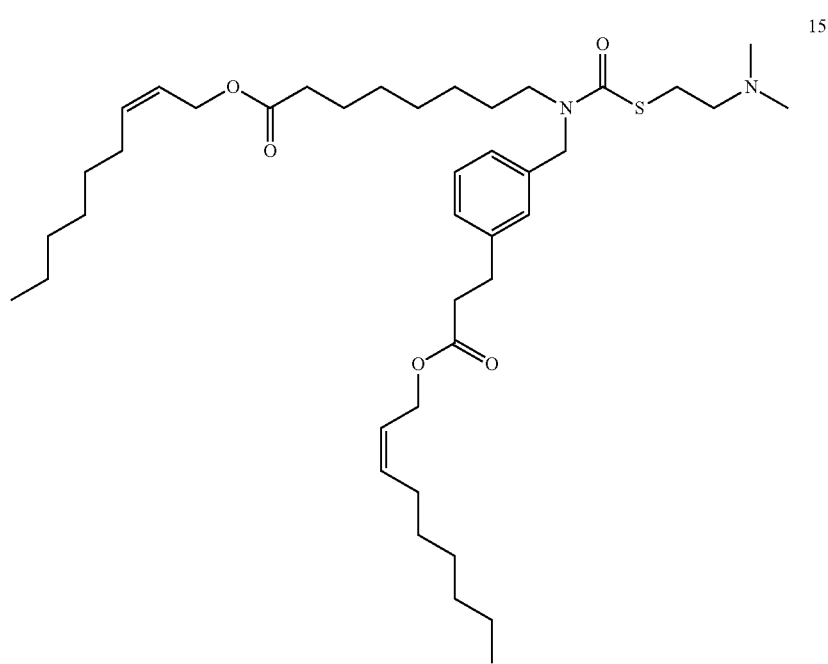

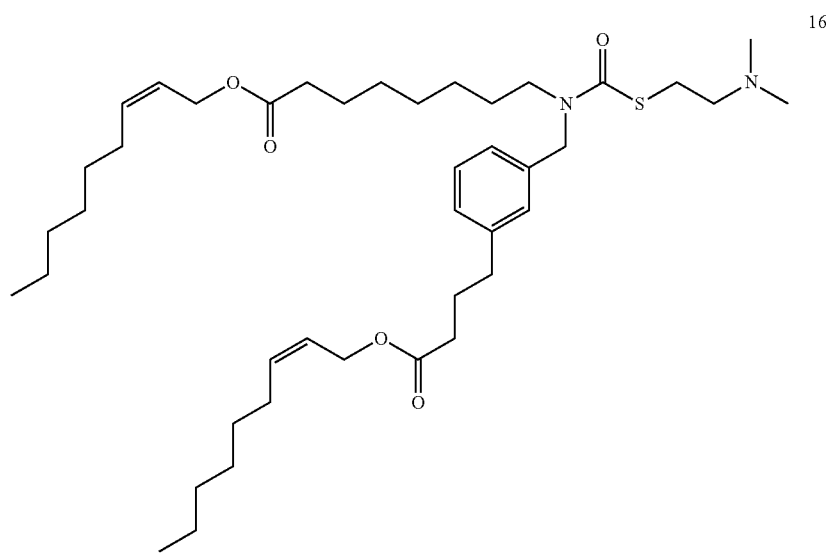
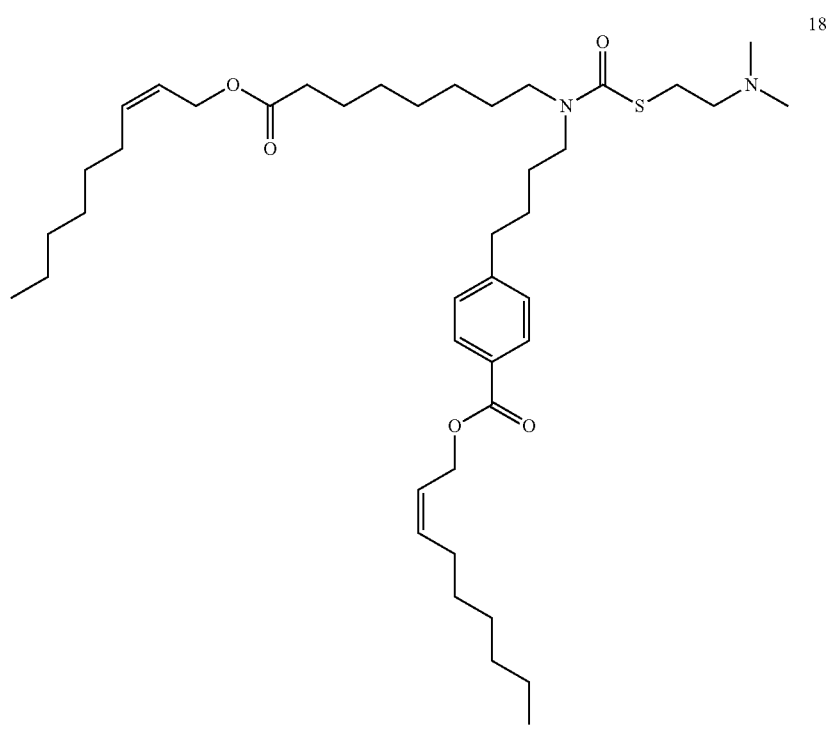

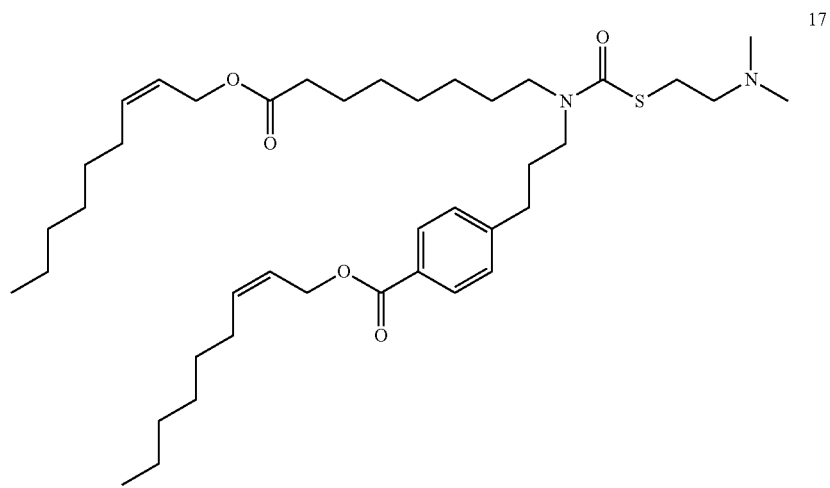
17
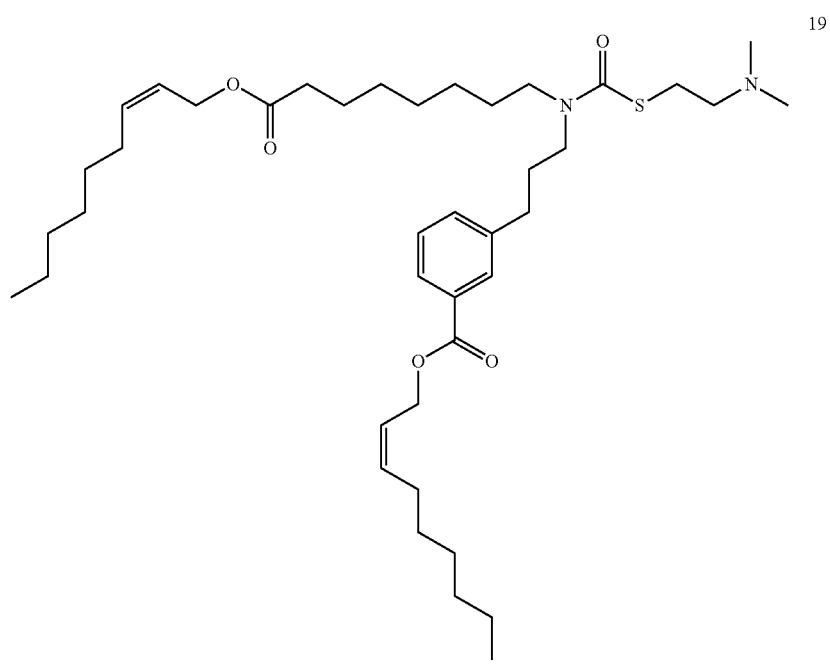
19
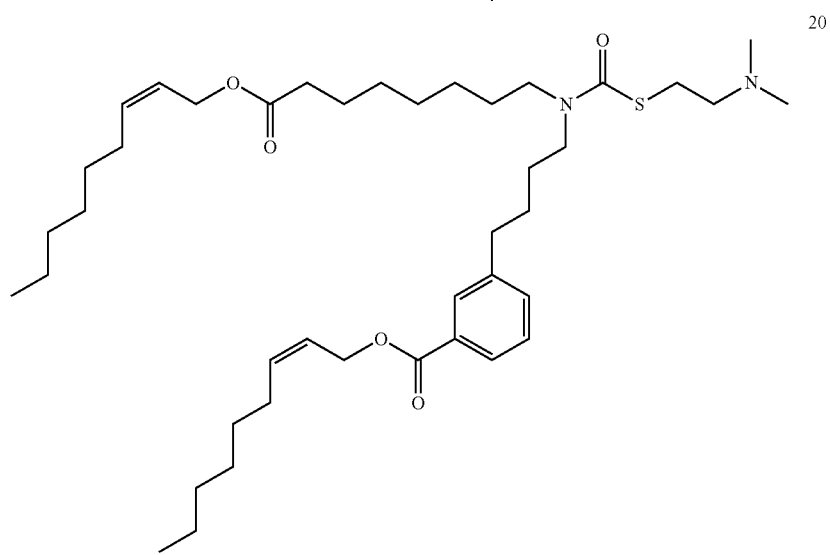
20

Example 2: Synthesis of Lipid 11

Lipid 11 was synthesized in six steps as shown in FIG. 1.

Lipid 11: Step 1

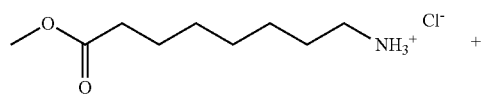

11-1

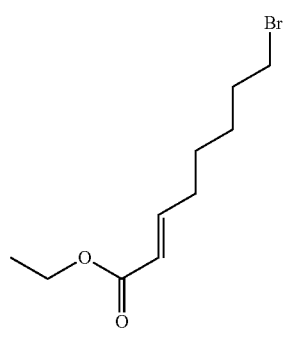

11-2

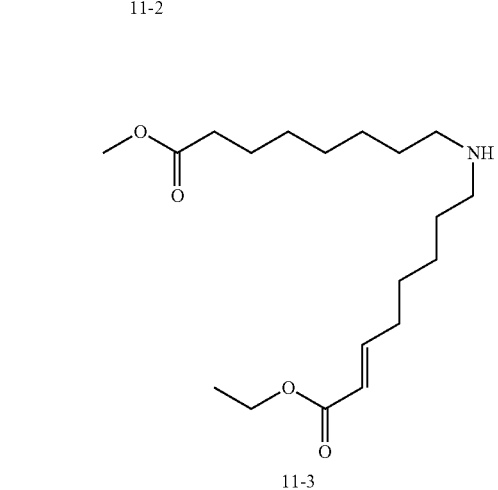

11-3

To a suspension of 7.0 g 8-amino-octanoic acid methyl ester hydrochloride 11-1 (1 eq.) in acetonitrile (ACN; 70 ml), 13.6 g K2CO3 (3 eq.) was added portion-wise at 25° C. and stirred for 15 minutes. To the above reaction mixture, 8.2 g (E)-8-bromo-oct-2-enoic acid ethyl ester 11-2 (1 eq.) was added drop-wise and stirred at room temperature for 16 hours.

Reaction conversion was monitored by thin layer chromatography (TLC), dichloromethane:methanol (DCM:MeOH), 9.5:0.5.

After completion of the reaction, reaction mass was diluted with 20% MeOH in DCM, stirred for 20 minutes, the $K_2CO_3$ was filtered off. Filtrate from above was concentrated under reduced pressure at 50-55° C. to get crude product was purified by silica gel (60-120 mesh) column chromatography (0.5 to 3% MeOH in DCM) to obtain product 11-3 as a pale yellow liquid yield. Quantity produced, 7 g; yield, 35%; confirmed by $^1$H NMR and LC-MS.

Lipid 11: Step-2

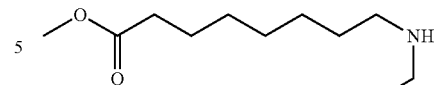

11-3

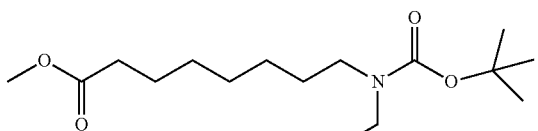

11-4

To a solution of 6 g (E)-8-(7-methoxycarbonyl-heptylamino)-oct-2-enoic acid ethyl ester 11-3 (1 eq.) in 1,4-dioxane (60 ml), $Na_2CO_3$ (10% aq, 60 ml) was added at 25° C. The resulting suspension was cooled to 0-5° C., 4.7 ml Boc anhydride (1.2 eq.) was added drop wise for 5 minutes and the reaction was stirred for 16 hours at room temperature.

Reaction monitored by TLC using hexane:ethyl acetate (EtOAc), 2:3, v:v.

After completion of reaction, reaction mass was concentrated at 50-55° C., then diluted with $H_2O$ and extracted with EtOAc. The organic layer concentrated under reduced pressure to get crude product which was purified by silica gel (230-400 mesh) flash column chromatography (3-15% EtOAc in petroleum (pet) ether) to obtain (E)-8-(tert-butoxycarbonyl-(7-methoxycarbonyl-heptyl)-amino)-oct-2-enoic acid ethyl ester 11-4 as pale yellow oil. Quantity produced, 6 g; yield, 77%; confirmed by $^1$H NMR and LC-MS.

Lipid 11: Step-3

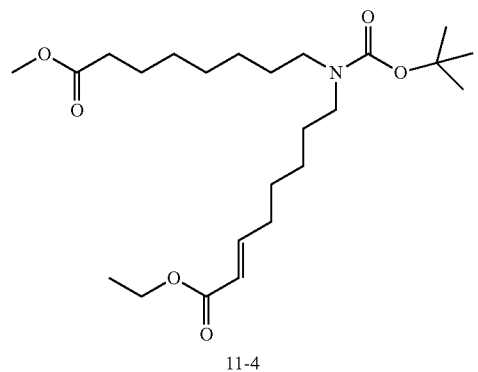

11-4

Step-3

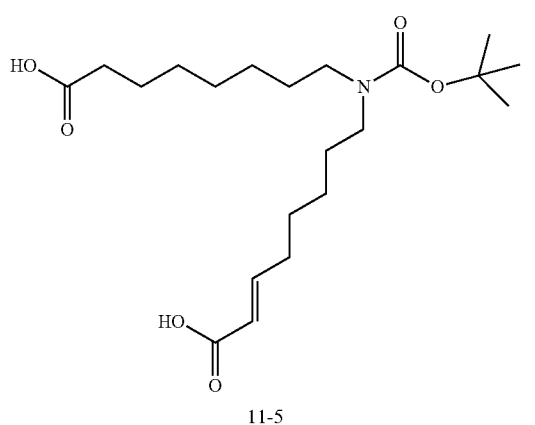

11-5

Lipid 11: Step-4

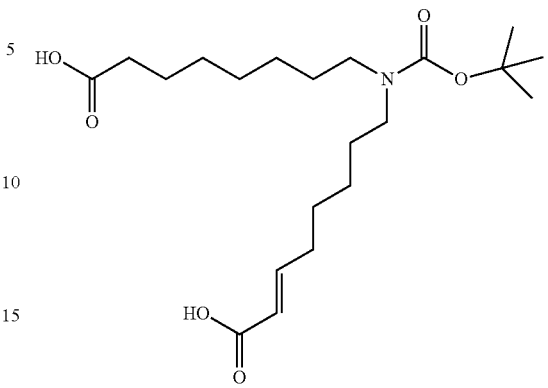

11-5

+

HO⏜⏜⏜⏜

11-6

Step-4

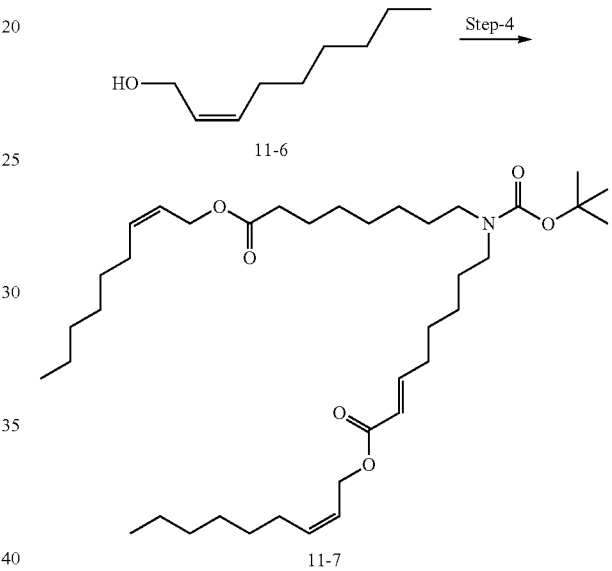

11-7

To a solution of 6 g (E)-8-(tert-butoxycarbonyl-(7-methoxycarbonyl-heptyl)-amino)-oct-2-enoic acid ethyl ester (1 eq.) in MeOH at 0-5° C., 3.26 g NaOH (3 eq.) in H$_2$O (30 ml) was added drop wise and the resulting suspension was stirred at 25-30° C. for 6 hours.

Reaction completion was monitored by TLC using hexane:EtOAc, 2:3, v:v.

After completion of reaction, reaction mass was concentrated under reduced pressure, the residue obtained was acidified with aqueous 1.5 N HCl to pH 3-4 and extracted with EtOAc. Organic layer dried over anhydrous Na$_2$SO$_4$ and concentrated at 50° C. to get (E)-8-[tert-butoxycarbonyl-(7-carboxy-heptyl)-amino]-oct-2-enoic acid (11.5) as an off white solid. Quantity produced, 5.2 g; yield, 95%; confirmed by $^1$H NMR and LC-MS.

To a solution of 5 g (E)-8-[tert-butoxycarbonyl-(7-carboxy-heptyl)-amino]-oct-2-enoic acid (11.5; 1 eq.) in DCM (50 ml) at 0° C., 610 mg dimethylaminopyridine (DMAP; 0.4 eq.), 13 ml N,N-diisopropylethylamine (DIPEA; 6 eq.) and 14.3 g 1-ethyl-3-(3-dimethylaminopropyl)carbodiimide hydrochloride salt (EDC.HCl; 6 eq.) were added successively at 0° C. for 10 minute. To this solution 5.2 g (Z)-non-2-en-1-ol (11-6) (3 eq.) was added in one lot and the reaction mixture was stirred at 25° C. for 16 hours.

Reaction completion was monitored by TLC using hexane:EtOAc, 2:3 v:v.

After completion of the reaction, reaction mixture was quenched with H$_2$O and product was extracted with DCM. The organic layer dried over Na$_2$SO$_4$, concentrated under reduced pressure at 50° C. the crude product was purified by silica gel (230-400 mesh) flash column chromatography (2-8% EtOAc in pet ether) to obtain (E)-8-(tert-butoxycarbonyl-(7-(((Z)-non-2-enyl)oxycarbonyl)-heptyl)-amino)-oct-2-enoic acid (Z)-non-2-enyl ester (11-7) as pale yellow liquid. Quantity produced, 5.2 g; yield, 65%; confirmed by $^1$H NMR and LC-MS.

Lipid 11: Step 5

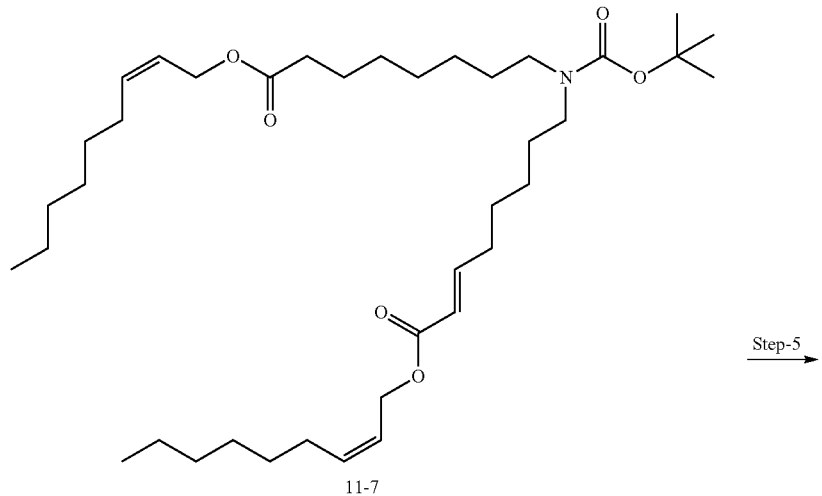

11-7

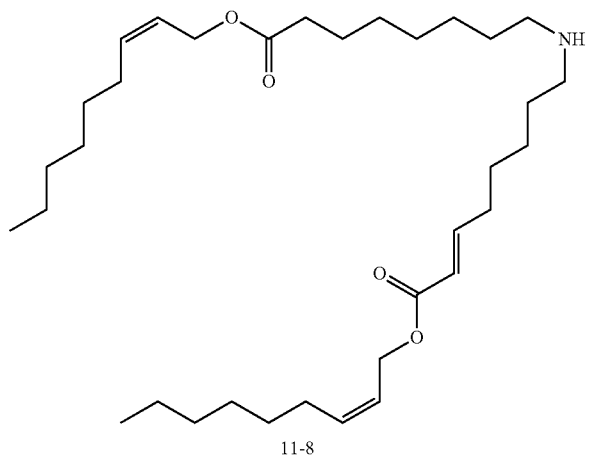

11-8

To a solution of 4 g (E)-8-(tert-butoxycarbonyl-(7-(((Z)-non-2-enyl)oxycarbonyl)-heptyl)-amino)-oct-2-enoic acid (Z)-non-2-enyl ester (11-7, 1 eq.) in DCM (40 ml) at 0-5° C., trifluoroacetic acid (TFA; 5 eq.) was added drop wise and stirred the reaction mixture at room temperature for 1 hour.

Reaction was monitored by TLC using hexane:EtOAc, 2:3 v:v.

The reaction mass was concentrated after completion of the reaction. The residue obtained was made basic with 10% aqueous s $Na_2CO_3$ solution and product was extracted with EtOAc (2×20 volumes). The organic layer obtained from above dried over anhydrous $Na_2SO_4$, concentrated under reduced pressure at 50° C. the residue was purified by silica gel flash column chromatography (230-400 mesh) (5-15% EtOAc in pet ether) to obtain (E)-8-(7-(((Z)-Non-2-enyl) oxycarbonyl)-heptylamino)-oct-2-enoic acid (Z)-non-2-enyl ester (11-8) (11.8) as a pale yellow liquid. Quantity produced, 3.1 g; yield, 91%; confirmed by $^1H$ NMR and LC-MS.

Lipid 11: Step 6

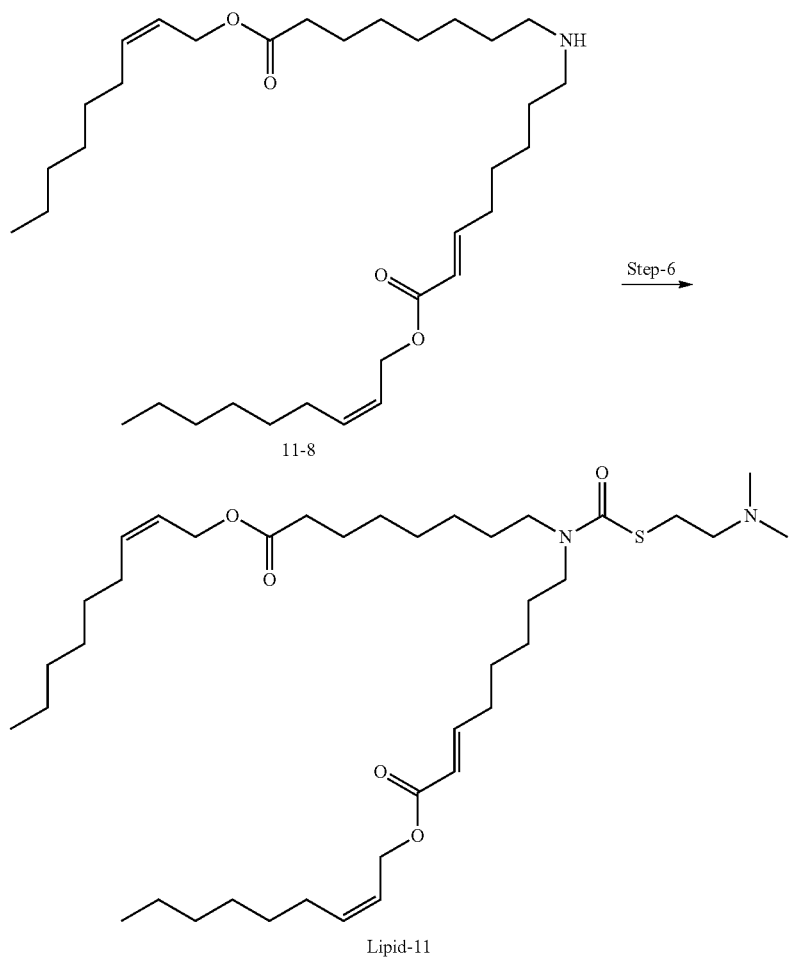

To solution of 6 g (E)-8-(7-(((Z)-non-2-enyl)oxycarbonyl)-heptylamino)-oct-2-enoic acid (Z)-non-2-enyl ester 11-8 (11.8; 1 eq.) in DCM at 0-5° C., 2.92 g triphosgene (0.9 eq.) was added in two portions. To the above at same temperature 2.9 ml triethylamine (TEA; 2 eq.) was added drop wise and stirred for 30 minutes at 25° C.

Completion of reaction was monitored by TLC-1 using hexane:EtOAc, 2:3, v:v.

Reaction mass was concentrated under reduced pressure. The residue obtained was diluted with DCM and was cooled to 0-5° C. N,N-dimethyl ethane thiol hydrochloride, 7.6 g (5 eq.) and 12.1 ml TEA (8 eq.) were added successively and stirred at 25-30° C. for 16 hour.

Completion of reaction was monitored by TLC, using 100% EtOAc.

The product was quenched with $H_2O$ and product was extracted with EtOAc. The organic layer obtained from above dried over anhydrous $Na_2SO_4$, concentrated under reduced pressure at 50° C. the residue was purified by silica gel flash (230-400 mesh) column chromatography (0-4% MeOH in DCM) to obtain Lipid 11 as a pale yellow liquid. Quantity produced, 1 g; yield, 13.4%; confirmed by $^1H$ NMR and LC-MS; HPLC purity 94.27%.

1H-NMR, Lipid 11 (400 MHz, CDCl3) δ=6.95 (dm, J=15.0, 1), 6.81 (d, J=15.0, 1), 5.65 (m, 2), 5.52 (m, 2), 4.68 (d, J=6.8, 2), 4.62 (d, J=6.8, 2), 3.18-3.36 (4), 3.04 (t, J=7.0, 2), 2.58 (m, 2), 2.31 (s, 6), 2.25-2.41 (2), 2.00-2.25 (8), 1.20-1.60 (30), 0.82-0.91 (6).

Example 2. Synthesis of Lipid 13

Figure 2:
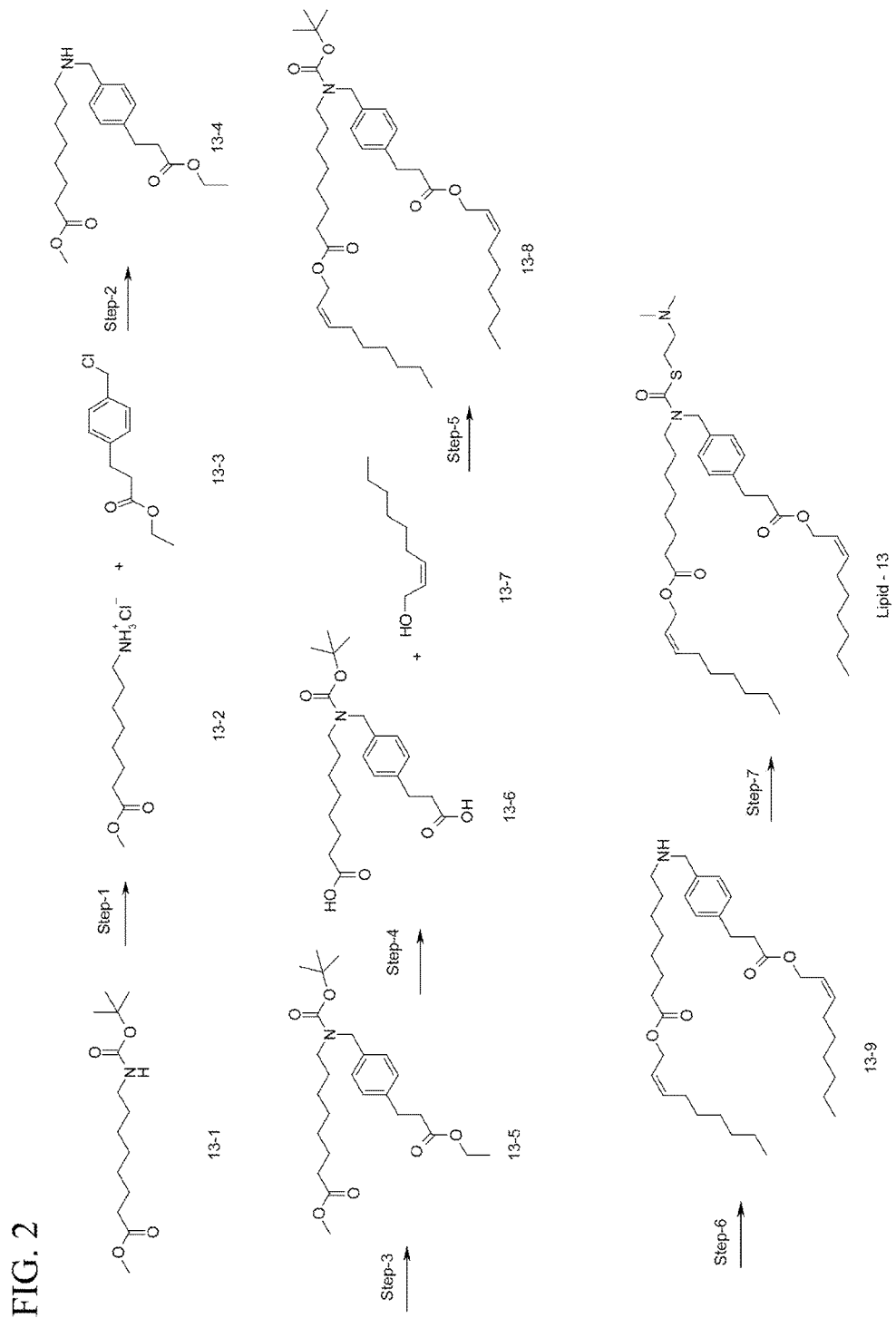
FIG. 2 shows the preparation of Lipid 13, showing intermediates 13-1 to 13-9. 13-1, 13-3, and 13-7 are commercial starting materials. The reactions are described in detail in Example 3.

Lipid 13 was synthesized in seven steps as shown in FIG. 2.

Lipid 13: Step 1

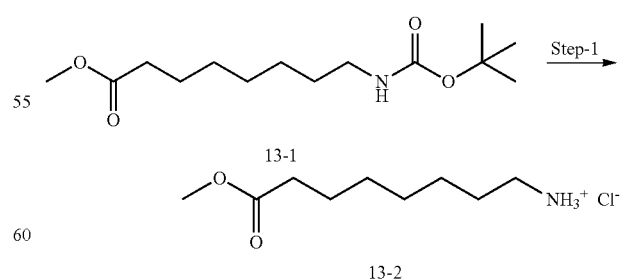

To a solution of 50.0 g compound 13-1 in 1,4-dioxane (100 ml) was added 2 N HCl in 1,4-dioxane (500 ml) at 0° C. The reaction mixture was stirred at room temperature over 12 hours.

Completion of reaction was monitored by TLC, MeOH:DCM, 2:8, v:v.

Diethyl ether was added to the reaction mixture to get off white precipitate. The precipitate formed was stirred for 10 minutes and filtered, affording compound 13-2, as an off-white solid. Quantity produced, 35.0 g; yield, 92%; confirmed by ¹H NMR and LC-MS.

Lipid 13: Step-2

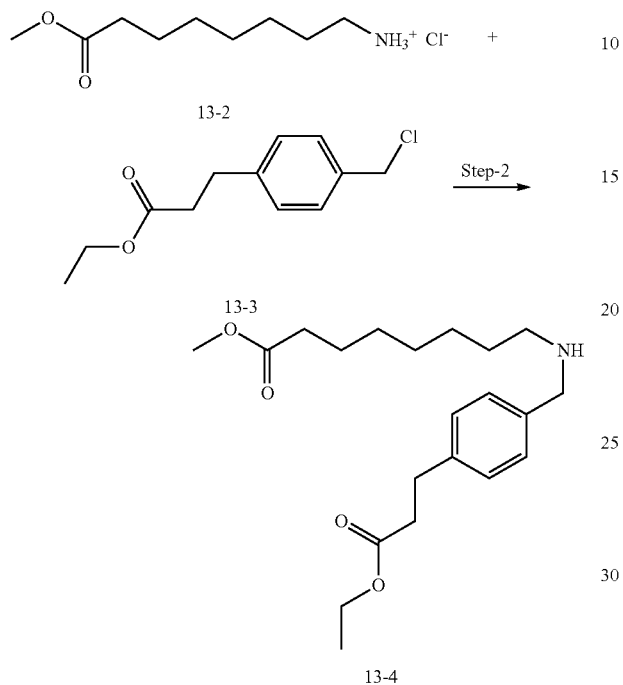

To a solution of 10.0 g amine hydrochloride 13-2 (1 eq.) in ACN (100 ml), were added 19.80 g anhydrous K₂CO₃ (3 eq.) and 13.6 g compound 13-3 (1 eq.) at room temperature. The reaction mixture was stirred at room temperature for 16 hours.

Completion of reaction was monitored by TLC, MeOH:DCM, 1:9, v:v. Starting material 13-2 was observed to be absent.

Resulting reaction mixture was diluted with EtOAc (1000 ml), washed with H₂O (2×100 ml), and concentrated. The crude product obtained upon evaporation of volatiles was purified by silica gel (230-400 mesh) flash column chromatography (0-4% MeOH in DCM) to obtain product 13-4 as a pale yellow oil. Quantity produced, 7.0 g; yield, 42%; confirmed by ¹H NMR and LC-MS.

Lipid 13: Step-3:

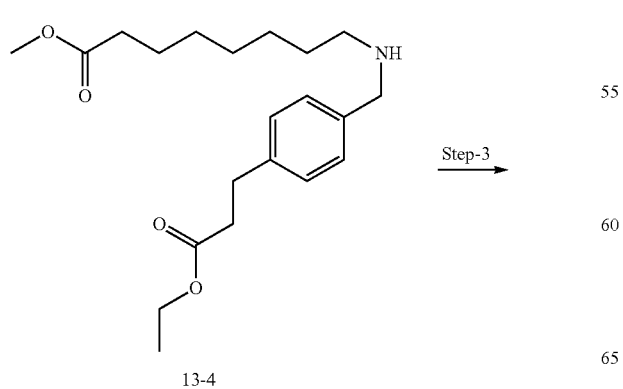

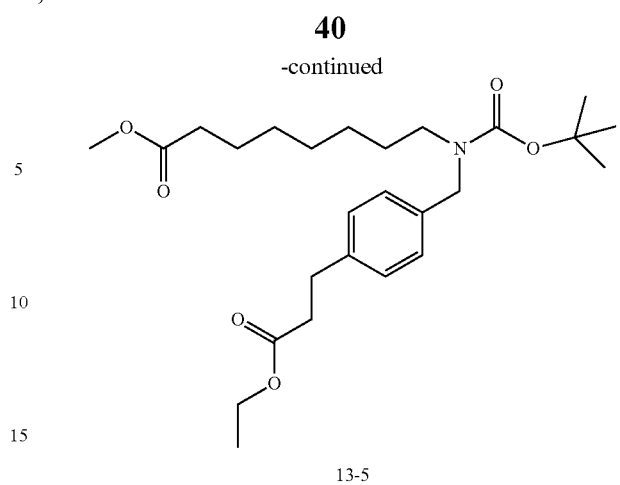

To a solution of 6.0 g compound 13-4 (1 eq.) in a 1:1 mixture of 1,4-dioxane:H₂O (50 ml) were added 7.19 g (BOC)₂O (1.2 eq.) and 3.46 g NaHCO₃ (3 eq.) at room temperature. The resulting reaction mixture was stirred at room temperature for 12 hours.

Reaction monitored by TLC, EtOAc:hexane, 2:8, v:v. Starting material 13-4 was observed to be absent.

Reaction mixture was diluted with EtOAc (500 ml), washed with H₂O (2×100 ml) and organic layer was concentrated under reduced pressure. The residue obtained was purified by silica gel (230-400 mesh) flash column chromatography (5-15% EtOAc in pet ether) to obtain product 13-5 as a pale yellow oil. Quantity produced 6.0 g; yield, 82%; confirmed by ¹H NMR and LC-MS.

Lipid 13: Step-4:

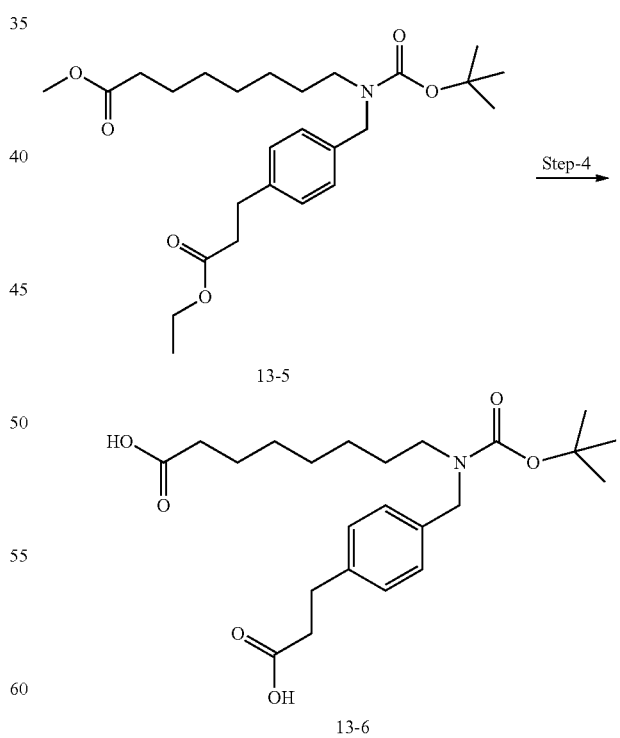

To a solution of compound 6.0 g 13-5 (1 eq.) in a mixture of MeOH:H₂O, 4:1 (50 ml) was added 1.29 g NaOH (3 eq.) at room temperature. The reaction mixture was stirred at room temperature for 16 hours.

Completion of reaction was monitored by TLC, MeOH:DCM, 1:9. Starting material 13-5 was observed to be absent.

MeOH was evaporated under reduced pressure. Crude reaction mixture was diluted with H₂O (50 ml), neutralized with 0.1 N HCl. Then aqueous layer was extracted with EtOAc (3×100 ml), the combined organic layer was washed with H₂O (250 ml), dried over anhydrous Na₂SO₄ and concentrated under reduced pressure. The residue was purified by silica gel flash (60-120) column chromatography (0.5-3% MeOH in DCM) to obtain product 13-6 as pale yellow oil. Quantity produced, 5.2 g; yield, 95%; confirmed by ¹H NMR and LC-MS.

Lipid 13: Step-5:

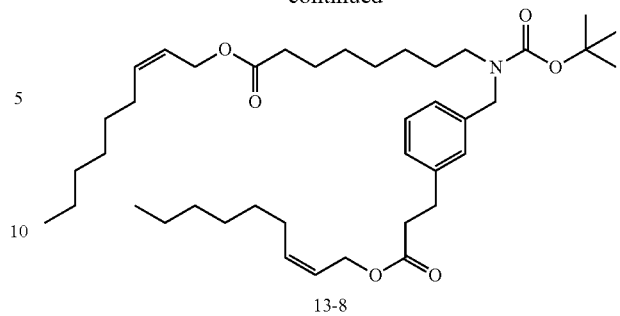

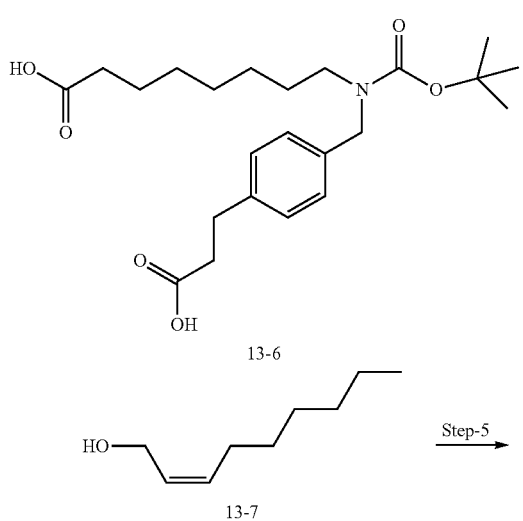

To a solution of 5.0 g compound 13-6 (1 eq.) in DCM (50 ml) were added 13.61 g EDC.HCl (6 eq.), 12.76 ml DIPEA (6 eq.), 5.05 g cis-2-nonen-1-ol (13.7; 3.0 eq.) and DMAP (0.4 eq.), successively at 0-5° C. The reaction mixture was stirred at room temperature for 14 hours.

Completion of reaction was monitored by EtOAc:hexane, 1:5. Starting material 13-6 was observed to be absent.

Resulting reaction mixture was diluted with DCM (500 ml) and washed with H₂O (2×150 ml). The residue was purified by silica gel (230-400 mesh) flash column chromatography (0-5% EtOAc in pet ether) to obtain product 13-8 as a pale yellow oil. Amount produced, 5.2 g; yield, 65%; confirmed by ¹H NMR and LC-MS.

Lipid 13: Step-6:

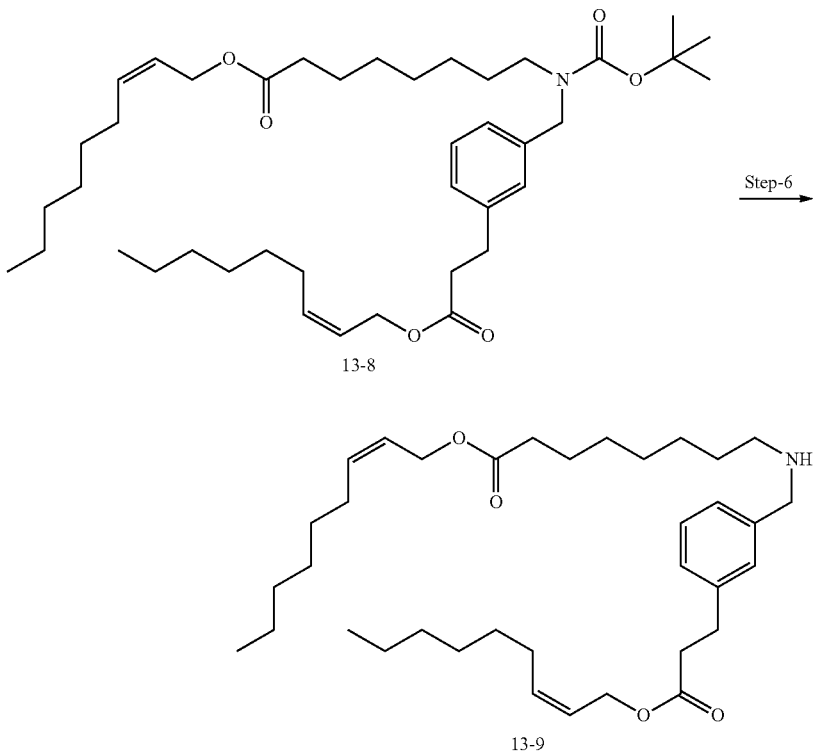

To a solution of 4.0 g compound 13-8 (1 eq.) in 25 ml DCM was added 8 ml TFA (2 eq.) at 0° C. The reaction mixture was stirred at room temperature for 2 hours.

Completion of reaction was monitored by TLC, MeOH:DCM: 0.5:9.5. Starting material 13-8 was observed to be absent.

The resulting reaction mixture was concentrated under reduced pressure, diluted with $H_2O$ (50 ml), neutralized with aqueous $NaHCO_3$. The product was extracted with DCM (2×250 ml) and washed with $H_2O$ (50 ml). The crude product obtained upon evaporation of volatiles the residue was purified by silica gel (230-400 mesh) flash column chromatography (10-40% EtOAc in pet ether) to obtain compound 13-9 as a pale yellow oil. Amount produced, 4.0 g; yield, 95%; confirmed by $^1H$ NMR and LC-MS.

Lipid 13: Step-7:

The resulting reaction mixture was diluted with DCM (500 ml), washed with $H_2O$ (2×100 ml), organic layer was dried and concentrated under reduced pressure. The crude product obtained upon evaporation of volatiles was purified by silica gel (230-400 mesh) flash column chromatography (0-5% MeOH in DCM) to obtain product Lipid 13 as a pale yellow oil. Quantity produced, 1.3 g; yield, 54%; confirmed by $^1H$ NMR and LC-MS; HPLC purity, >99%.

$^1$H-NMR, Lipid 13 (400 MHz, CDCl3) δ=7.10-7.40 (4), 5.67 (m, 2), 5.52 (m, 2), 4.45-4.65 (6), 3.15-3.32 (2), 3.07 (t, J=7.0, 2), 2.91 (t, J=7.0, 2), 2.65 (t, J=7.0, 2), 2.55 (t, J=7.0, 2), 2.27 (s, 6), 2.20-2.30 (2), 2.00-2.14 (4), 1.40-1.80 (6), 1.15-1.40 (22), 0.80-0.91 (6).

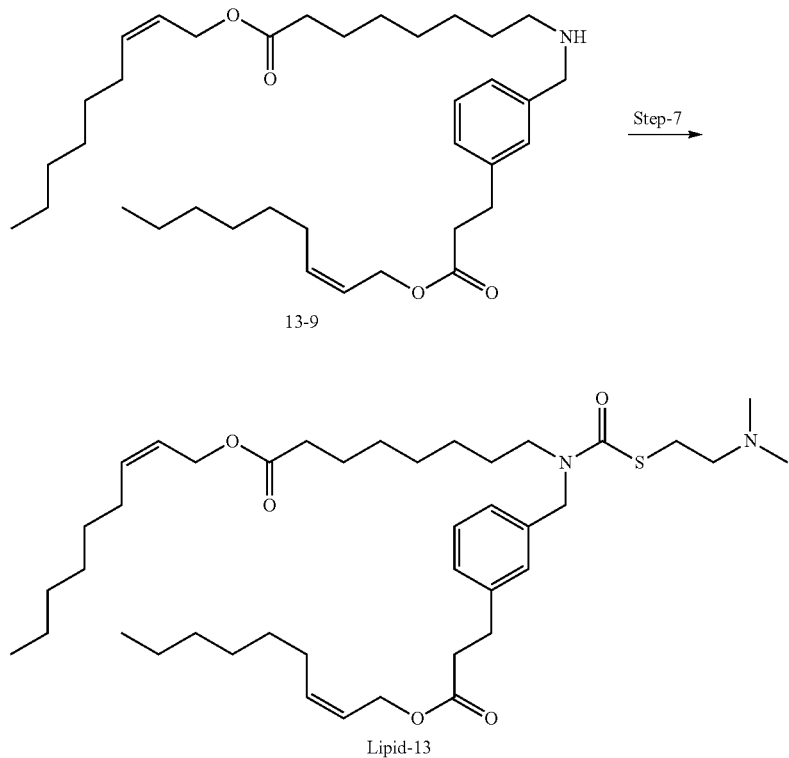

To a solution 2.0 g 13-9 (1 eq.) and 0.57 ml TEA (2 eq.) in 20 ml DCM was added 0.62 g triphosgene (0.9 eq.) at 0° C. The resulting reaction mixture was stirred at room temperature for 2 hours.

Completion of reaction was monitored by TLC, EtOAc:hexane, 1:4. Starting material 13-9 was observed to be absent.

The resulting reaction mixture was concentrated under nitrogen atmosphere, again diluted with 50 ml DCM, added 2.47 g 2-(dimethylamino)ethanethiol hydrochloride (5 eq.) and 3.94 ml TEA (8 eq.) at 0° C. The reaction mixture was stirred at room temperature for 48 hours.

Completion of reaction was monitored by TLC, 100% EtOAc. Some starting material, N—COCl intermediate, remained Example 3: Synthesis of Lipid 14

Figure 3:
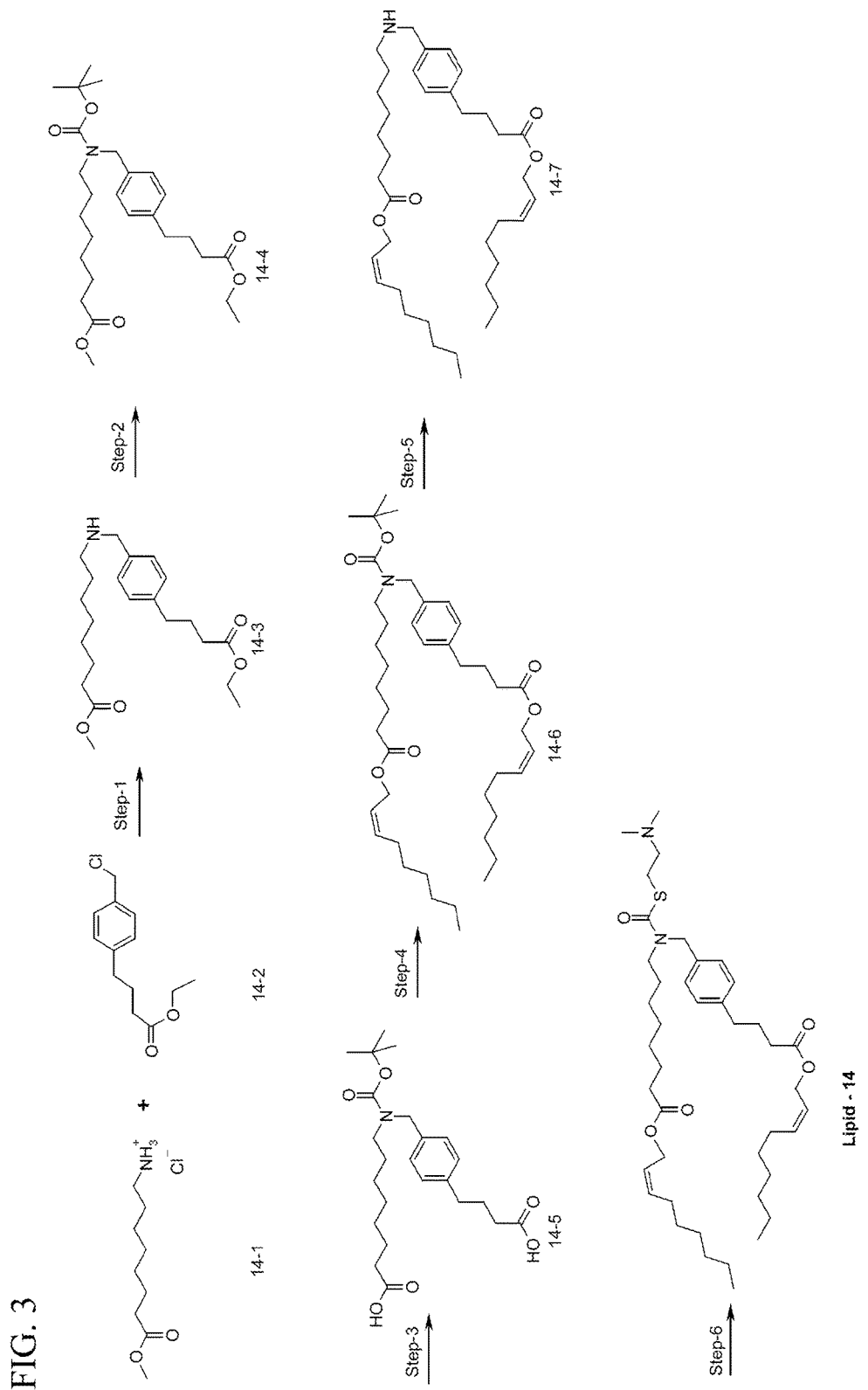
FIG. 3 shows the preparation of Lipid 14, showing intermediates 14-1 to 14-7. 14-1 and 14-2 are commercial starting materials. The reactions are described in detail in Example 3.

Lipid 14 was synthesized in six steps as shown in FIG. 3. Lipid 14: Step 1:

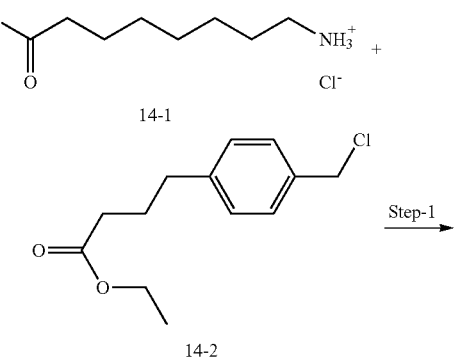

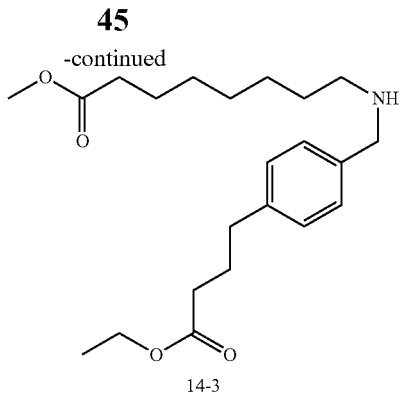

14-3

To a solution of 12 g amine hydrochloride 14-1 (1 eq.) in 200 ml ACN were added 23.7 g anhydrous $K_2CO_3$ (3 eq.) and 13.7 g compound 14-2 (1 eq.) at room temperature. The reaction mixture was stirred at room temperature for 16 hours.

Completion of the reaction was confirmed by TLC, MeOH:DCM, 1:9. Starting material (14-1) was observed to be absent.

The resulting reaction mixture was filtered to remove insoluble salts, diluted with EtOAc (500 ml), washed with $H_2O$ (2×100 ml) and concentrated. The crude product obtained upon evaporation of volatiles was purified by silica gel (230-400 mesh) flash column chromatography (0-4% MeOH in DCM) to obtain product 8-(4-(3-ethoxycarbonyl-propyl)-benzylamino)-octanoic acid methyl ester (14-3) as a pale yellow oil. Quantity produced, 8.5 g; yield, 40%; confirmed by $^1H$ NMR and LC-MS.

Lipid 14: Step 2:

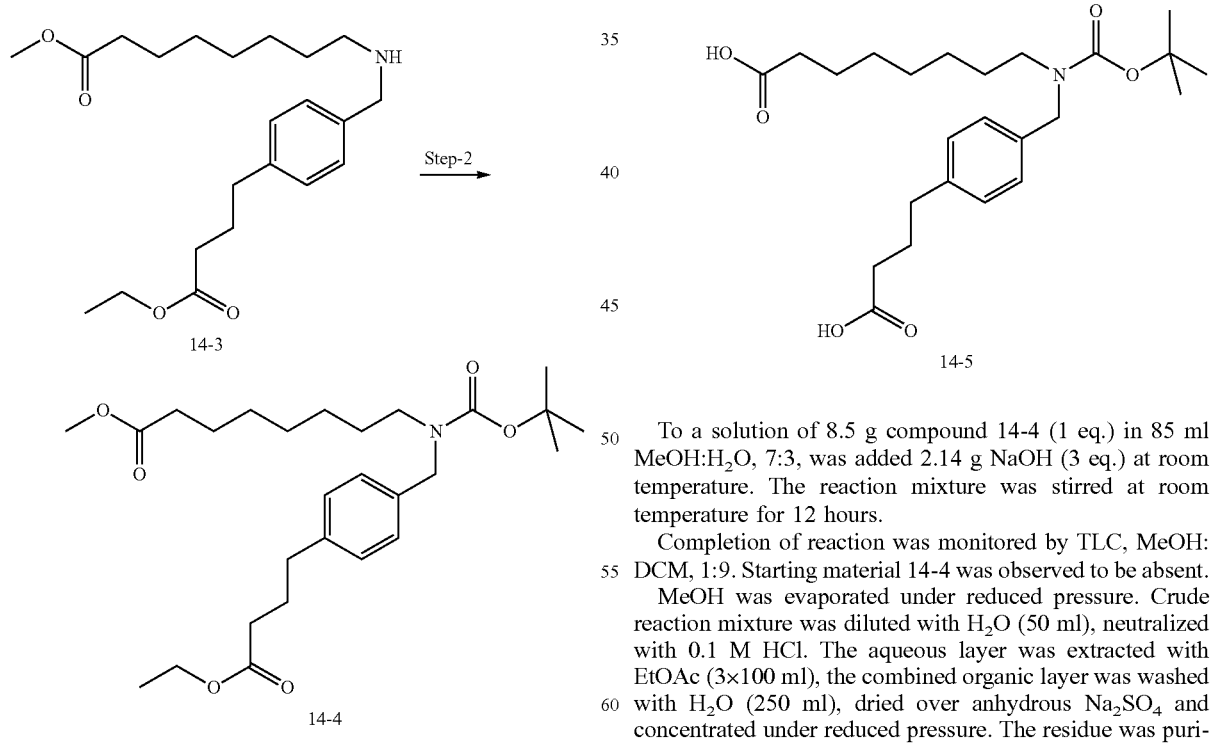

To a solution of 8.5 g compound 14-3 (1.0 eq.) in a 1:1 (v:v) mixture of 30 ml 1,4-dioxane:$H_2O$ were added 5.8 g (BOC)$_2$O (1.2 eq.) and 5.6 g NaHCO$_3$ (3.0 eq.) at room temperature. The reaction mixture was stirred at room temperature for 12 hours.

Completion of reaction mixture was observed by TLC, EtOAc:hexane, 2:8. Starting material (14-3) was observed to be absent.

The resulting reaction mixture was diluted with EtOAc (200 ml), washed with $H_2O$ (2×100 ml) and concentrated under reduced pressure. The residue was purified by silica gel (230-400 mesh) flash column chromatography (5-15% EtOAc in pet ether) to obtain 8-(tert-butoxycarbonyl-(4-(3-ethoxycarbonyl-propyl)-benzyl)-amino)-octanoic acid methyl ester (14-4) as a pale yellow liquid. Quantity produced, 8.9 g; yield, 83%; confirmed by $^1H$ NMR and LC-MS.

Lipid 14: Step-3

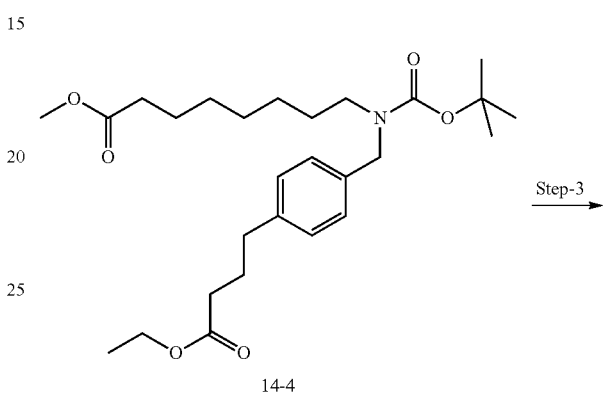

To a solution of 8.5 g compound 14-4 (1 eq.) in 85 ml MeOH:$H_2O$, 7:3, was added 2.14 g NaOH (3 eq.) at room temperature. The reaction mixture was stirred at room temperature for 12 hours.

Completion of reaction was monitored by TLC, MeOH:DCM, 1:9. Starting material 14-4 was observed to be absent.

MeOH was evaporated under reduced pressure. Crude reaction mixture was diluted with $H_2O$ (50 ml), neutralized with 0.1 M HCl. The aqueous layer was extracted with EtOAc (3×100 ml), the combined organic layer was washed with $H_2O$ (250 ml), dried over anhydrous $Na_2SO_4$ and concentrated under reduced pressure. The residue was purified by silica gel (230-400 mesh) flash column chromatography (0 to 3% MeOH in DCM) to obtain product n 8-(tert-butoxycarbonyl-(4-(3-carboxy-propyl)-benzyl)-amino)-octanoic acid (14-5) as off white solid. Amount produced, 7.6 g; yield, 98%; confirmed by $^1H$ NMR and LC-MS.

Lipid 14: Step-4

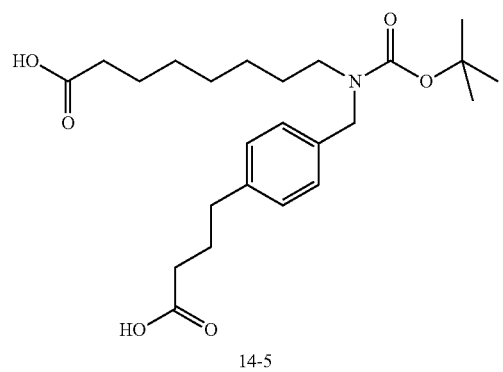

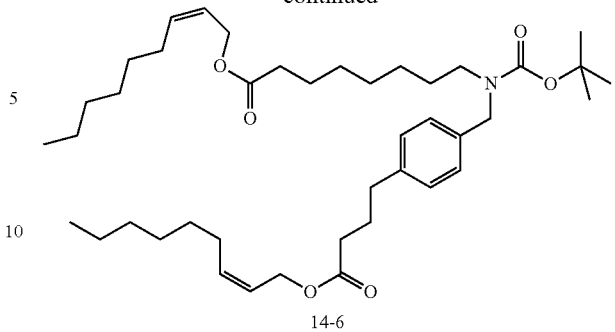

Step-4 →

To a solution of 7.5 g compound 14-5 (1 eq.) in 75 ml DCM were added 19.75 g EDC.HCl (6 eq.), 17.8 ml DIPEA (6 eq.), 7.2 g cis-2-nonen-1-ol (3 eq.) and 840 mg DMAP (0.4 eq.) successively at 0° C. The reaction mixture was stirred at room temperature for 14 hours.

The reaction was monitored by TLC EtOAc:hexane, 1:9. The starting material 14-5 was observed to be absent.

The resulting reaction mixture was diluted with DCM (200 ml) and washed with $H_2O$ (2×50 ml). The residue was purified by silica gel (230-400 mesh) flash column chromatography (0-8% EtOAc in pet ether) to obtain product 8-(tert-butoxycarbonyl-(4-(3-(((Z)-non-2-enyl)oxycarbonyl)-propyl)-benzyl)-amino)-octanoic acid (Z)-non-2-enyl ester (14-6) as a pale yellow oil. Quantity produced, 8.2 g; yield, 76%; confirmed by $^1$H NMR and LC-MS.

Lipid 14: Step-5

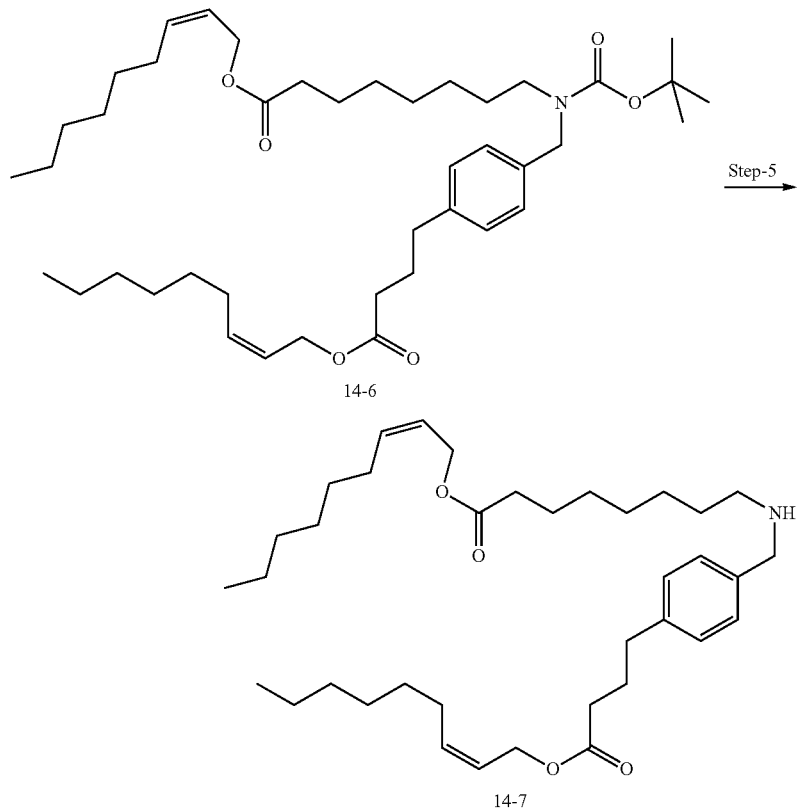

To a solution of 3.0 g compound 14-6 (1 eq.) in 30 ml DCM was added 6 ml TFA (2 eq.) at 0° C. The reaction mixture was stirred at room temperature for 2 hours.

Completion of reaction was monitored by TLC, MeOH:DCM, 1:9; starting material 14-6 was observed to be absent.

The resulting reaction mixture was concentrated under reduced pressure, diluted with $H_2O$ (25 ml), neutralized with aqueous $Na_2CO_3$. The product was extracted with DCM (2×150 ml) and organic layer was washed with $H_2O$ (100 ml). The crude product obtained upon evaporation of volatiles was purified by silica gel (230-400 mesh) flash column chromatography (10 to 40% EtOAc in pet ether) to obtain product 14-7 as a pale yellow oil. Quantity produced, 2.4 g; yield, 98%; confirmed by $^1H$ NMR and LC-MS.

Lipid 14: Step-6

The resulting reaction mixture was diluted with DCM (250 ml), washed with $H_2O$ (2×100 ml), organic layer was dried and concentrated under reduced pressure. The crude product obtained upon evaporation of volatiles, residue obtained was purified by silica gel (230-400 mesh) flash column chromatography (0-5% MeOH in DCM) to obtain product Lipid 14 as a pale yellow oil. Quantity produced, 1.1 g; yield, 34%; confirmed by $^1H$ NMR and LC-MS; HPLC purity, >99%.

$^1$H-NMR, Lipid 14 (400 MHz, CDCl3) δ=7.08-7.14 (4), 5.67 (m, 2), 5.51 (m, 2), 4.45-4.62 (6), 3.15-3.33 (2), 3.07 (t, J=7.0, 2), 2.52-2.67 (4), 2.27 (s, 6), 2.21-2.34 (4), 2.01-2.13 (4), 1.92 (m, 2), 1.40-1.52 (2), 1.17-1.40 (24), 0.82-0.91 (6).

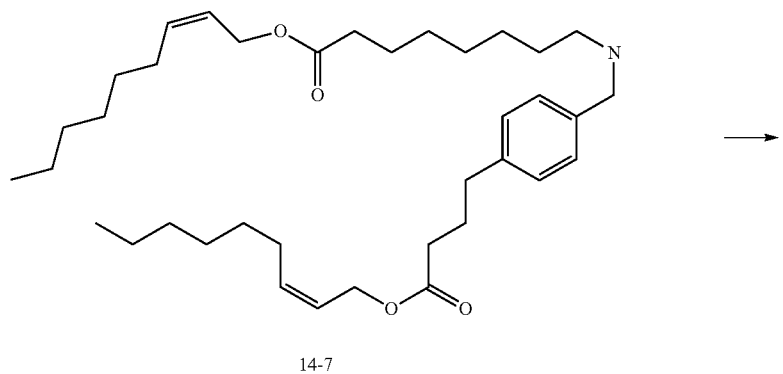

14-7

→

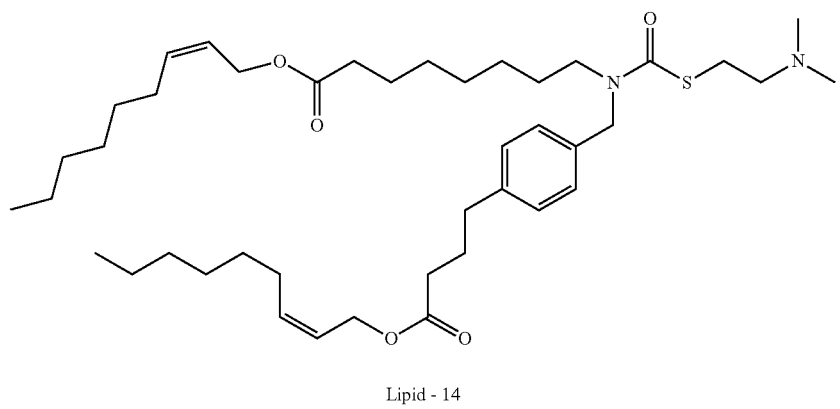

Lipid - 14

To a solution of 2.3 g 14-7 (1.0 eq.) and 1.1 ml TEA (2.0 eq.) in 25 ml DCM was added 1.16 g triphosgene (0.9 eq.) at 0° C. The resulting reaction mixture was stirred at room temperature for 30 minutes.

Completion of reaction was monitored by TLC, EtOAc, hexane. Starting material 14-7 was observed to be absent.

The resulting solution was concentrated under nitrogen atmosphere, again diluted with DCM (30 ml), added 2.8 g 2-(dimethylamino)ethanethiol hydrochloride (5 eq.) and 4.3 ml TEA (8 eq.) at 0° C. The reaction mixture was stirred at room temperature for 48 hours.

Completion of reaction was monitored by TLC, EtOAc, hexane. Starting material N-COCl intermediate was observed to be absent.

Example 4: Synthesis of Lipid 15

Figure 4:
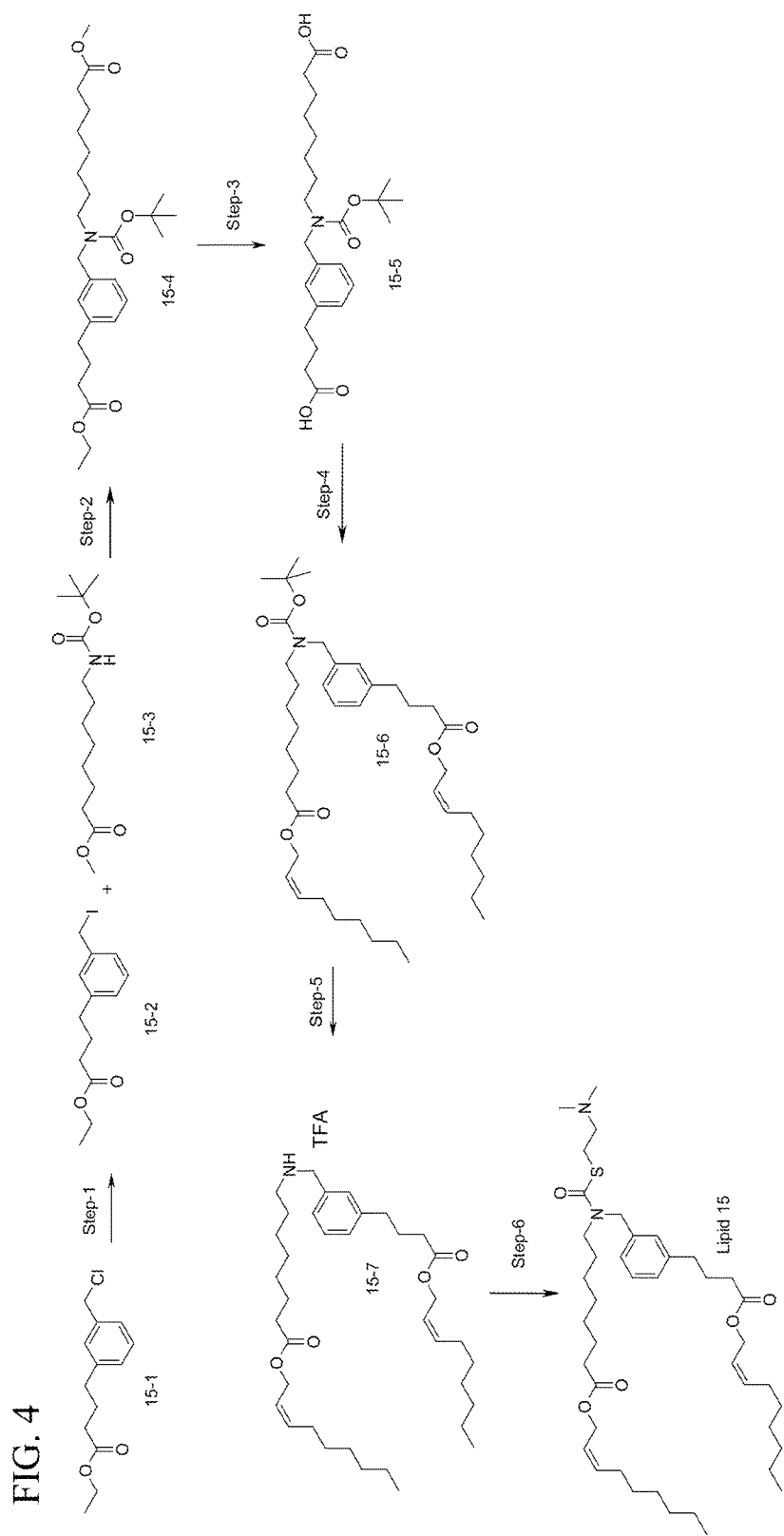
FIG. 4 shows the preparation of Lipid 15, showing intermediates 15-1 to 15-5. 15-1, 15-2, and 15-3 are commercial starting materials. The reactions are described in detail in Example 4.

Lipid 15 was synthesized in six steps as shown in FIG. 4.

Lipid 15: Step 1

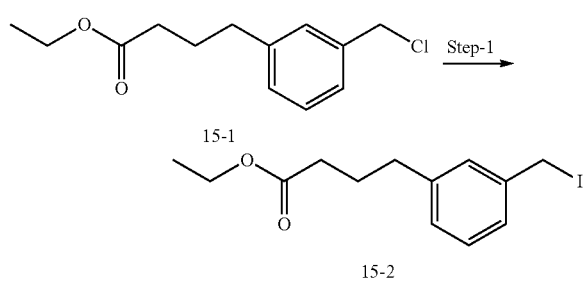

To a solution of 10.0 g compound 15-1 (1 eq.) in 100 ml acetone was added 6.85 g NaI (1.1 eq.) at room temperature. The reaction mixture was refluxed for 24 hours.

Completion of the reaction was confirmed by TLC, EtOAc:hexane, 3:7. Starting material 15-1 was observed to be absent.

Acetone was evaporated under reduced pressure and diluted with EtOAc (250 ml). The organic layer was washed with $H_2O$ (2×50 ml), dried over $Na_2SO_4$ and concentrated under reduced pressure to obtain product 15-2 as pale yellow oil. Amount produced, 12.0 g; yield, 86%; confirmed by $^1H$ NMR and LC-MS.

Lipid 15: Step 2

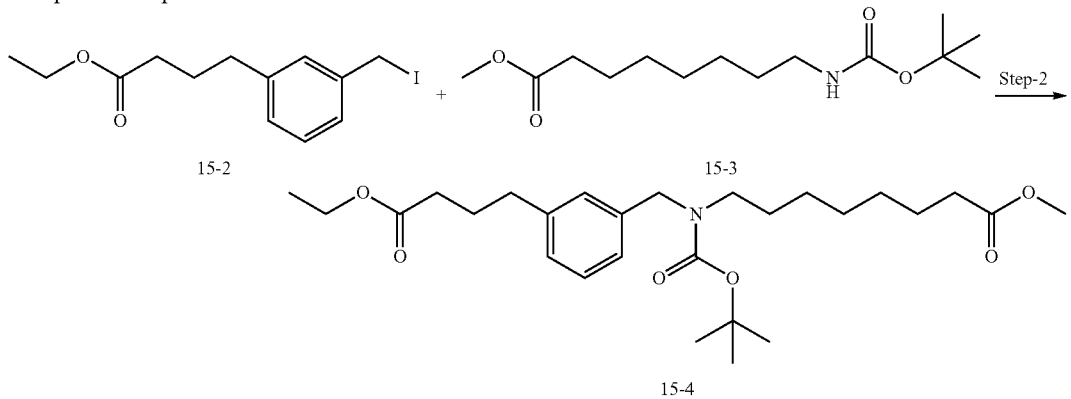

To a solution of 10.0 g compound 15-3 (1.0 eq.) in 50 ml DMF were added 60% 3.0 g NaH (2.0 eq.) and 13.3 g compound 15-2 (1.1 eq.) at 0° C. The reaction mixture was stirred at 0° C. for 1 hour.

Completion of reaction was monitored by TLC, EtOAc:DCM, 1:9. Starting material 15-3 intermediate was observed to be absent.

The resulting reaction mixture was quenched with saturated $NH_4Cl$ (20 ml), diluted with EtOAc (500 ml), organic later was washed with $H_2O$ (3×50 ml), dried over $Na_2SO_4$ and concentrated under reduced pressure. The crude product obtained upon evaporation of the volatiles was purified by silica gel column chromatography (0-5% EtOAc in pet ether) to obtain product 15-4 as a pale yellow oil. Quantity produce, 10.0 g; yield, 65%; confirmed by $^1H$ NMR and LC-MS.

Lipid 15: Step 3

To a solution of 10.0 g compound 15-4 (1 eq.) in 50 ml of a 4:1 mixture of MeOH—$H_2O$ was added 2.5 g NaOH (1 eq.) at room temperature. The reaction mixture was stirred at room temperature for 16 hours.

Completion of reaction was monitored by TLC, MeOH:DCM, 1:9. Starting material 15-4 intermediate was observed to be absent.

MeOH was evaporated under reduced pressure, crude reaction mixture was diluted with $H_2O$ (50 ml), neutralized with 0.1 M HCl. Then aqueous layer was extracted with EtOAc (3×100 ml), the combined EtOAc layer was washed with $H_2O$ (250 ml), dried over $Na_2SO_4$ and concentrated under reduced pressure. The crude product obtained upon evaporation of the volatiles was purified by silica gel column chromatography (0-2% MeOH in DCM) to obtain product 15-5 as a pale yellow oil. Quantity produced, 7.0 g; yield, 76%; confirmed by $^1H$ NMR and LC-MS

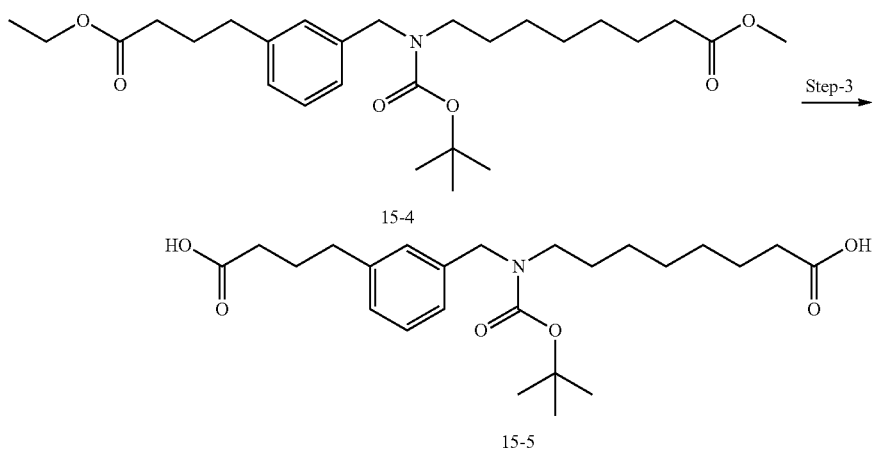

Lipid 15: Step 4

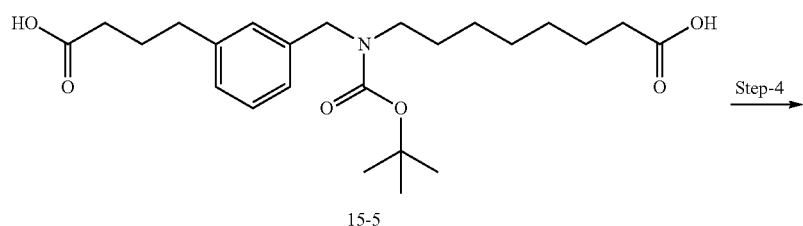

15-5

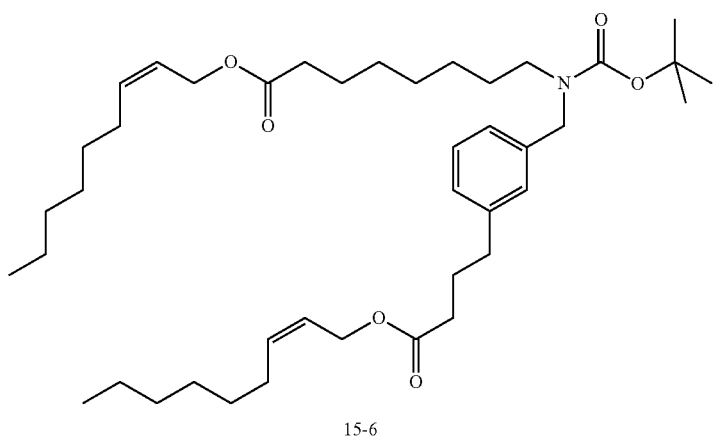

15-6

To a solution of 5.0 g compound 15-5 (1.0 eq.) in 50 ml DCM were added 13.2 g EDC.HCl (6.0 eq.), 11.9 ml DIPEA (6.0 eq.), 4.8 g cis-2-nonen-1-ol (3.0 eq.) and 557 mg DMAP (0.4 eq.) at 0° C. The reaction mixture was stirred at room temperature for 14 hours.

Completion of reaction was monitored by TLC, EtOAc: hexane, 1:9. Starting material 15-5 intermediate was observed to be absent.

Resulting reaction mixture was diluted with DCM (200 ml) and washed with $H_2O$ (2×50 ml). The crude product obtained upon evaporation of volatiles was purified through silica gel (230-400 mesh) column chromatography (0-2% EtOAc in pet ether) to give product 15-6 as a pale yellow oil. Quantity produced, 5.1 g; yield, 64%; confirmed by $^1H$ NMR and LC-MS.

Lipid 15: Step 5

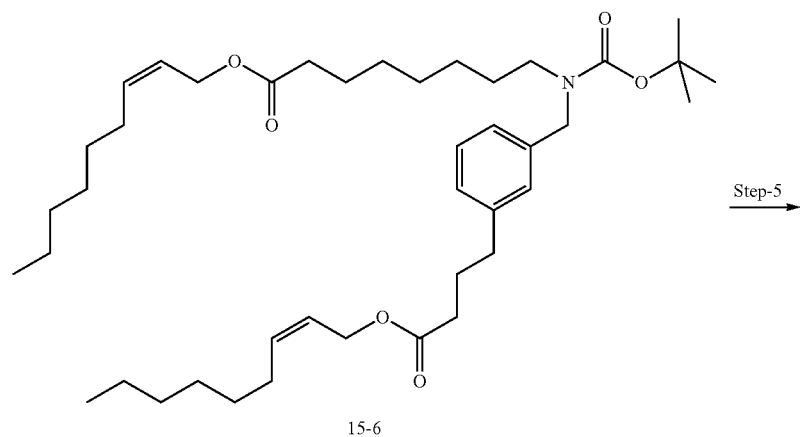

15-6

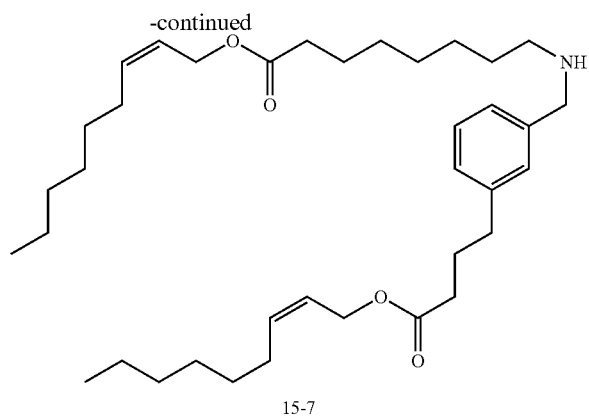

15-7

To a solution of 5.0 g compound 15-6 (1 eq.) in 50 ml DCM was added 10 ml TFA (2 volumes) at 0° C. The reaction mixture was stirred at room temperature for 2 hours.

Completion of reaction was monitored by TLC, MeOH:DCM, 1:9. Starting material 15-6 intermediate was observed to be absent.

The resulting reaction mixture was concentrated under reduced pressure, diluted with $H_2O$ (25 ml), neutralized with aqueous $Na_2CO_3$. The product was extracted with DCM (2×250 ml) and organic layer was washed with $H_2O$ (100 ml). The crude product obtained upon evaporation of volatiles was purified through silica gel (230-400 mesh) column chromatography (0-5% MeOH in DCM) to give product 15-7 as a pale yellow oil. Quantity produced, 3.8 g; yield, 90%; confirmed by 1H NMR and LC-MS.

Lipid 15: Step 6

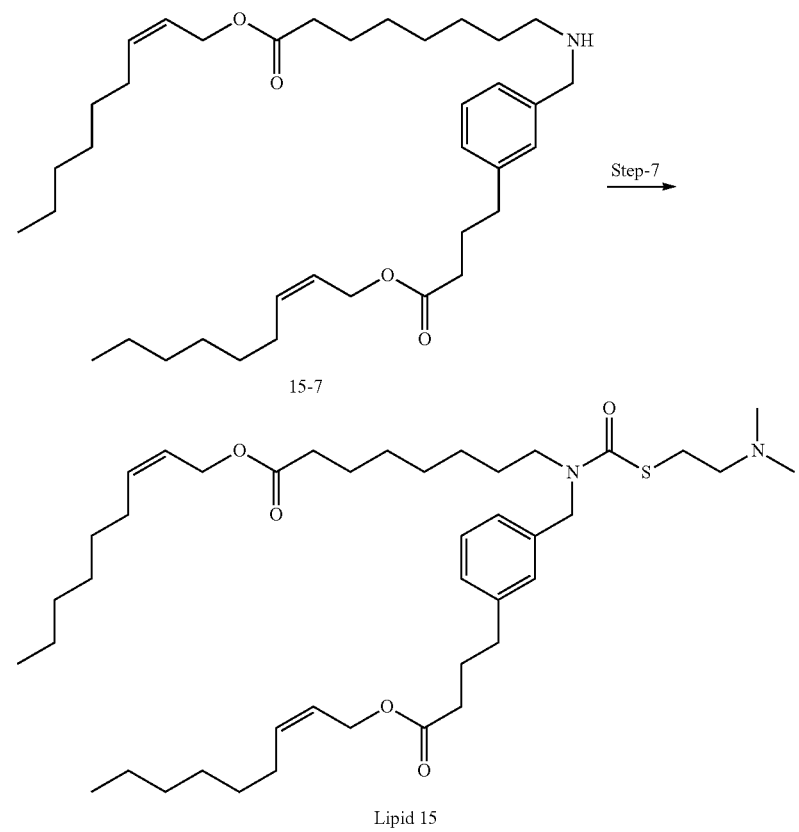

To a solution of 3.7 g 15-7 (1.0 eq.) and 1.75 ml TEA (2.0 eq.) in 30 ml DCM was added 1.68 g triphosgene (0.9 eq.) at 0° C. The resulting reaction mixture was stirred at room temperature for 0.5 h.

Completion of reaction was monitored by TLC, EtOAc:DCM, 1:9. Starting material N—COCl intermediate was observed to be absent.

The resulting solution was concentrated under nitrogen atmosphere, again diluted with 40 ml DCM, 4.4 g 2-(dimethylamino)ethanethiol hydrochloride (5 eq.) and 7.07 ml TEA (8 eq.) at 0° C. The reaction mixture was stirred at room temperature for 48 hours.

Completion of reaction was monitored by TLC, EtOAc: DCM, 1:9. Starting material N—COCl intermediate was observed to be absent.

The resulting reaction mixture was diluted with DCM (250 ml), washed with H$_2$O (2×100 ml), organic layer was dried and concentrated under reduced pressure. The crude product obtained upon evaporation of volatiles was purified through silica gel (230-400 mesh) column chromatography (25-95% EtOAc in pet ether) to give product Lipid 15 as a pale yellow oil. Quantity produced, 1.4 g; yield, 37%; confirmed by $^1$H NMR and LC-MS; HPLC purity, >99%.

$^1$H-NMR, Lipid 15 (400 MHz, CDCl$_3$) δ=7.24 (m, 1), 7.00-7.15 (3), 5.67 (m, 2), 5.51 (m, 2), 4.45-4.65 (6), 3.15-3.34 (2), 3.09 (t, J=7.0, 2), 2.67 (t, J=7.0, 2), 2.57 (t, J=7.0, 2), 2.23-2.42 (10), 2.03-2.13 (4), 1.92 (m, 2), 1.15-1.40 (26), 0.82-0.91 (6).

Example 5: Synthesis of Lipid 16

Figure 5:
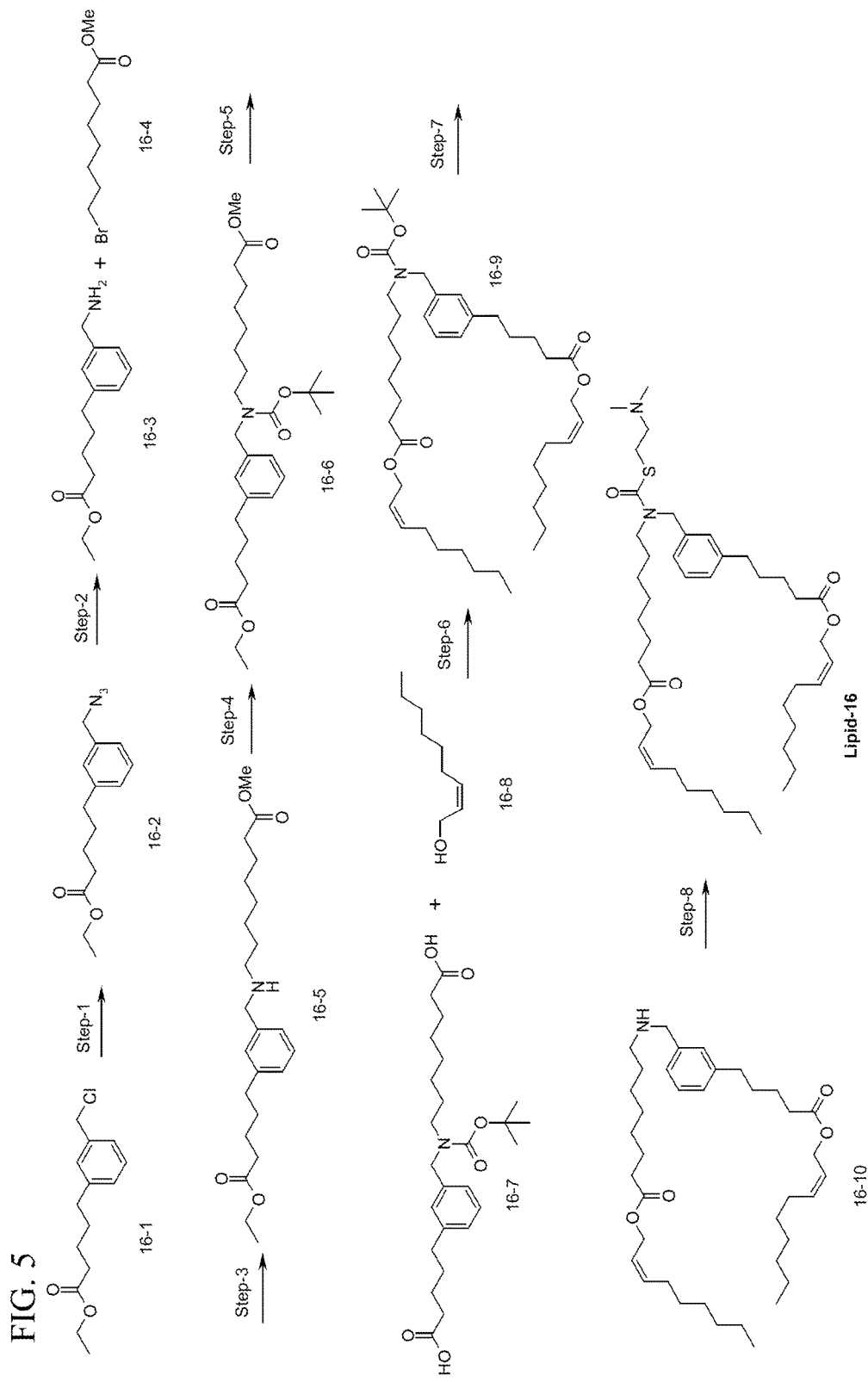
FIG. 5 shows the preparation of Lipid 16, showing intermediates 16-1 to 16-10. 16-1, 16-2, 16-4, and 16.8 are commercial starting materials. The reactions are described in detail in Example 5.

Lipid 16 was synthesized in eight steps as shown in FIG. 5.

Lipid 16: Step-1

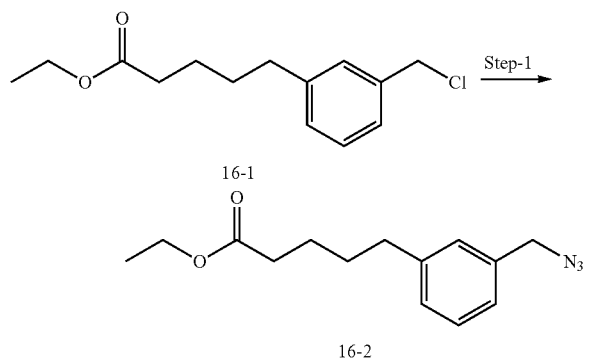

To a solution of 24 g 5-(3-chloromethyl-phenyl)-pentanoic acid ethyl ester (16-1; 1 eq.) in 120 ml DMF, 12.2 g NaN$_3$ (2 eq.) was added and the mixture was stirred at 65° C. for 2.5 hours.

Completion of reaction was monitored by TLC, EtOAc: hexane, 0.5:9.5. Starting material 16.1 intermediate was observed to be absent.

After completion of reaction, reaction mixture was diluted with H$_2$O (50 ml) and extracted with EtOAc (3×100 ml). The combined EtOAc layer was washed with H$_2$O (250 ml), dried over Na$_2$SO$_4$ and concentrated under reduced pressure to obtain 5-(3-azidomethyl-phenyl)-entanoic acid ethyl ester (16-2) as a pale yellow oil. Quantity produced, 23.1 g; yield, 94%; confirmed by $^1$H NMR and LC-MS; taken to further steps without further purification.

Lipid 16: Step-2

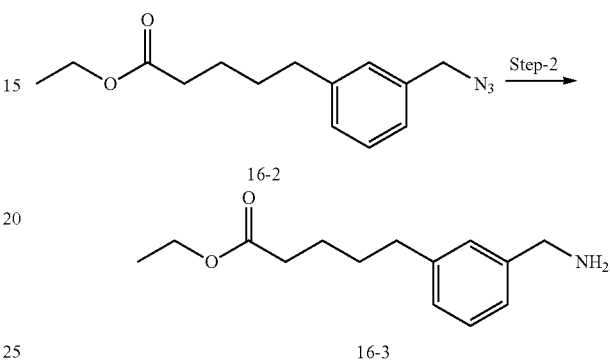

To a solution of 23 g 5-(3-azidomethyl-phenyl)-entanoic acid ethyl ester 16-2 (1 eq.) in 230 ml tetrahydrofuran (THF):H$_2$O, 9:1, 45.8 g PPh$_3$ (2 eq.) was added portion-wise at 25° C. and the resulting mixture was stirred for 12 hours.

Completion of reaction was monitored by TLC, EtOAc: hexane, 6:4. Starting material 16-2 intermediate was observed to be absent.

After completion of reaction, reaction mixture was diluted with H$_2$O (50 ml), extracted with EtOAc (3×100 ml), the combined EtOAc layer was washed with H$_2$O (250 ml), dried over anhydrous Na$_2$SO$_4$ and concentrated under reduced pressure the residue was purified by silica gel (60-120 mesh) flash column chromatography (10-30% EtOAc in pet ether) to obtain 5-(3-aminomethyl-phenyl)-pentatonic acid ethyl ester (16-3) as a pale yellow liquid. Quantity produced, 12.5 g; yield, 61%; confirmed by $^1$H NMR and LC-MS.

Lipid 16: Step-3

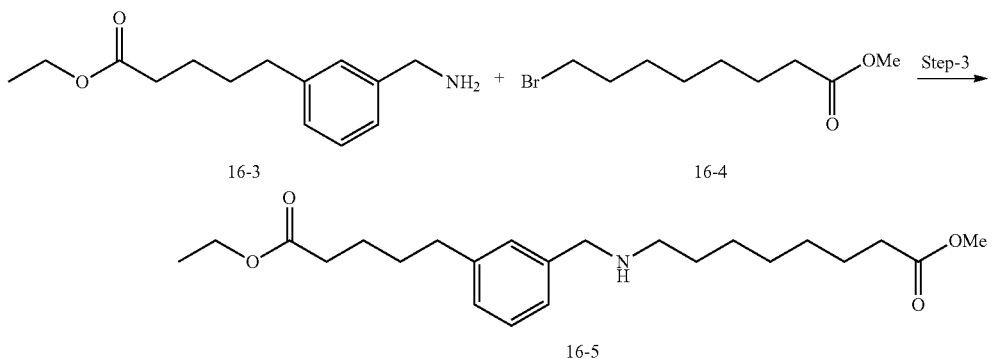

To a solution of 12.5 g 5-(3-aminomethyl-phenyl)-pentanoic acid ethyl ester 16-3 (1 eq.) and 12.6 g 8-bromo-octanoic acid methyl ester 16-4 (1 eq.) in 120 ml ACN at 25°

C., 21.9 g anhydrous K₂CO₃ (3 eq.) was added and was heated to 60° C. for 6 hours. After 16 hours, the resulting reaction mixture was cooled to 25° C.

Completion of reaction was monitored by TLC, MeOH:DCM, 0.5:9.5. Starting material 16-4 intermediate was observed to be absent.

Reaction mixture was diluted with H₂O and EtOAc. Organic layer was separated and washed with H₂O. The organic layer dried over anhydrous Na₂SO₄ and concentrated under reduced pressure, the residue obtained was purified by silica gel (230-400 mesh) flash column chromatography (0-4% MeOH in DCM) to obtain 8-[3-(4-ethoxy-carbonyl-butyl)-benzylamino]-octanoic acid methyl ester (16-5) as a pale yellow oil. Quantity produced, 8.25 g; yield, 40%; confirmed by ¹H NMR and LC-MS.

Lipid 16: Step-4

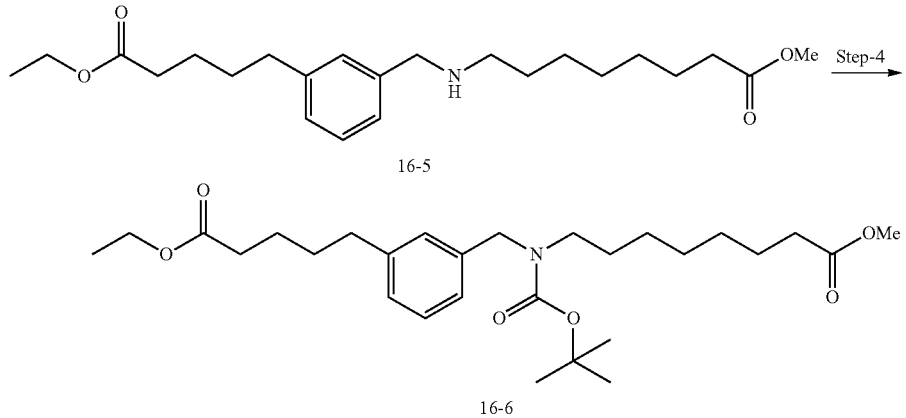

To a solution of 8.25 g compound 16-5 (1.0 eq.) in a 80 ml 2:1 mixture of 1,4-dioxane:H₂O, were added 5.45 g (BOC)₂O (1.2 eq.) and 5.3 g NaHCO₃ (3.0 eq.) at room temperature. The reaction mixture was stirred at room temperature for 6 hours.

Completion of reaction was monitored by TLC, EtOAc:hexane, 2:8. Starting material 16-5 intermediate was observed to be absent.

After completion of reaction, the resulting reaction mixture was diluted with EtOAc (200 ml, washed with H₂O (2×100 ml) and concentrated under reduced pressure. The residue was purified by silica gel (230-400 mesh) flash column chromatography (2-8% EtOAc in pet ether) to obtain product 16-6 as a pale yellow liquid. Quantity produced, 8.64 g; yield, 83%; confirmed by ¹H NMR and LC-MS.

Lipid 16: Step-5

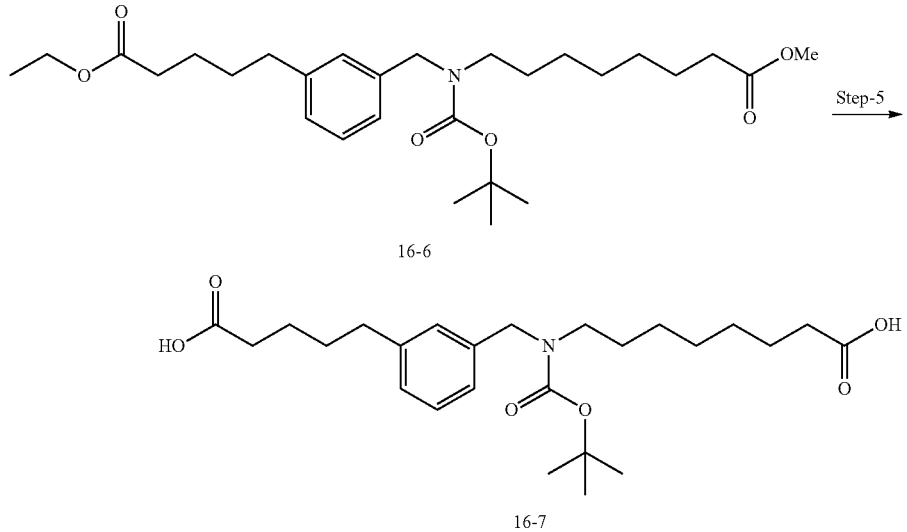

To a solution of 7.8 g compound 16-6 (1 eq.) in a mixture of 80 ml MeOH:$H_2O$, 7:3, was added 19 g NaOH (3 eq.) at room temperature. The reaction mixture was stirred at room temperature for 14 hours.

Completion of reaction was monitored by TLC, MeOH: DCM, 1:9. Starting material 16-6 intermediate was observed to be absent.

MeOH was evaporated under reduced pressure. The crude reaction mixture was diluted with $H_2O$ (50 ml), neutralized with 0.1 N HCl. The aqueous layer was extracted with EtOAc (3×100 ml), the combined EtOAc layer was washed with $H_2O$ (250 ml), dried over $Na_2SO_4$ and concentrated under reduced pressure. The residue was purified by silica gel (230-400 mesh) flash column chromatography (25-50% EtOAc in pet ether) to obtain product 16-7 as an off white solid. Quantity produced, 7.0 g; yield, 98%; confirmed by $^1$H NMR and LC-MS.

Lipid 16: Step-6

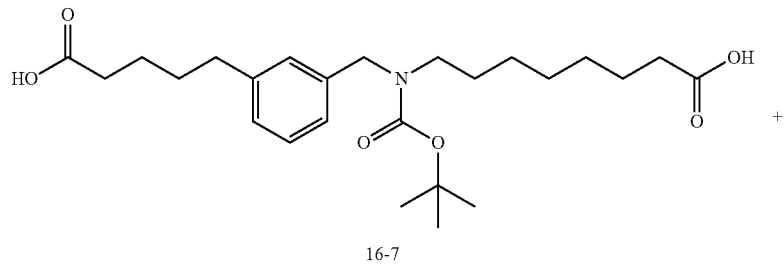

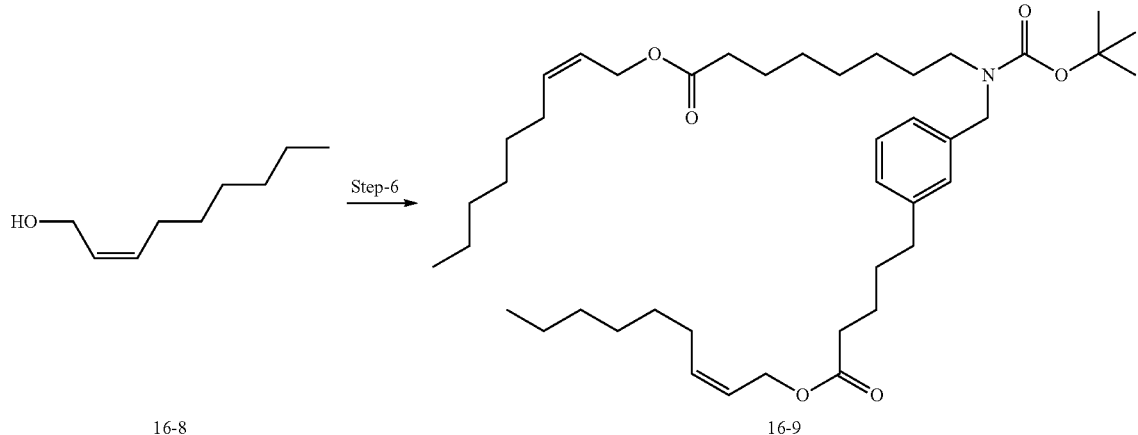

To a solution of 7 g compound 16-7 (1.0 eq.) in 70 ml DCM were added 17.86 g EDC.HCl (6.0 eq.), 16.6 ml DIPEA (6.0 eq.), 4.8 g cis-2-nonen-1-ol (16-8) (3.0 eq.) and 557 mg DMAP (0.4 eq.) successively at 0-5° C. The reaction mixture was stirred at room temperature for 14 hours.

Completion of reaction was monitored by TLC, EtOAc: hexane, 1:9. Starting material 16-7 intermediate was observed to be absent.

The resulting reaction mixture was diluted with DCM (200 ml) and washed with $H_2O$ (2×50 ml). The crude product obtained upon evaporation of volatiles was purified by silica gel (230-400 mesh) flash column chromatography (0-8% EtOAc in pet ether) to obtain product 16.9 as a pale yellow oil. Quantity produced, 5.1 g; yield, 64%; confirmed by $^1$H NMR and LC-MS.

Lipid 16: Step-7

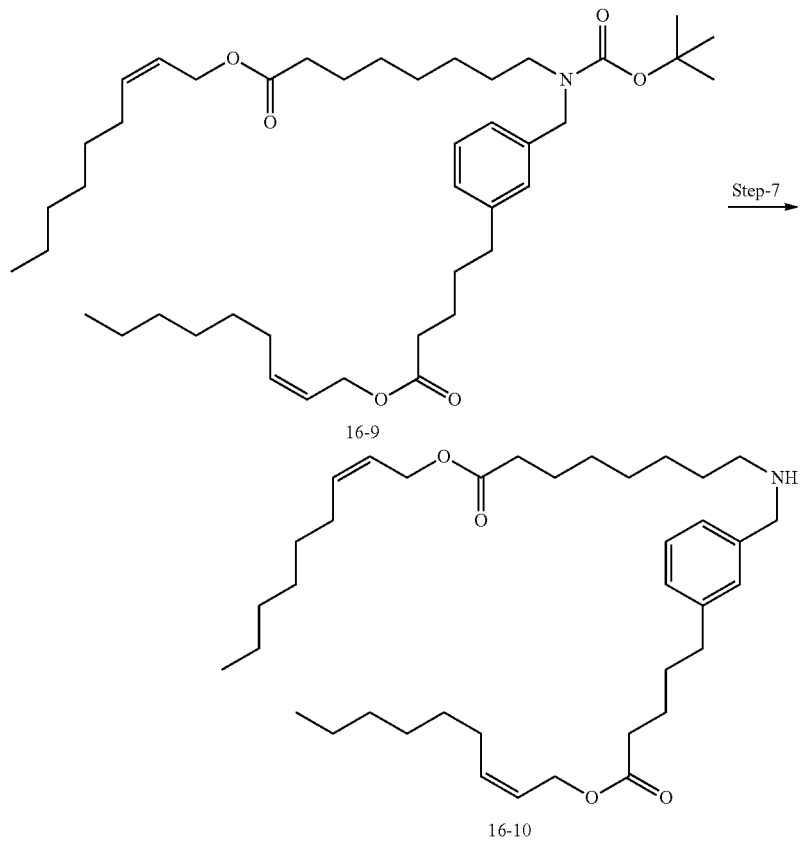

To a solution of 3.0 g compound 16-9 (1 eq.) in 30 ml DCM was added 6 ml TFA (2 vol.) at 0° C. The reaction mixture was stirred at room temperature for 2 hours.

Completion of reaction was monitored by TLC, MeOH: DCM, 1:9. Starting material 16-9 intermediate was observed to be absent.

The resulting reaction mixture was concentrated under reduced pressure, diluted with H$_2$O (25 ml), neutralized with aqueous. Na$_2$CO$_3$. Product was extracted with DCM (2×100 ml) and washed with H$_2$O (50 ml). The crude product obtained upon evaporation of volatiles was purified by silica gel (230-400 mesh) flash column chromatography (0-3% MeOH in DCM) to obtain product 16-10 as a pale yellow oil. Quantity produced, 2.4 g; yield, 96%; confirmed by $^1$H NMR and LC-MS.

Lipid 16: Step-8

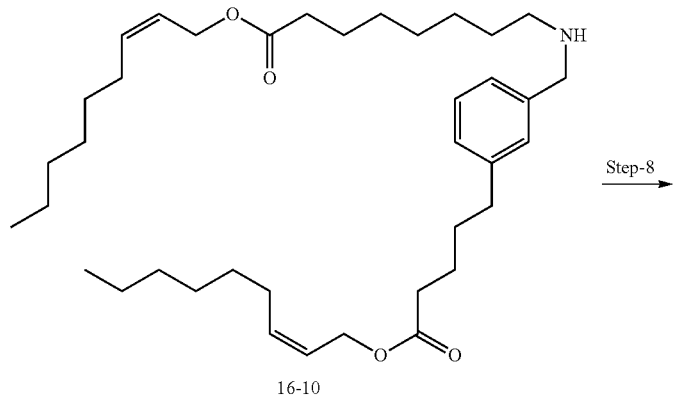

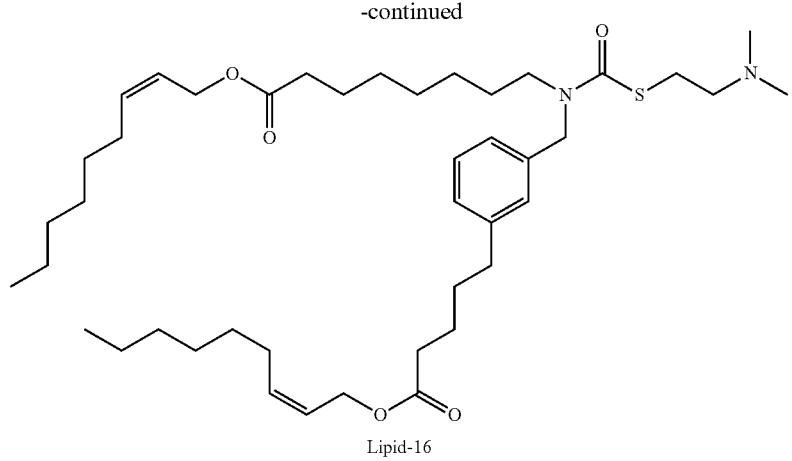

Lipid-16

To a solution of 2.0 g 16-10 (1 eq.) and 0.93 ml TEA (2 eq.) in 20 ml DCM was added 0.889 g triphosgene (0.9 eq.) at 0° C. The resulting reaction mixture was stirred at room temperature for 2 hours.

Completion of reaction was monitored by TLC, EtOAc: hexane, 1:4. Starting material N—COCl intermediate was observed to be absent.

The resulting solution was concentrated under nitrogen atmosphere, again diluted with 20 ml DCM, added 2.35 g 2-(dimethylamino)ethanethiol hydrochloride (5 eq.) and 3.74 ml TEA (8 eq.) at 0° C. The reaction mixture was stirred at room temperature for 48 hours.

Completion of reaction was monitored by TLC, 100% EtOAc. Starting material N—COCl intermediate was observed to be absent.

The resulting reaction mixture was diluted with DCM (200 ml), washed with $H_2O$ (2×50 ml), organic layer was dried and concentrated under reduced pressure. The crude product obtained upon evaporation of volatiles. The residue was purified by silica gel (230-400 mesh) flash column chromatography (0-5% MeOH in DCM) to obtain product Lipid 16 as a pale yellow oil. Quantity produced, 1.3 g; yield, 54%; confirmed by $^1H$ NMR and LC-MS; HPLC purity, 98%.

$^1$H-NMR, Lipid 16 (400 MHz, CDCl$_3$) δ=7.23 (m, 1), 6.98-7.13 (3), 4.57 (m, 2), 5.52 (m, 2), 4.45-4.65 (6), 3.15-3.37 (2), 3.08 (t, J=7.0, 2), 2.55-2.67 (4), 2.27 (s, 6), 2.22-2.35 (4), 2.00-2.13 (4), 1.45-1.52 (4), 1.12-1.40 (26), 0.85-0.91 (6).

Example 6: Synthesis of Lipid 17

Figure 6:
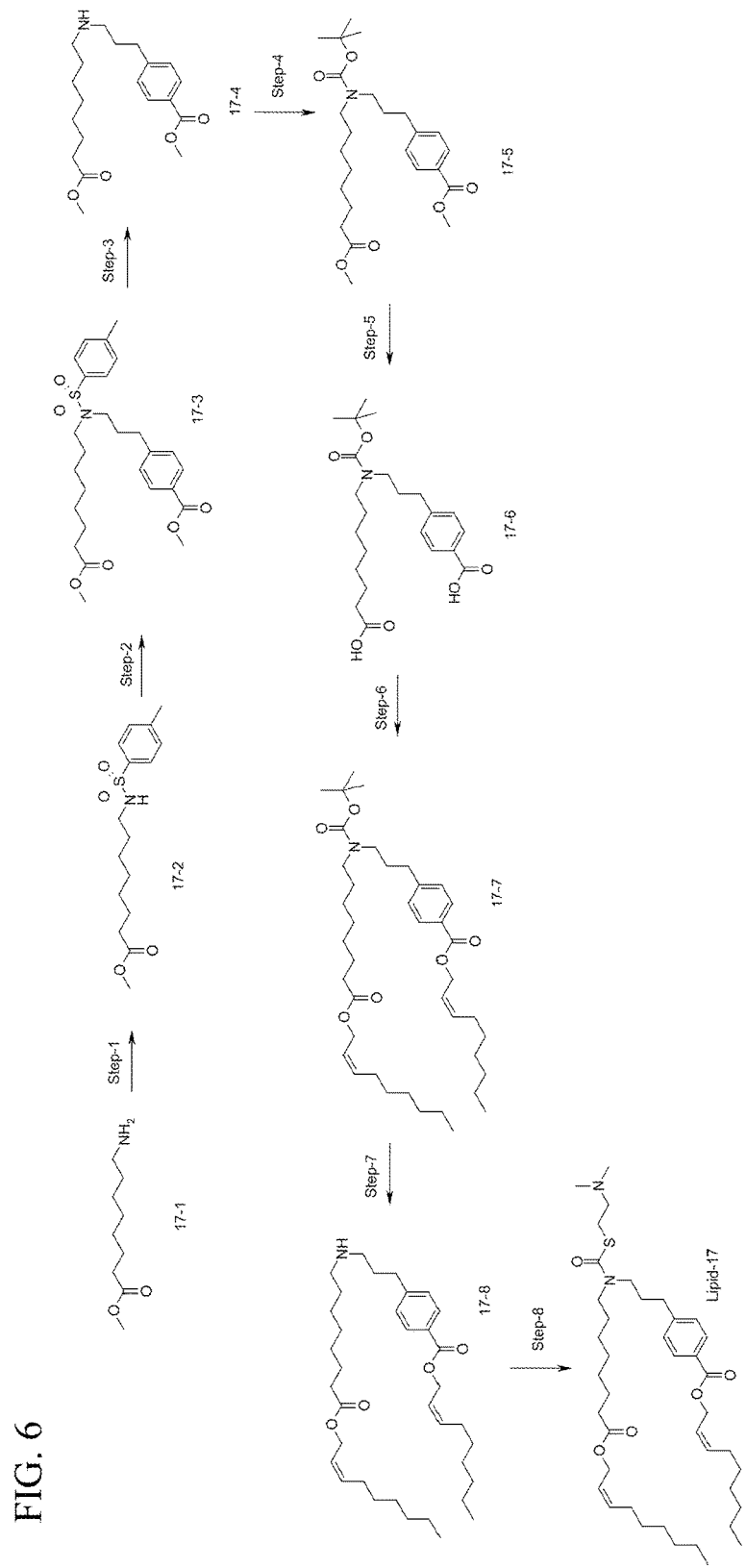
FIG. 6 shows the preparation of Lipid 17, showing intermediates 17-1 to 17-8. 17-1 and 17-2 are commercial starting materials. The reactions are described in detail in Example 6.

Lipid 17 was synthesized in eight steps as shown in FIG. 6.

Lipid 17: Step 1

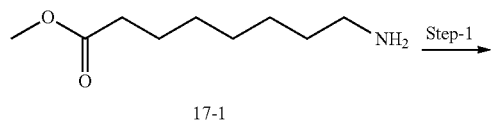

17-1

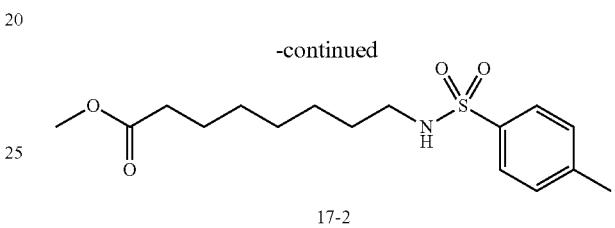

17-2

To a solution of 50.0 g compound 17-1 (1 eq.) in 500 ml DCM were added 100 ml TEA (2.5 eq.) and 80.0 g P-toluene sulfonyl chloride (1.5 eq.) at 0° C. The reaction mixture was stirred at room temperature for 4 hours.

Completion of reaction was monitored by TLC, 40% EtOAc in hexane. Starting material 17-1 intermediate was observed to be absent.

The resulting reaction mixture was diluted with DCM (500 ml), washed with $H_2O$ (2×250 ml) and concentrated under reduced pressure. The residue obtained upon evaporation of the solvents was purified by silica gel flash column chromatography (2-10% EtOAc in pet ether) to obtain product 17-2 as a pale yellow solid. Quantity produced, 52.0 g; yield, 87%; confirmed by $^1H$ NMR and LC-MS.

Lipid 17: Step 2

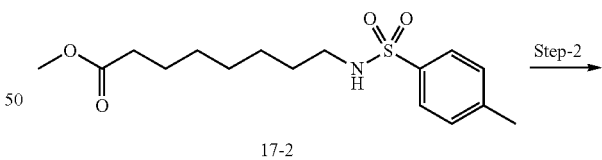

17-2

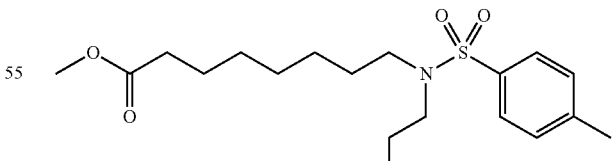

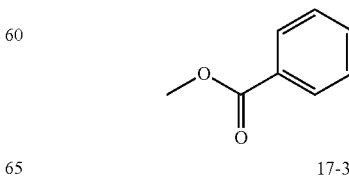

17-3

To a solution of 30.0 g compound 17-2 (1 eq.) in 150 ml DMF were added 59.70 g Cs$_2$CO$_3$ (2 eq.), 34.0 g 4-(3-bromo-propyl)-benzoic acid methyl ester (1.4 eq.) and 1.5 g KI (0.1 eq.) at room temperature. The reaction mixture was stirred at 50° C. for 6 hours.

Completion of reaction was monitored by TLC, 10% EtOAc in hexane. Starting material 17-2 intermediate was observed to be absent.

The resulting reaction mixture was diluted with DCM (500 ml), washed with H$_2$O (2×250 ml) and organic layer was concentrated under reduced pressure. The residue obtained upon evaporation of the solvents was purified by silica gel flash column chromatography (2-10% EtOAc in pet ether) to obtain product 17-3 as a pale yellow solid. Quantity produced, 39.0 g; yield, 84%; confirmed by $^1$H NMR and LC-MS.

Lipid 17: Step 3

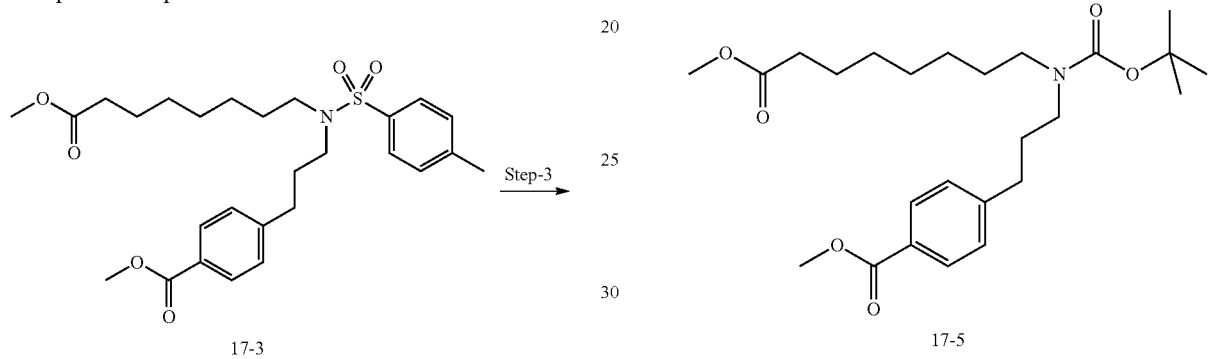

17-3

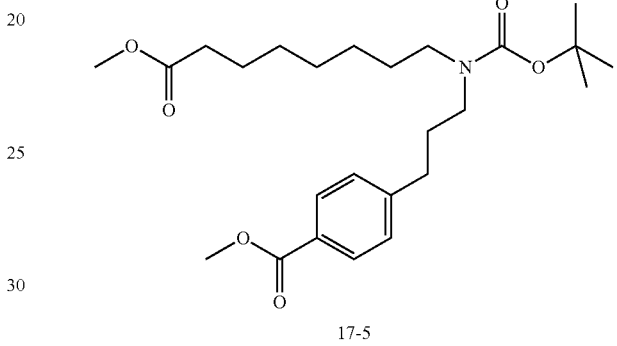

17-4

To a solution of 6.0 g compound 17-3 (1 eq.) in 60 ml THF was added 71 ml 0.50 M potassium diphenylphosphide (3 eq.) in THF solution at −78° C. The reaction mixture was stirred for 2 hours at the same temperature. Diluted 30.0 ml 1 N HCl ( ) was then added to the reaction mixture and the temperature was raised to room temperature. The resulting mixture was stirred for 30 minutes.

Completion of reaction was monitored by TLC, MeOH:DCM, 1:9. Starting material 17-3 intermediate was observed to be absent.

Saturated aqueous NaHCO$_3$ (100 ml) was added to the mixture and the mixture was extracted with EtOAc (3×100 ml). The combined organic layer was washed with brine, dried over anhydrous Na$_2$SO$_4$, and concentrated under reduced pressure. Purification by silica gel chromatography (0.5-5% MeOH in DCM) resulted the compound 17-4 as a pale yellow oil. Quantity produced, 2.9 g; yield, 70%; confirmed by $^1$H NMR and LC-MS.

Lipid 17: Step 4

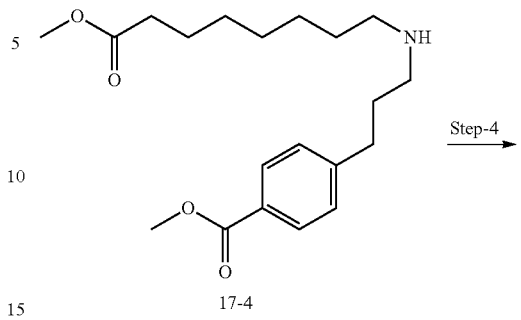

17-4

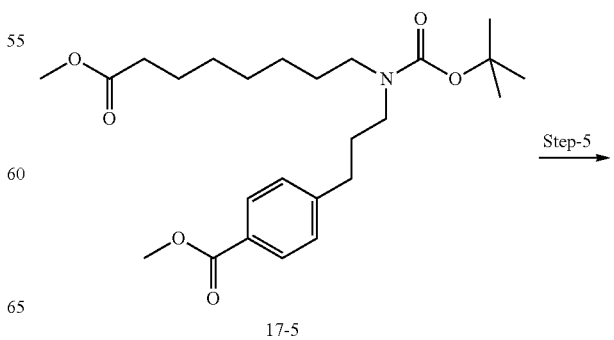

17-5

To a solution of 2.9 g compound 17-4 (1 eq.) in 30 ml of a 1:1 mixture of 1,4-dioxane:H$_2$O were added 2.17 g (BOC)$_2$O (1.2 eq.) and 2.09 g NaHCO$_3$ (3 eq.) at room temperature. The reaction mixture was stirred at room temperature for 12 hours.

Completion of reaction was monitored by TLC, MeOH:DCM, 1:9. Starting material 17-4 intermediate was observed to be absent.

The resulting reaction mixture was diluted with EtOAc (200 ml), washed with H$_2$O (2×100 ml) and concentrated under reduced pressure. The residue obtained upon evaporation of the solvents was purified by silica gel flash column chromatography (2-20% EtOAc in pet ether) to obtain product 17-5 as a pale yellow solid. Quantity produced, 3.3 g; yield, 89%; confirmed by $^1$H NMR and LC-MS.

Lipid 17: Step 5

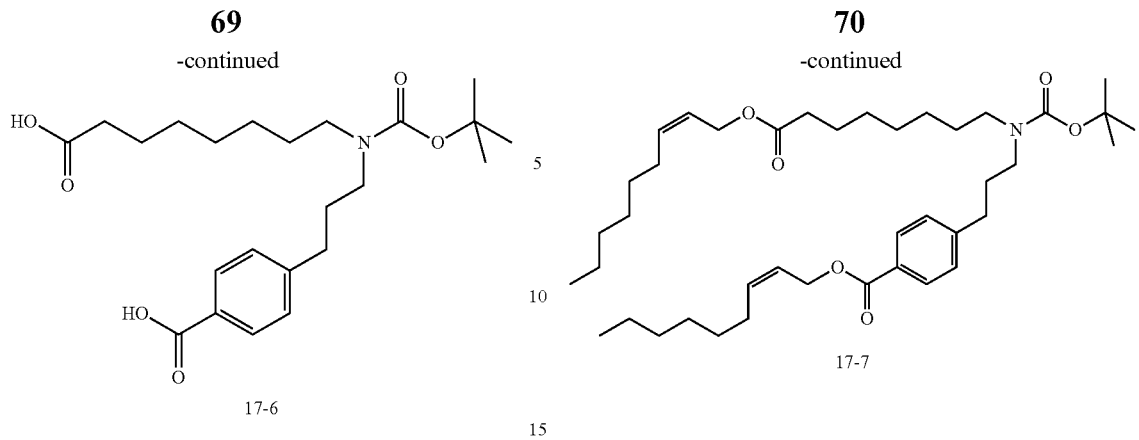

17-6

To a solution of 3.3 g compound 17-5 (1 eq.) in 20 ml of a mixture of MeOH:H$_2$O, 4:1, was added 740 mg NaOH (2.5 eq.) at room temperature. The reaction mixture was stirred at room temperature for 12 hours.

Completion of reaction was monitored by TLC, MeOH: DCM, 1:9. Starting material 17-5 intermediate was observed to be absent.

MeOH was evaporated under reduced pressure, crude reaction mixture was diluted with H$_2$O (20 ml), neutralized with 0.1 N HCl. The aqueous layer was extracted with EtOAc (3×50 ml), the combined EtOAc layer was washed with H$_2$O (50 ml), dried over Na$_2$SO$_4$ and concentrated under reduced pressure. The crude product obtained upon evaporation of the volatiles was purified by silica gel column chromatography (0.5-5% MeOH in DCM) to obtain product 17-6 as pale yellow oil. Quantity produced, 2.8 g; yield, 93%; confirmed by $^1$H NMR and LC-MS Lipid 17: Step 6

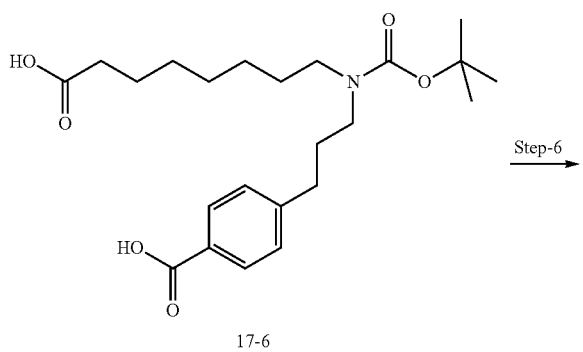

17-6

→ Step-6

To a solution of 2.8 g compound 17-6 (1.0 eq.) in 50 ml DCM were added 7.6 g EDC.HCl (6.0 eq.), 6.8 ml DIPEA (6.0 eq.), 2.8 g cis-2-nonen-1-ol (3.0 eq.), and 324 mg DMAP (0.4 eq.) at 0° C. The reaction mixture was stirred at room temperature for 14 hours.

Completion of reaction was monitored by TLC, MeOH: DCM, 1:9. Starting material 17-6 intermediate was observed to be absent.

Resulting reaction mixture was diluted with DCM (200 ml) and washed with H$_2$O (2×50 ml). The crude product obtained upon evaporation of volatiles was purified through silica gel (230-400) column chromatography (0-2.5% EtOAc in pet ether) to give product 17-7 as a pale yellow oil. Quantity produced, 3.6 g; yield, 64%; confirmed by $^1$H NMR and LC-MS.

Lipid 17: Step 7

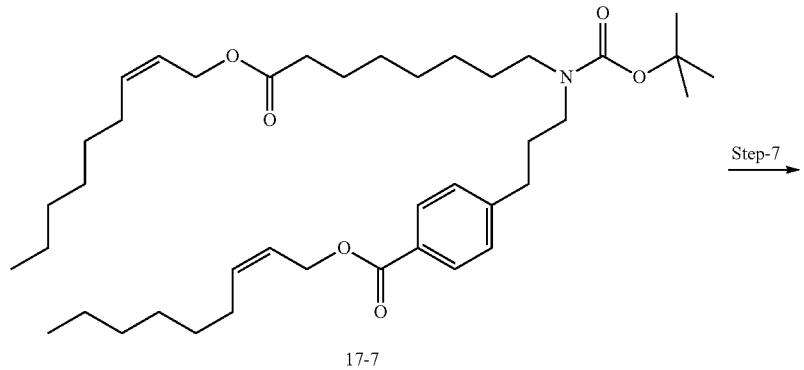

17-7

→ Step-7

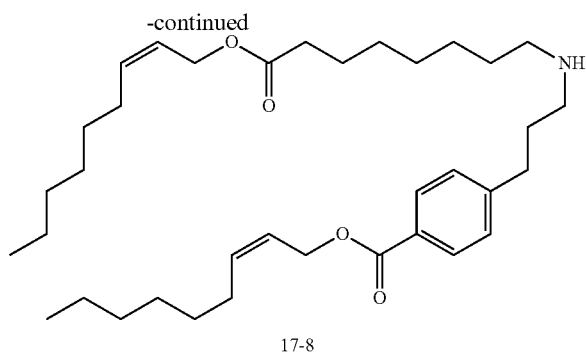

17-8

To a solution of 3.6 g compound 17-7 (1 eq.) in 25 ml DCM was added 7.2 ml TFA (2 vol.) at 0° C. The reaction mixture was stirred at room temperature for 2 hours.

Completion of reaction was monitored by TLC, MeOH: DCM, 1:9. Starting material 17-7 intermediate was observed to be absent.

The resulting reaction mixture was concentrated under reduced pressure, diluted with $H_2O$ (25 ml), neutralized with aqueous $NaHCO_3$. The product was extracted with DCM (2×100 ml) and washed with $H_2O$ (50 ml). The crude product obtained upon evaporation of volatiles was purified through silica gel (230-400) column chromatography (1 to 2.5% MeOH in DCM) to give product 17-8 as a pale yellow oil. Quantity produced, 3.1 g; yield, 91%; confirmed by $^1H$ NMR and LC-MS.

Lipid 17: Step 8

Completion of reaction was monitored by TLC, 100% EtOAc. Starting material N—COCl intermediate was observed to be absent.

The resulting solution was concentrated under nitrogen atmosphere, again diluted with 30 ml DCM, added 3.7 g 2-(dimethylamino)ethanethiol hydrochloride (5 eq.) and 5.87 ml TEA (8 eq.) at 0° C. The reaction mixture was stirred at room temperature for 48 hours.

Completion of reaction was monitored by TLC, 100% EtOAc. Starting material N—COCl intermediate was observed to be absent.

The resulting reaction mixture was diluted with DCM (250 ml), washed with $H_2O$ (2×50 ml), organic layer was dried and concentrated under reduced pressure. The crude product obtained upon evaporation of volatiles was purified through silica gel (230-400 mesh) column chromatography

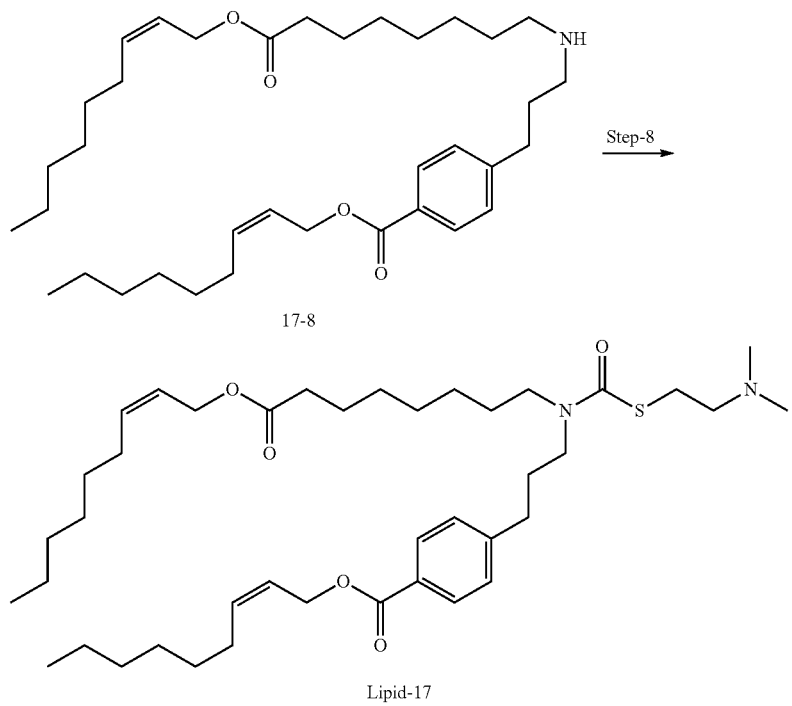

To a solution 3.0 g 17-8 (1 eq.) and 2.13 ml TEA (2 eq.) in 30 ml DCM was added 1.40 g triphosgene (0.9 eq.) at 0° C. The resulting reaction mixture was stirred at room temperature for 2 hours.

(25-95% EtOAc in pet ether) to give product Lipid 17 as a pale yellow oil. Quantity produced, 0.9 g; yield, 30%; confirmed by $^1H$ NMR and LC-MS; HPLC purity, >99%.

$^1$H-NMR, Lipid 17 (400 MHz, $CDCl_3$) δ=7.92 (d, J=7.2, 2), 7.23 (d, J=7.2, 2), 5.67 (m, 2), 5.52 (m, 2), 4.86 (d, J=6.0, 2), 4.60 (d, J=6.0, 2), 3.18-3.42 (4), 3.00 (t, J=7.0, 2), 2.66 (m, 2), 2.55 (t, J=7.0, 2), 2.27 (s, 6), 2.20-2.30 (2), 2.00-2.18 (4), 1.80-2.00 (2), 1.20-1.65 (26), 0.82-0.90 (6)

Example 7: Synthesis of Lipid 18

Figure 7:
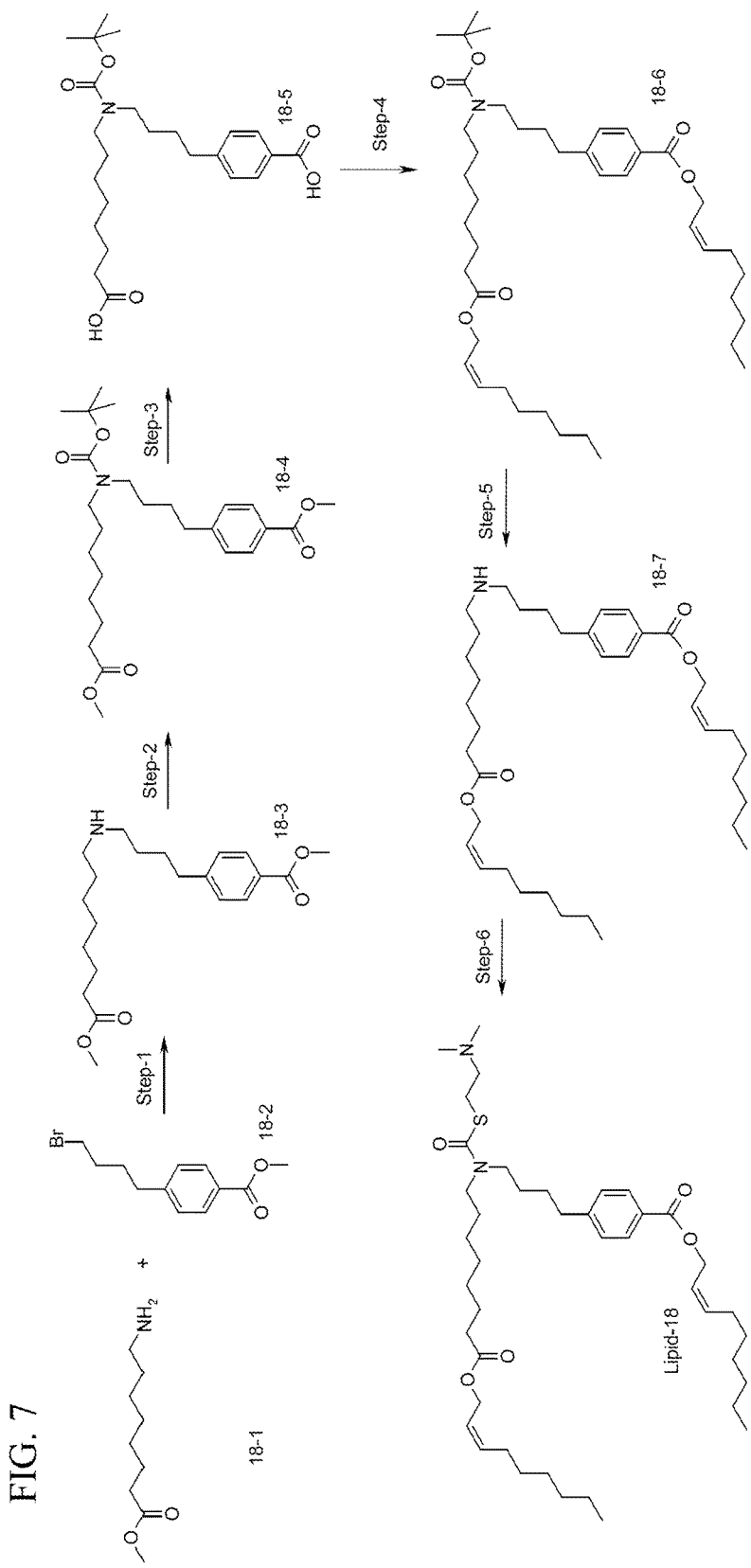
FIG. 7 shows the preparation of Lipid 18, showing intermediates 18-1 to 18-7. 18-1 and 18-2 are commercial starting materials. The reactions are described in detail in Example 7.

Lipid 18 was synthesized in eight steps as shown in FIG. 7.

Lipid 18: Step 1

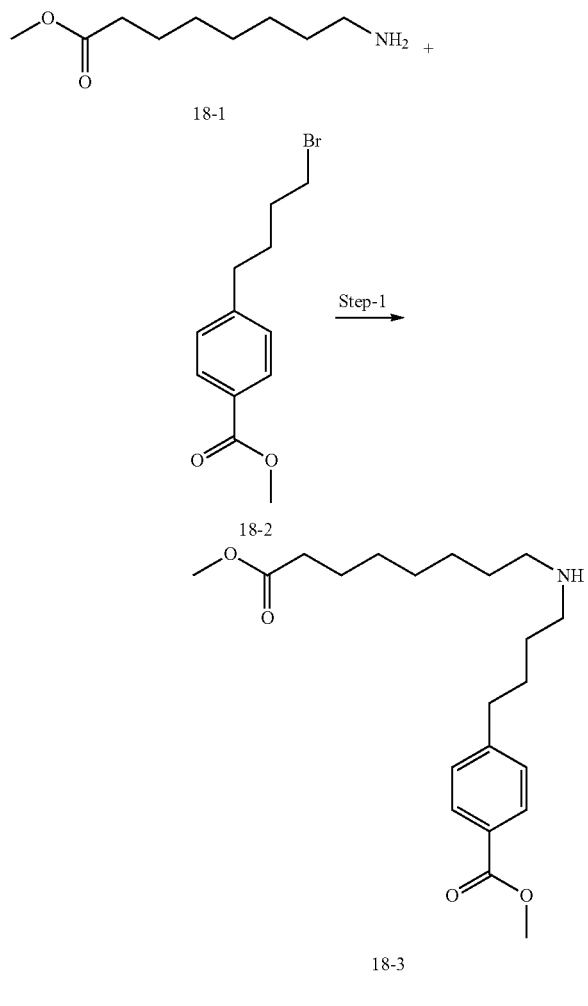

Lipid 18: Step-2

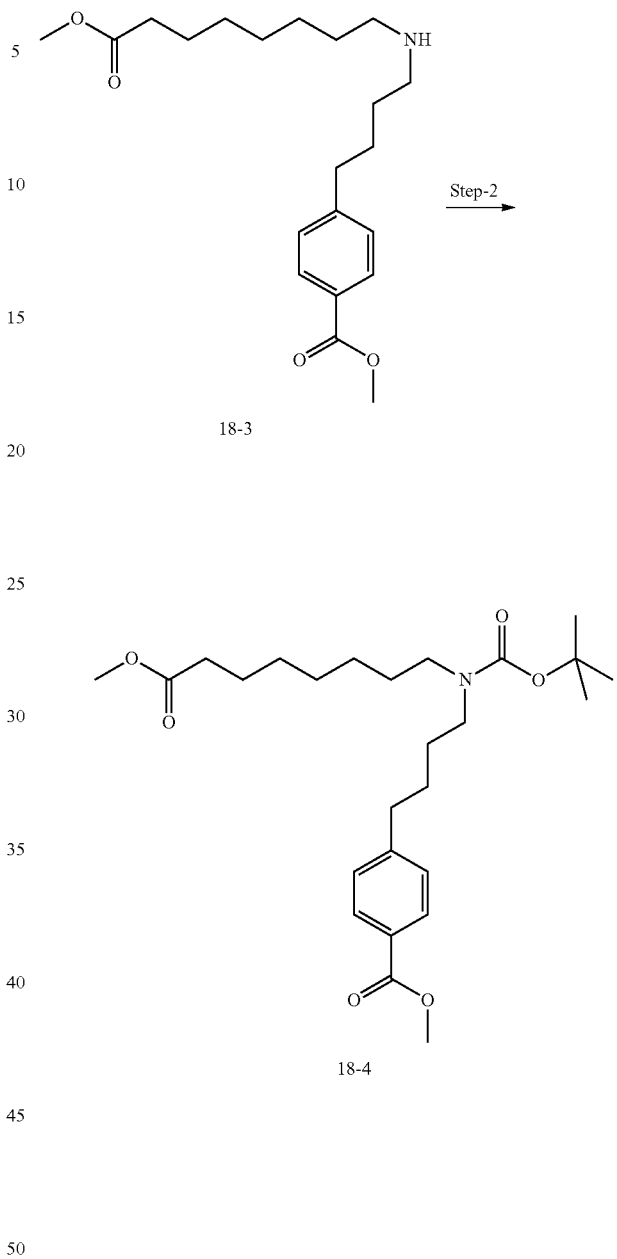

To a solution of 13.9 g amine hydrochloride 18-1 (1 eq.) in 200 ml ACN were added 27.5 g K$_2$CO$_3$ (3 eq.) and 18.0 g compound 18-2 (1 eq.) at room temperature. The reaction mixture was stirred at room temperature for 16 hours.

Completion of reaction was monitored by TLC, MeOH: DCM, 1:9. Starting material 18-1 intermediate was observed to be absent.

Resulting reaction mixture was filtered to remove insoluble salts, diluted with EtOAc (500 ml), washed with H$_2$O (2×100 ml) and concentrated. The crude product obtained upon evaporation of volatiles was purified through silica gel (230-400 mesh) column chromatography (0.2-1% MeOH in DCM) to give product 18-3 as a pale yellow oil. Quantity produced, 7.3 g; yield, 38%; confirmed by $^1$H NMR and LC-MS.

To a solution of 7.3 g compound 18-3 (1 eq.) in 40 ml of a 1:1 mixture of 1,4-dioxane:H$_2$O were added 5.2 g (BOC)$_2$O (1.2 eq.) and 5.0 g NaHCO$_3$ (3 eq.) at room temperature. The reaction mixture was stirred at room temperature for 12 hours.

Completion of reaction was monitored by TLC, EtOAc: hexane, 2:8. Starting material 18-3 intermediate was observed to be absent.

The resulting reaction mixture was diluted with EtOAc (250 ml), washed with H$_2$O (2×100 ml) and concentrated under reduced pressure. The residue obtained upon evaporation of the solvents was purified by silica gel flash column chromatography (1-5% EtOAc in pet ether) to obtain product 18-4 as a pale yellow solid. Quantity produced, 7.9 g; yield, 84%; confirmed by $^1$H NMR and LC-MS.

Lipid 18: Step-3

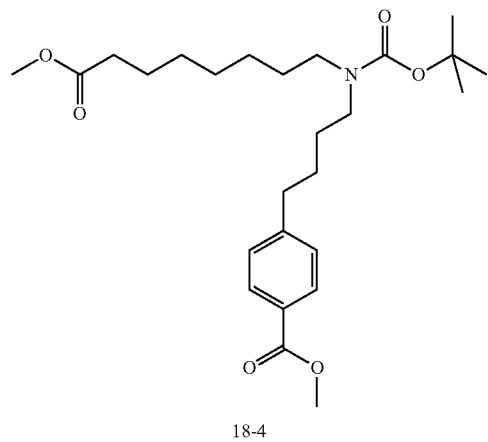

18-4

Step-3 →

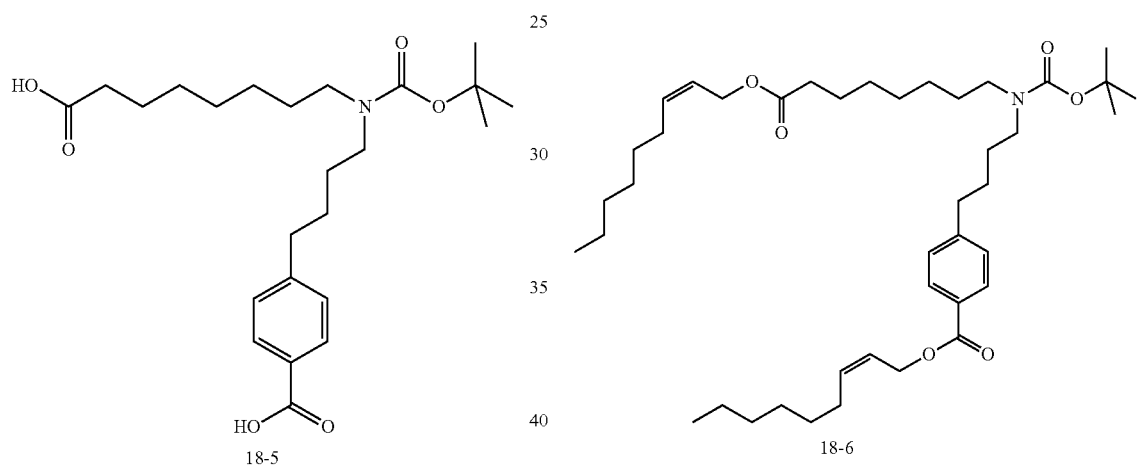

18-5

Lipid 18: Step-4

18-5

Step-4 →

18-6

To a solution of 7.9 g compound 18-4 (1.0 eq.) in 80 ml of MeOH:H$_2$O, 4:1, was added 1.7 g NaOH (2.5 eq.) at room temperature. The reaction mixture was stirred at room temperature for 12 hours.

Completion of reaction was monitored by TLC, MeOH: DCM, 1:9. Starting material 18-4 intermediate was observed to be absent.

MeOH was evaporated under reduced pressure, crude reaction mixture was diluted with H$_2$O (50 ml), neutralized with 0.1 N HCl. Then aqueous layer was extracted with EtOAc (3×150 ml), the combined EtOAc layer was washed with H$_2$O (100 ml), dried over Na$_2$SO$_4$ and concentrated under reduced pressure. The crude product obtained upon evaporation of the volatiles was purified by silica gel column chromatography (0.5-5% MeOH in DCM) to obtain product 18-5 as pale yellow oil. Quantity produced, 7.0 g; yield, 94%; confirmed by $^1$H NMR To a solution of 7.0 g compound 18-5 (1.0 eq.) in 70 ml DCM were added 18.4 g EDC.HCl (6.0 eq.), 16.5 g DIPEA (6 eq.), 6.79 g cis-2-nonen-1-ol (3.0 eq.) and 784 mg DMAP (0.4 eq.) at 0° C. The reaction mixture was stirred at room temperature for 14 hours.

Completion of reaction was monitored by TLC, EtOAc: hexane, 1:9. Starting material 18-5 intermediate was observed to be absent.

Resulting reaction mixture was diluted with DCM (500 ml) and washed with H$_2$O (2×100 ml). The crude product obtained upon evaporation of volatiles was purified through silica gel (230-400 mesh) column chromatography (1-5% EtOAc in pet ether) to give product 18-6 as a pale yellow oil. Quantity produced, 7.0 g; yield, 63%; confirmed by $^1$H NMR and LC-MS.

Lipid 18: Step-5

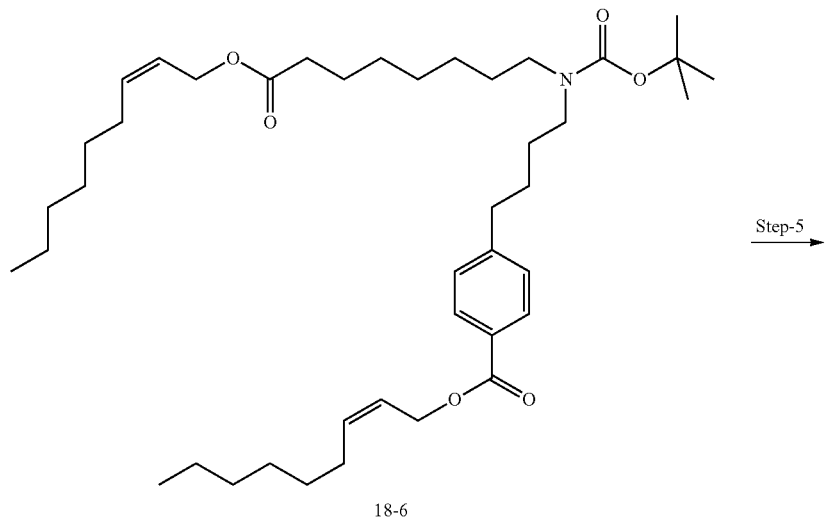

18-6

18-7

To a solution of 7.0 g compound 18-6 (1 eq.) in 35 ml DCM was added 15 ml TFA (2 vol.) at 0° C. The reaction mixture was stirred at room temperature for 2 hours.

Completion of reaction was monitored by TLC, MeOH:DCM, 1:9. Starting material 18-6 intermediate was observed to be absent.

The resulting reaction mixture was concentrated under reduced pressure, diluted with $H_2O$ (50 ml), neutralized with aqueous $Na_2CO_3$. The product was extracted with DCM (2×100 ml) and washed with $H_2O$ (50 ml). The crude product obtained upon evaporation of volatiles was purified through silica gel (230-400 mesh) column chromatography (0.2-4% MeOH in DCM) to give product 18-7 as a pale yellow oil. Quantity produced, 5.4 g; yield, 91%; confirmed by $^1H$ NMR and LC-MS.

Lipid 18: Step-6

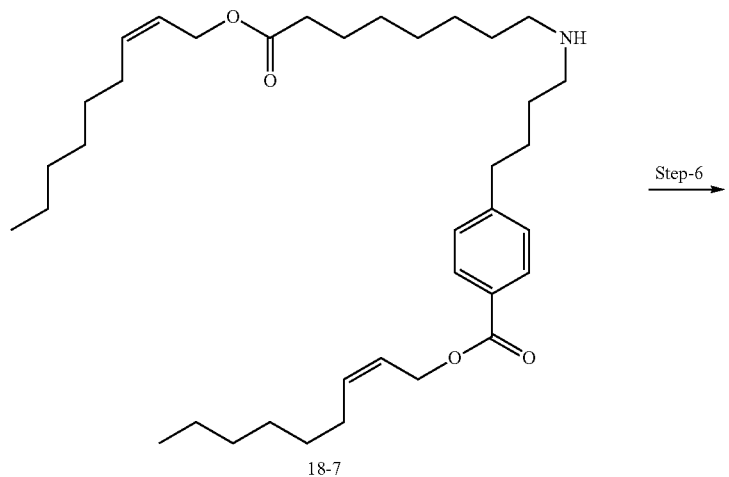

18-7

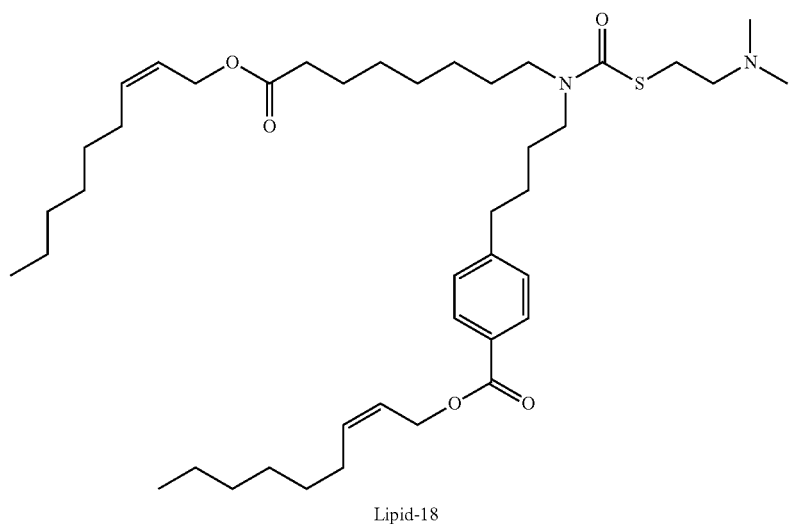

Lipid-18

To a solution of 5.4 g 18-7 (1.0 eq.) and 2.57 ml TEA (2.0 eq.) in 50 ml DCM was added 2.46 g triphosgene (0.9 eq.) at 0° C. The resulting reaction mixture was stirred at room temperature for 2 hours.

Completion of reaction was monitored by TLC, 100% EtOAc. Starting material N—COCl intermediate was observed to be absent.

The resulting solution was concentrated under nitrogen atmosphere, again diluted with 50 ml DCM, added 6.4 g 2-(dimethylamino)ethanethiol hydrochloride (5.0 eq.) and 10.25 ml TEA (8.0 eq.) at 0° C. The reaction mixture was stirred at room temperature for 48 hours.

Completion of reaction was monitored by TLC, 100% EtOAc. Starting material N—COCl intermediate was observed to be absent.

The resulting reaction mixture was diluted with DCM (500 ml), washed with $H_2O$ (2×250 ml), organic layer was dried and concentrated under reduced pressure. The crude product obtained upon evaporation of volatiles was purified through silica gel (230-400 mesh) column chromatography (25-90% EtOAc in pet ether) to give product Lipid 18 as a pale yellow oil. Quantity produced, 1.0 g; yield, 16%; confirmed by $^1$H NMR and LC-MS; HPLC purity, >95%.

$^1$H-NMR, Lipid 18 (400 MHz, $CDCl_3$) δ=7.85 (d, J=6.4, 2), 7.20 (d, J=6.4, 2), 5.67 (m, 2), 5.51 (m, 2), 4.84 (d, J=5.3, 2), 4.61 (d, J=5.3, 2), 3.10-3.32 (4), 3.01 (t, J=7.0, 2), 2.67 (m, 2), 2.53 (t, J=7.0, 2), 2.27 (s, 6), 2.20-2.33 (2), 2.00-2.20 (4), 1.70-1.85 (2), 1.15-1.60 (28), 0.81-0.91 (6).

Example 8: Synthesis of Lipid 19

Figure 8:
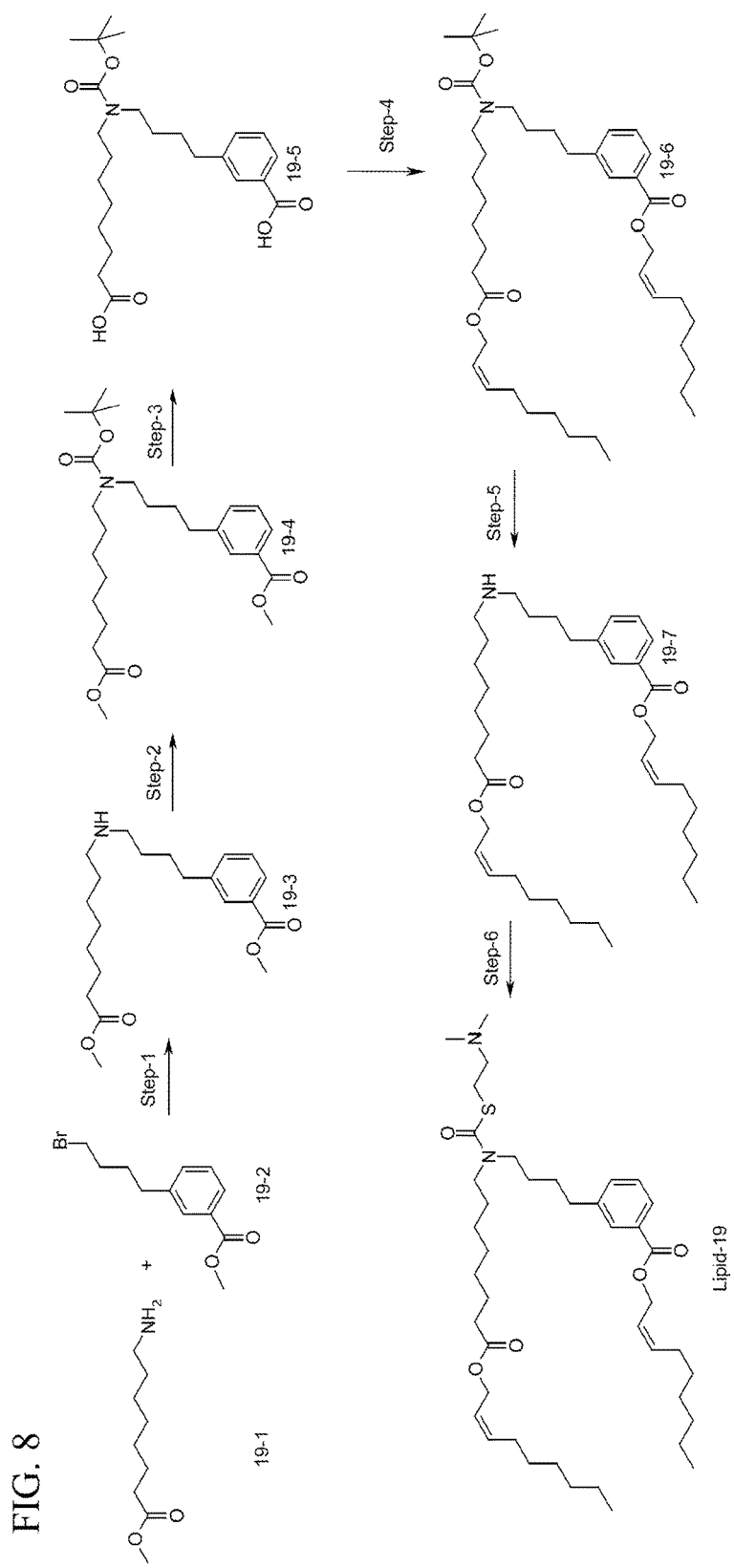
FIG. 8 shows the preparation of Lipid 19, showing intermediates 19-1 to 19-7. 19-1 and 19-2 are commercial starting materials. The reactions are described in detail in Example 8.

Lipid 19 was synthesized in six steps as shown in FIG. 8.

Lipid 19: Step 1

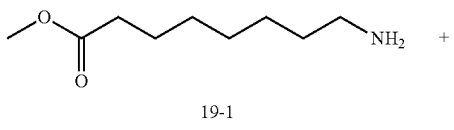

19-1

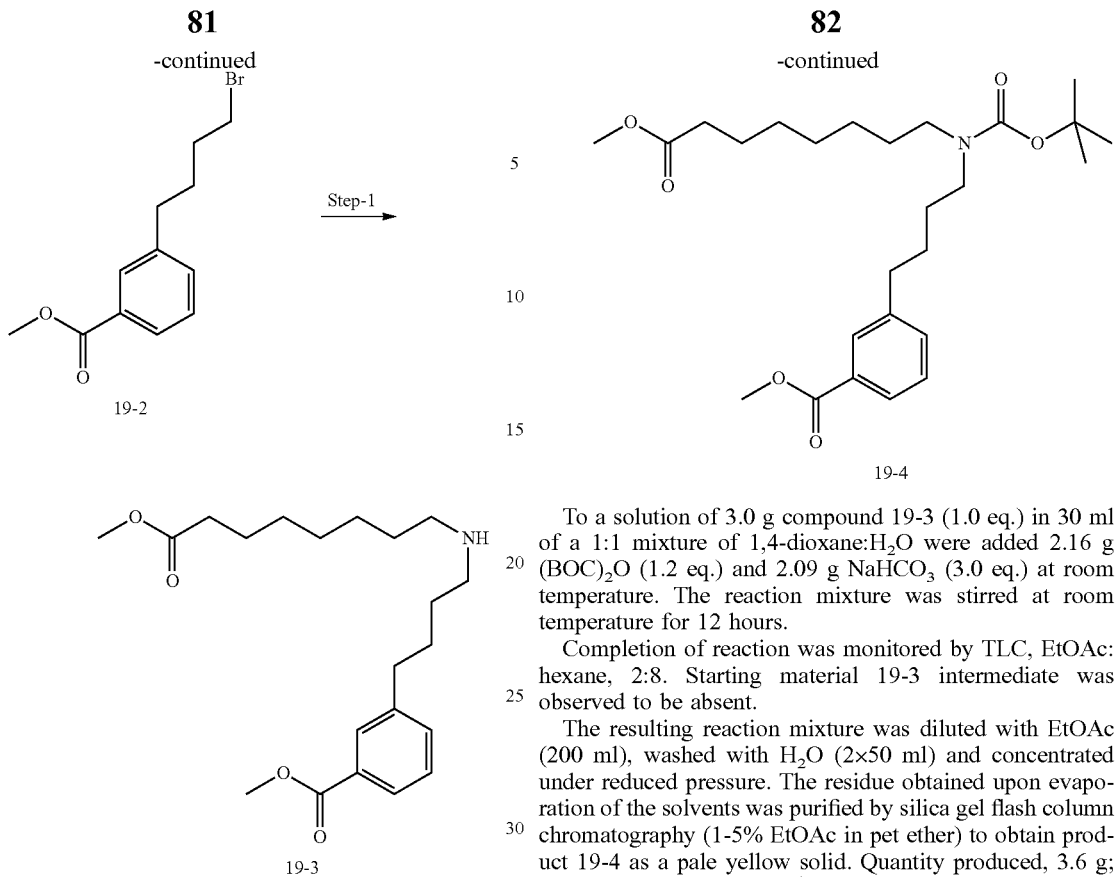

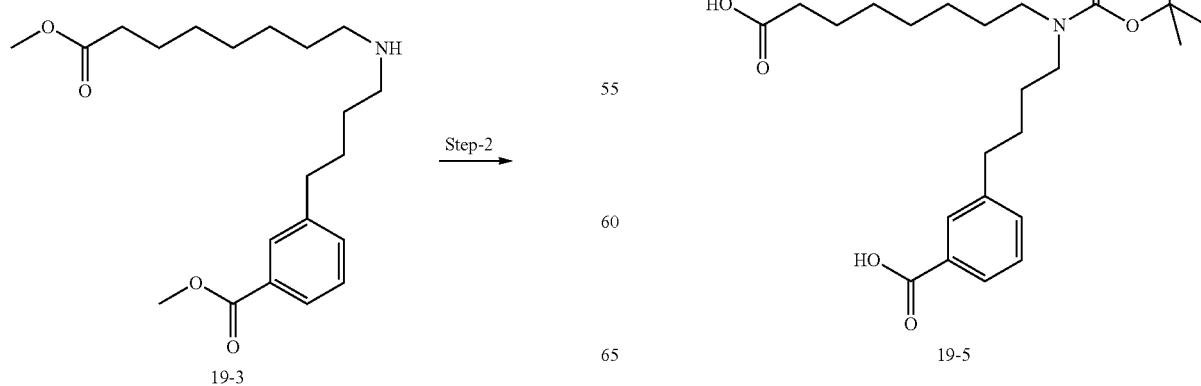

To a solution of 5.0 g amine hydrochloride 19-1 (1 eq.) in 50 ml ACN were added 9.88 g K₂CO₃ (3 eq.) and 6.45 g compound 19-2 (1 eq.) at room temperature. The reaction mixture was stirred at room temperature for 16 hours.

Completion of reaction was monitored by TLC, MeOH:DCM, 1:9. Starting material 19-1 intermediate was observed to be absent.

Resulting reaction mixture was diluted with EtOAc (500 ml), washed with H₂O (2×100 ml) and concentrated. The crude product obtained upon evaporation of volatiles was purified through silica gel (230-400 mesh) column chromatography (0.2-2% MeOH in DCM) to give product 19-3 as a pale yellow oil. Quantity produced, 3.0 g; yield, 34%; confirmed by ¹H NMR and LC-MS.

Lipid 19: Step-2

To a solution of 3.0 g compound 19-3 (1.0 eq.) in 30 ml of a 1:1 mixture of 1,4-dioxane:H₂O were added 2.16 g (BOC)₂O (1.2 eq.) and 2.09 g NaHCO₃ (3.0 eq.) at room temperature. The reaction mixture was stirred at room temperature for 12 hours.

Completion of reaction was monitored by TLC, EtOAc:hexane, 2:8. Starting material 19-3 intermediate was observed to be absent.

The resulting reaction mixture was diluted with EtOAc (200 ml), washed with H₂O (2×50 ml) and concentrated under reduced pressure. The residue obtained upon evaporation of the solvents was purified by silica gel flash column chromatography (1-5% EtOAc in pet ether) to obtain product 19-4 as a pale yellow solid. Quantity produced, 3.6 g; yield, 94%; confirmed by ¹H NMR and LC-MS.

Lipid 19: Step-3

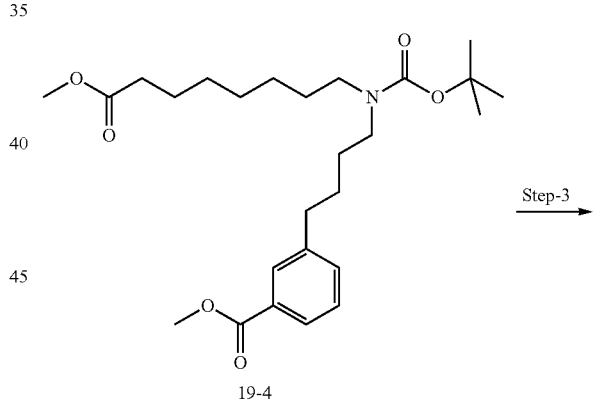

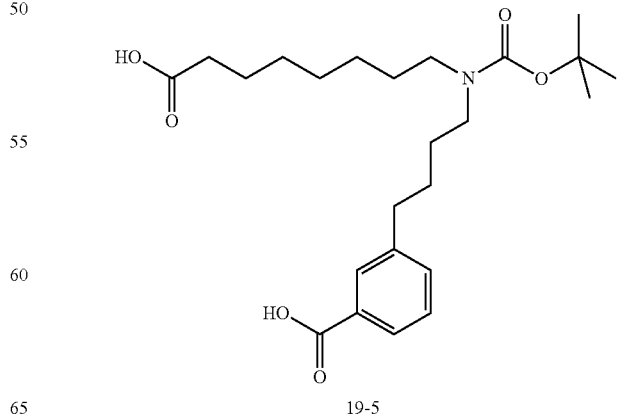

To a solution of 3.6 g compound 19-4 (1.0 eq.) in 40 ml of a mixture of MeOH:H₂O, 4:1, was added 776 mg NaOH (2.5 eq.) at room temperature. The reaction mixture was stirred at room temperature for 12 hours.

Completion of reaction was monitored by TLC, MeOH: DCM, 1:9. Starting material 19-4 intermediate was observed to be absent.

MeOH was evaporated under reduced pressure, crude reaction mixture was diluted with H₂O (20 ml), neutralized with 0.1 N HCl. The aqueous layer was extracted with EtOAc (3×100 ml), the combined EtOAc layer was washed with H₂O (50 ml), dried over Na₂SO₄ and concentrated under reduced pressure. The crude product obtained upon evaporation of the volatiles was purified by silica gel column chromatography (0.2-2% MeOH in DCM) to obtain product 19-5 as a pale yellow oil. Quantity produced, 3.0 g; yield, 85%; confirmed by ¹H NMR and LC-MS.

Lipid 19: Step-4

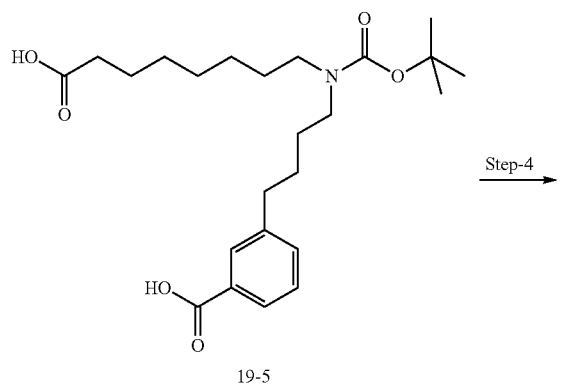

19-5

Step-4 →

-continued

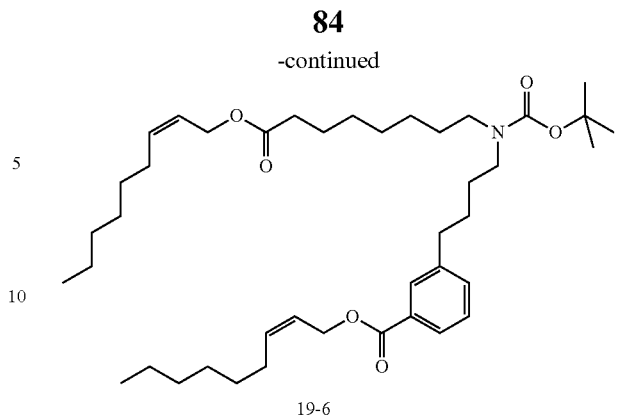

19-6

To a solution of 3.0 g compound 19-5 (1.0 eq.) in 30 ml DCM were added 7.93 g EDC.HCl (6.0 eq.), 7.12 g DIPEA (6.0 eq.), 2.93 g cis-2-nonen-1-ol (3.0 eq.), and 336 mg MOPE (0.4 eq.) at 0° C. The reaction mixture was stirred at room temperature for 14 hours.

Completion of reaction was monitored by TLC, EtOAc: hexane, 1:9. Starting material 19-5 intermediate was observed to be absent.

Resulting reaction mixture was diluted with DCM (200 ml) and washed with H₂O (2×50 ml). The crude product obtained upon evaporation of volatiles was purified through silica gel (230-400 mesh) column chromatography (0-5% EtOAc in pet ether) to give product 19-6 as a pale yellow oil. Quantity produced, 4.0 g; yield, 85%; confirmed by ¹H NMR and LC-MS.

Lipid 19: Step-5

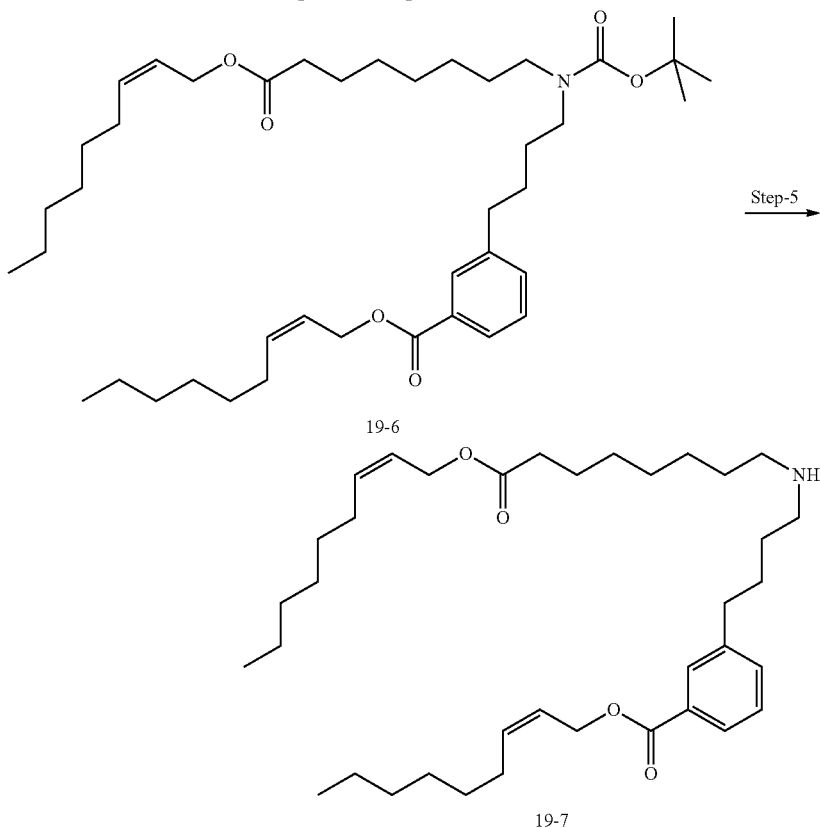

To a solution of 4.0 g compound 19-6 (1 eq.) in 20 ml DCM was added 8 ml TFA (2 vol.) at 0° C. The reaction mixture was stirred at room temperature for 2 hours.

Completion of reaction was monitored by TLC, MeOH:DCM, 1:9. Starting material 19-6 intermediate was observed to be absent.

The resulting reaction mixture was concentrated under reduced pressure, diluted with H$_2$O (25 ml), neutralized with aq. Na$_2$CO$_3$. The product was extracted with DCM (2×100 ml) and washed with H$_2$O (50 ml). The crude product obtained upon evaporation of volatiles was purified through silica gel (230-400 mesh) column chromatography (0-2% MeOH in DCM) to give product 19-7 as a pale yellow oil. Quantity produced, 3.0 g; yield, 88%; confirmed by $^1$H NMR and LC-MS.

Lipid 19: Step-6

Completion of reaction was monitored by TLC, 100% EtOAc. Starting material N—COCl intermediate was observed to be absent.

The resulting reaction mixture was diluted with DCM (500 ml), washed with H$_2$O (2×100 ml), organic layer was dried and concentrated under reduced pressure. The crude product obtained upon evaporation of volatiles was purified through silica gel (230-400 mesh) column chromatography (25-95% EtOAc in pet ether) to give product Lipid 19 as a pale yellow oil. Quantity produced, 1.0 g; yield, 27%; confirmed by $^1$H NMR and LC-MS; HPLC purity, >96%.

$^1$H-NMR, Lipid 19 (400 MHz, CDCl$_3$) δ=7.85-7.92 (2), 7.30-7.40 (2), 5.70 (m, 2), 5.52 (m, 2), 4.88 (m, 2), 4.61 (m, 2), 3.14-3.42 (4), 3.02 (t, J=7.0, 2), 2.68 (m, 2), 2.53 (t, J=7.0, 2), 2.26 (s, 6), 2.22-2.31 (2), 2.04-2.21 (4), 1.45-1.64 (4), 1.17-1.44 (26), 0.82-0.91 (6).

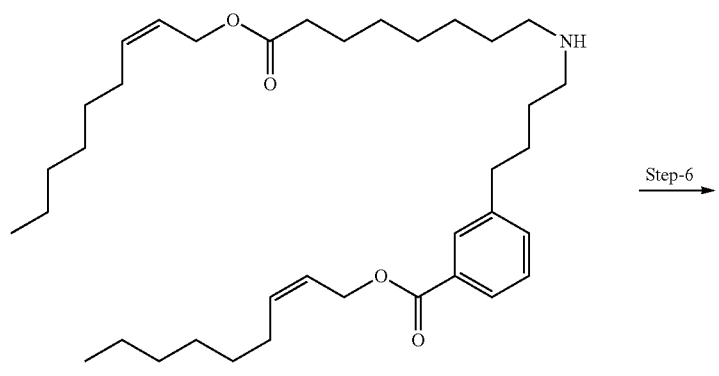

19-7

Step-6

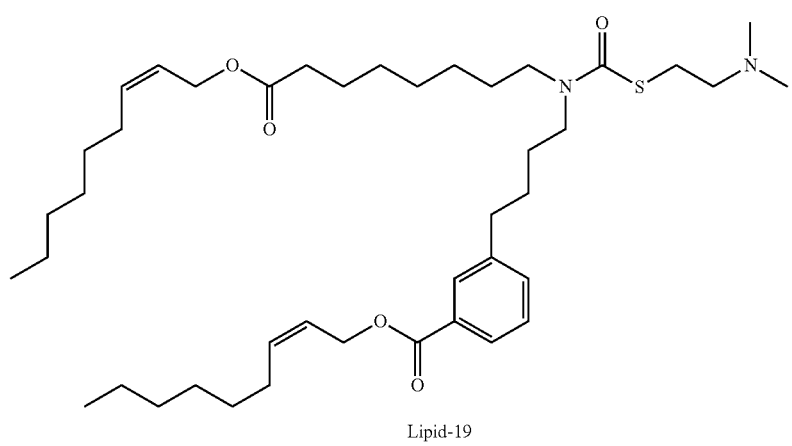

Lipid-19

To a solution of 3.0 g 19-7 (1.0 eq.) and 1.44 ml TEA (2.0 eq.) in 15 ml DCM was added 1.36 g triphosgene (0.9 eq.) at 0° C. The resulting reaction mixture was stirred at room temperature for 2 hours.

Completion of reaction was monitored by TLC, 100% EtOAc. Starting material N—COCl intermediate was observed to be absent.

The resulting solution was concentrated under nitrogen atmosphere, again diluted with 30 ml DCM added 3.6 g 2-(dimethylamino)ethanethiol hydrochloride (5.0 eq.) and 5.75 ml TEA (8.0 eq.) at 0° C. The reaction mixture was stirred at room temperature for 48 hours.

Example 9: Synthesis of Lipid 20

Figure 9:
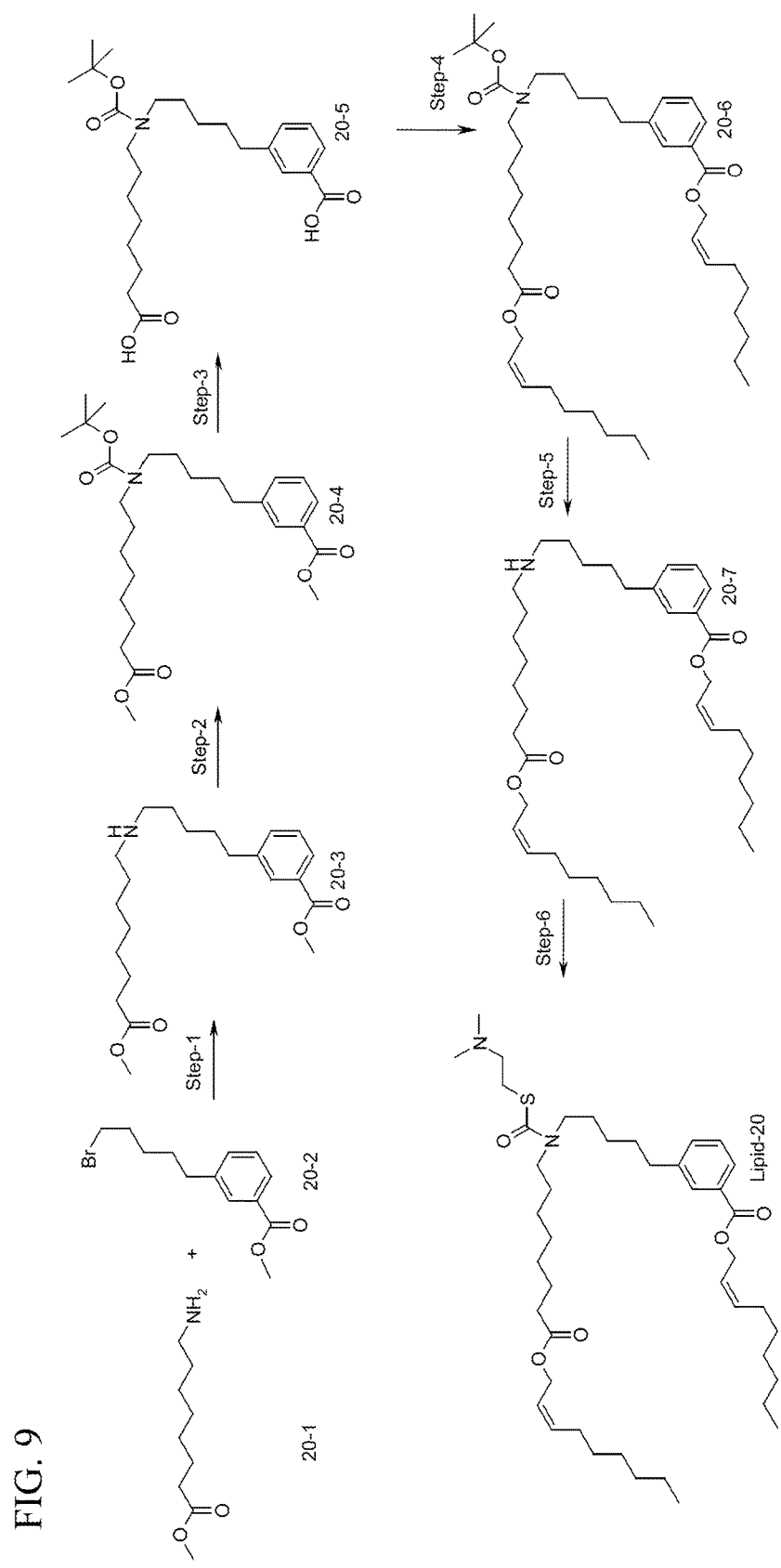
FIG. 9 shows the preparation of Lipid 20, showing intermediates 20-1 to 20-7. 20-1 and 20-2 are commercial starting materials. The reactions are described in detail in Example 9.

Lipid 20 was synthesized in six steps as shown in FIG. 9.

Lipid 20: Step 1

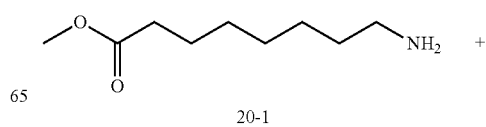

20-1

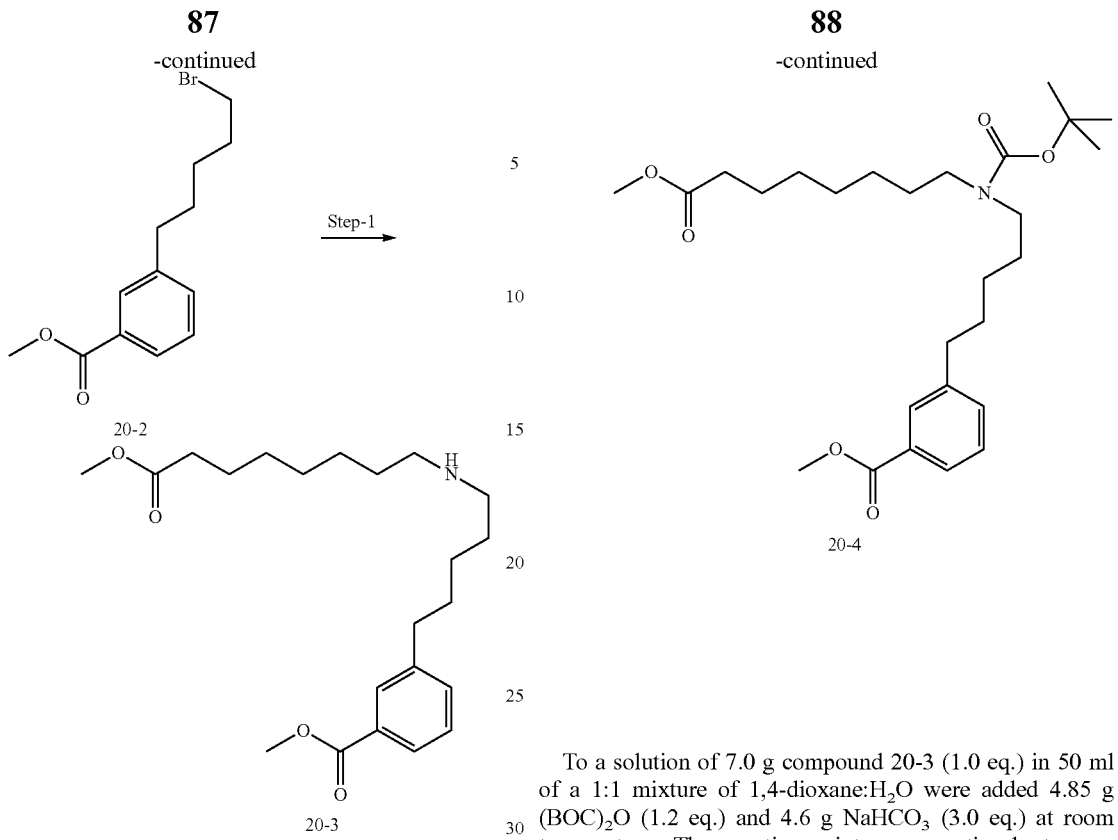

To a solution of 10.0 g amine, hydrochloride salt, 20-1 (1 eq.) in 500 ml ACN were added 20.13 ml K₂CO₃ (3 eq.) and 13.6 g compound 20-2 (1 eq.) at room temperature. The reaction mixture was stirred at room temperature for 16 hours.

Completion of reaction was monitored by TLC, MeOH: DCM, 1:9. Starting material 20-1 intermediate was observed to be absent.

Resulting reaction mixture was diluted with EtOAc (1,000 ml), washed with H₂O (2×100 ml) and concentrated. The crude product obtained upon evaporation of volatiles was purified through silica gel (230-400 mesh) column chromatography (0.2-2% MeOH in DCM) to give product 20-3 as a pale yellow oil. Quantity produced, 7.0 g; yield, 38%; confirmed by $^1$H NMR and LC-MS.

Step-2:

To a solution of 7.0 g compound 20-3 (1.0 eq.) in 50 ml of a 1:1 mixture of 1,4-dioxane:H₂O were added 4.85 g (BOC)₂O (1.2 eq.) and 4.6 g NaHCO₃ (3.0 eq.) at room temperature. The reaction mixture was stirred at room temperature for 12 hours.

Completion of reaction was monitored by TLC, EtOAc: hexane, 2:8. Starting material 20-3 intermediate was observed to be absent.

The resulting reaction mixture was diluted with EtOAc (500 ml), washed with H₂O (2×100 ml) and concentrated under reduced pressure. The residue obtained upon evaporation of the solvents was purified by silica gel flash column chromatography (0-5% EtOAc in pet ether) to obtain product 20-4 as a pale yellow solid. Quantity produced, 8.0 g; yield, 90%; confirmed by $^1$H NMR and LC-MS.

Step-3:

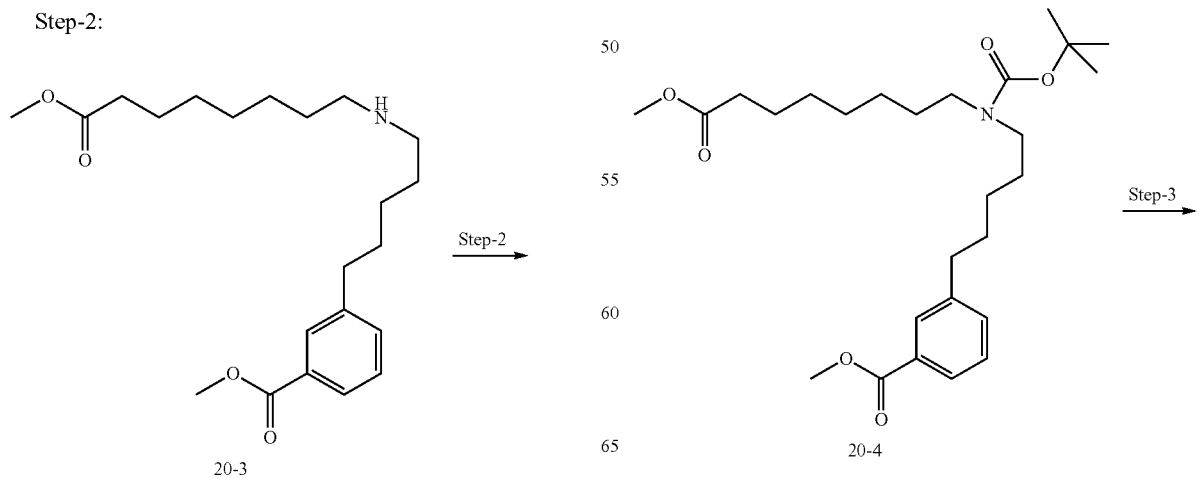

-continued

Step-4:

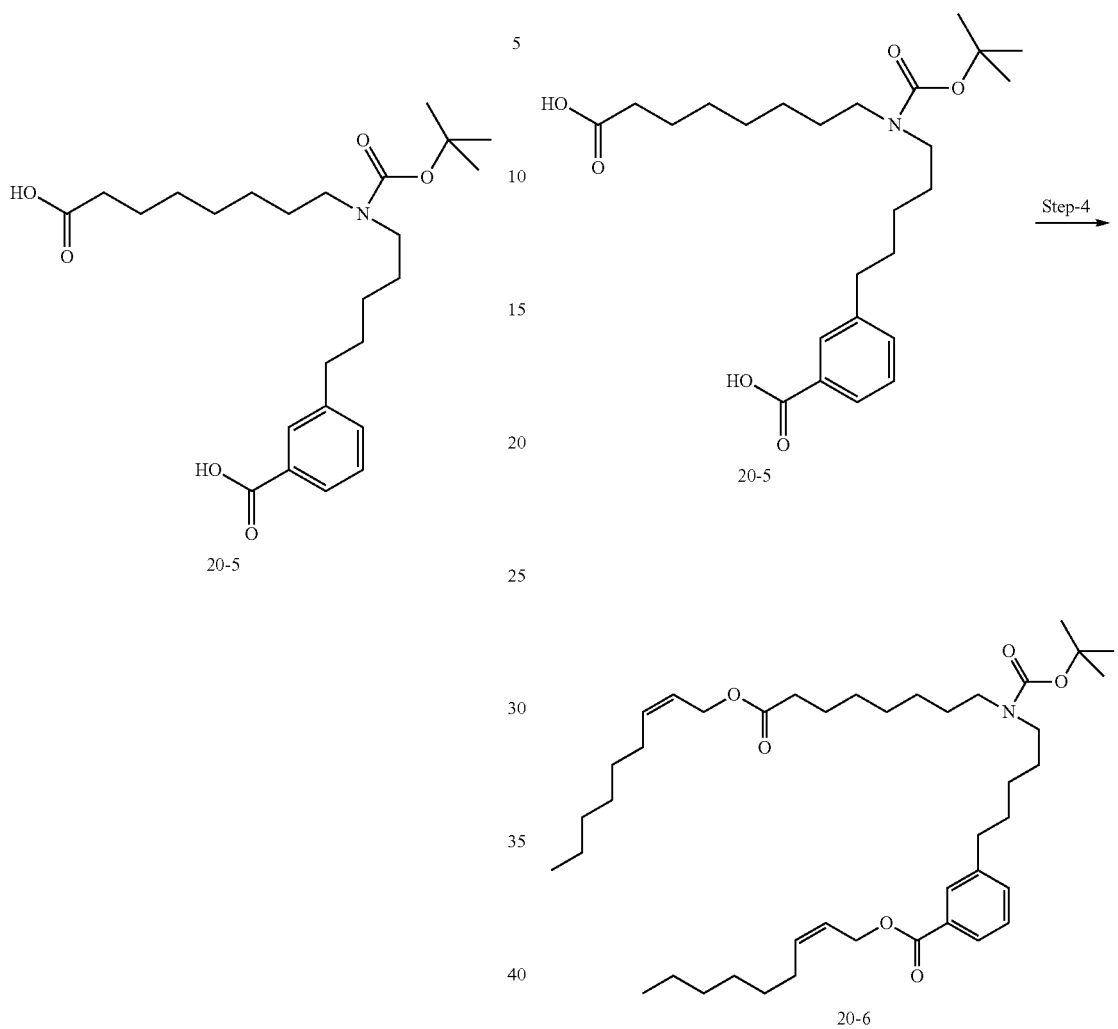

To a solution of 8.0 g compound 20-4 (1.0 eq.) in 80 ml of a mixture of MeOH—H$_2$O (7:3,) was added 1.6 g NaOH (2.5 eq.) at room temperature. The reaction mixture was stirred at room temperature for 12 hours.

Completion of reaction was monitored by TLC, MeOH: DCM, 1:9. Starting material 20-4 intermediate was observed to be absent.

MeOH was evaporated under reduced pressure, crude reaction mixture was diluted with H$_2$O (50 ml), neutralized with 0.1 N HCl. The aqueous layer was extracted with EtOAc (3×150 ml), the combined EtOAc layer was washed with H$_2$O (50 ml), dried over Na$_2$SO$_4$ and concentrated under reduced pressure. The crude product obtained upon evaporation of the volatiles was purified by silica gel column chromatography (0-3% MeOH in DCM) to obtain product 20-5 as pale yellow oil. Quantity produced, 7.0 g; yield, 93%; confirmed by $^1$H NMR and LC-MS To a solution of 7.0 g compound 20-5 (1.0 eq.) in 70 ml DCM were added 17.9 g EDC.HCl (6.0 eq.), 16.06 ml DIPEA (6.0 eq.), 6.65 g cis-2-nonen-1-ol (3.0 eq.) and 760 mg DMAP (0.4 eq.) at 0° C. The reaction mixture was stirred at room temperature for 14 hours.

Completion of reaction was monitored by TLC, EtOAc: hexane, 1:9. Starting material 20-5 intermediate was observed to be absent.

Resulting reaction mixture was diluted with DCM (500 ml) and washed with H$_2$O (2×150 ml). The crude product obtained upon evaporation of volatiles was purified through silica gel (230-400 mesh) column chromatography (0-3% EtOAc in pet ether) to give product 20-6 as a pale yellow oil. Quantity produced, 6.0 g; yield, 60%; confirmed by $^1$H NMR and LC-MS.

Step-5:

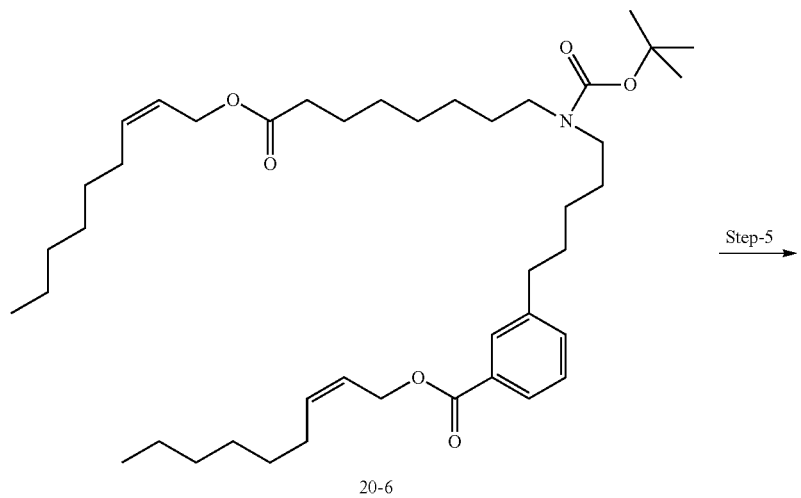

20-6

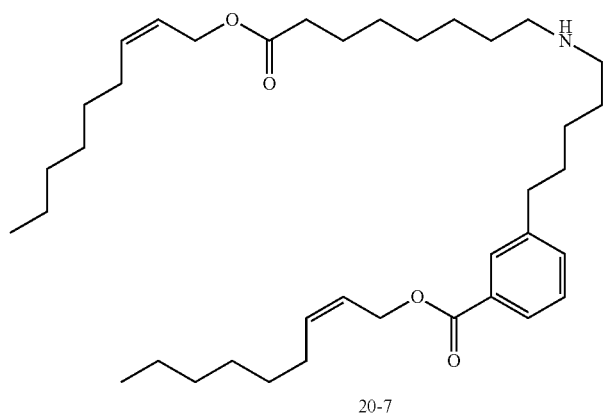

20-7

To a solution of 6.0 g compound 20-6 (1 eq.) in 25 ml DCM was added 12 ml TFA (2 vols.) at 0° C. The reaction mixture was stirred at room temperature for 2 hours.

Completion of reaction was monitored by TLC, MeOH: DCM, 1:9. Starting material 20-6 intermediate was observed to be absent.

The resulting reaction mixture was concentrated under reduced pressure, diluted with $H_2O$ (50 ml), neutralized with aq. $Na_2CO_3$. The product was extracted with DCM (2×250 ml) and washed with $H_2O$ (50 ml). The crude product obtained upon evaporation of volatiles was purified through silica gel (230-400 mesh) column chromatography (0-2% MeOH in DCM) to give product 20-7 as a pale yellow oil. Quantity produced, 5.1 g; yield, 76%; confirmed by $^1H$ NMR and LC-MS.

Step-6:

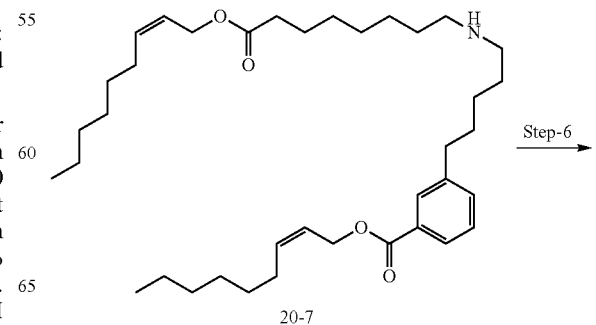

20-7

Lipid-20

To a 5.0 g solution 20-7 (1.0 eq.) and 2.34 ml TEA (2.0 eq.) in 50 ml DCM was added 2.2 g triphosgene (0.9 eq.) at 0° C. The resulting reaction mixture was stirred at room temperature for 2 hours.

Completion of reaction was monitored by TLC, 100% EtOAc. Starting material N—COCl intermediate was observed to be absent.

The resulting solution was concentrated under nitrogen atmosphere, again diluted with 100 ml DCM, added 5.8 g 2-(dimethylamino)ethanethiol hydrochloride (5.0 eq.) and 9.3 ml TEA (8.0 eq.) at 0° C. The reaction mixture was stirred at room temperature for 48 hours.

Completion of reaction was monitored by TLC, 100% EtOAc. Starting material N—COCl intermediate was observed to be absent.

The resulting reaction mixture was diluted with DCM (500 ml), washed with $H_2O$ (2×100 ml), organic layer was dried and concentrated under reduced pressure. The crude product obtained upon evaporation of volatiles was purified through silica gel (230-400 mesh) column chromatography (20-100% MeOH in DCM) to give product Lipid 20 as a pale yellow oil. Quantity produced, 1.2 g; yield, 27%; confirmed by $^1H$ NMR and LC-MS; HPLC purity, >98.5%.

$^1$H-NMR, Lipid 20 (400 MHz, $CDCl_3$) δ=7.81-7.90 (2), 7.26-7.36 (2), 5.66 (m, 2), 5.52 (m, 2), 4.87 (m, 2), 4.59 (m, 2), 3.16-3.34 (4), 3.02 (t, J=7.0, 2), 2.64 (m, 2), 2.52 (t, J=7.0, 2), 2.27 (s, 6), 2.22-2.30 (2), 2.03-2.19 (4), 1.45-1.60 (6), 1.18-1.43 (26), 0.80-0.88 (6).

Example 17: In Vivo Mouse Factor VII Silencing

Using a liver-directed in vivo screen of the liposome libraries, a series of compounds may be tested for their ability to facilitate high levels of siRNA mediated gene silencing in hepatocytes, the cells comprising the liver parenchyma. Factor VII, a blood clotting factor, is a suitable target gene for assaying functional siRNA delivery to liver. Because this factor is produced specifically in hepatocytes, gene silencing indicates successful delivery to parenchyma, as opposed to delivery to the cells of the reticulo-endothelial system (e.g., Kupffer cells). Furthermore, Factor VII is a secreted protein that can be readily measured in serum, obviating the need to euthanize animals. Silencing at the mRNA level can be readily determined by measuring levels of protein. This is because the protein's short half-life (2-5 hour). C57BL/6 mice receive either saline or siRNA in liposome formulations via tail vein injection at a volume of 0.006 ml/g. At 48 h after administration, animals are anesthetized by isofluorane inhalation and blood is collected into serum separator tubes by retroorbital bleed. Serum levels of Factor VII protein are determined in samples using a chromogenic assay according to manufacturers' protocols. A standard curve is generated using serum collected from saline-treated animals.

What is claimed:
1. A compound of formula I

I wherein
X is a monocyclic, bicyclic, or tricyclic arene or heteroarene;
Y is an alkylene or an alkenylene, or a monocyclic, bicyclic, or tricyclic arene or heteroarene;
Z is S or O;
L is a linear or branched alkylene of 1 to 6 carbons;
$R_3$ and $R_4$ are independently a linear or branched alkyl of 1 to 6 carbons;
$R_1$ is a branched alkyl or alkenyl of 1 to 25 carbons;
$R_2$ is an alkyl or an alkenyl of 1 to 20 carbons;
r is 0 to 6;
m=0; and n, p, and q are independently 1 to 18;
or a pharmaceutically acceptable salt thereof.

2. The compound of claim 1, wherein $R_1$ is branched alkyl.

3. The compound of claim 2, wherein each branch of the branched alkyl consists of 4, 5, 6, 7, or 8 carbons.

4. The compound of claim 1, wherein $R_1$ is branched alkenyl.

5. The compound of claim 4, wherein each branch of the branched alkenyl consists of 7 carbons.

6. The compound of claim 1, wherein m+n<6, 5, 4, 3 or 2.

7. The compound of claim 1, wherein the arene or heteroarene is selected from the group consisting furan, benzofuran, isobenzofuran, pyrrole, indole, isoindole, thiophene, benzothiophene, imidazole, benzimidazole, purine, pyrazole, indazol, oxazole, benzoxazole, isoxazole, benzisoxazole, thiazole, isothiazole, benzothiazole, benzene, naphthalene, anthracene, pyridine, quinolone, isoquinoline, pyrazine, quinoxaline, acridine, pyrimidine, quinazoline, pyridazine, cinnoline phthalazin, 1,2,3-triazine, 1,2,4-triazine, and 1,3,5-triazine (s-triazine).

8. The compound of claim 4, wherein the arene or heteroarene comprises a substituent.

9. The compound of claim 8, wherein the substituent is selected from halo, alkyl, alkenyl, alkynyl, aryl, heterocyclyl, thiol, alkylthio, oxo, thioxy, alkylthioalkyl, alkyl sulfonyl, alkylsulfonylalkyl, alkoxy, aryloxy, aralkoxy, aminocarbonyl, alkylaminocarbonyl, alkoxycarbonyl, haloalkyl, amino, trifluoromethyl, cyano, nitro, alkylamino, alkylaminoalkyl, aminoalkylamino, hydroxy, alkoxyalkyl, carboxyalkyl, alkoxycarbonylalkyl, aminocarbonylalkyl, acyl, carboxylic acid, sulfonic acid, sulfonyl, and phosphonic acid.

10. The compound of claim 7, wherein the arene or heteroarene consists of benzene, naphthalene, or anthracene.

11. The compound of claim 1, wherein r=0.

12. The compound of claim 1, wherein Z=S.

13. The compound of claim 1, wherein L=$C_2$, $C_3$, $C_4$, $C_5$, or $C_6$ alkylene.

14. The compound of claim 1, wherein $R_3$ and $R_4$ are methyl, ethyl or propyl.

15. A compound of formula II or formula III (II)

(III)

wherein
Y is an alkylene or alkenylene;
Z is S or O;
L is a linear or branched alkylene of 2, 3, 4, 5 or 6 carbons;
$R_3$ and $R_4$ are independently a linear alkyl of 1, 2, 3, 4, 5, or 6 carbons;
$R_1$ is a branched alkyl of 1 to 24 carbons;
$R_2$ is a linear alkyl or alkenyl of 1 to 20 carbons;
r is 0 to 6;
m=0; and n, p, and q are independently 1 to 18;
or a pharmaceutically acceptable salt thereof.

16. The compound of claim 15, wherein n is 1, 2, 3 or 4.

17. The compound of claim 15, wherein $R_1$ is a branched alkyl of 3, 4, 5, 6, 7, 8, 9, 10, 11, 12, 13, 14, 15, 16, 17, 18, 19, 20, 21, 22, 23, or 24 carbons.

18. The compound of claim 17, wherein each branch of the branched alkyl is of the same length.

19. The compound of claim 16, wherein r=0 and Z=S.

20. A compound selected from the group consisting of lipids 17, 18, 19, and 20

17

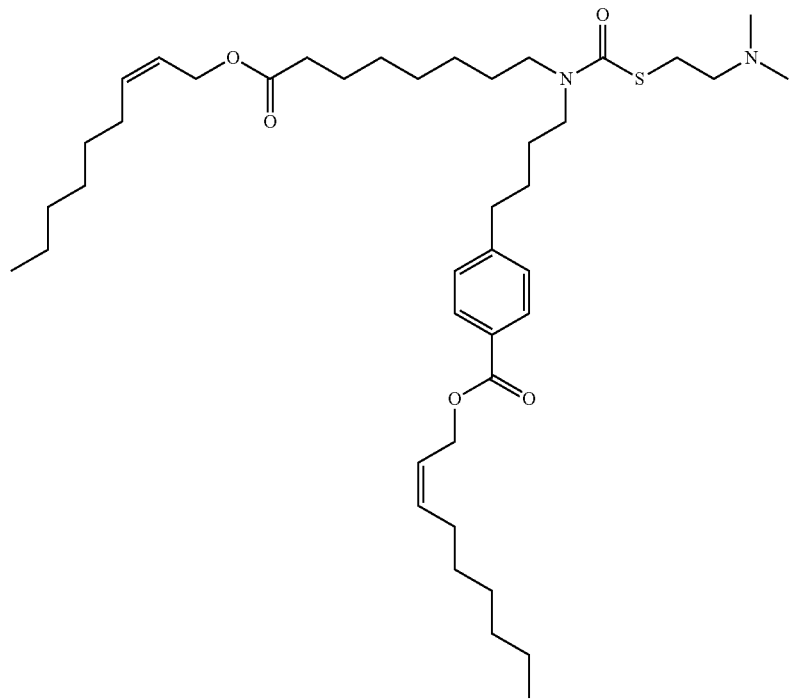
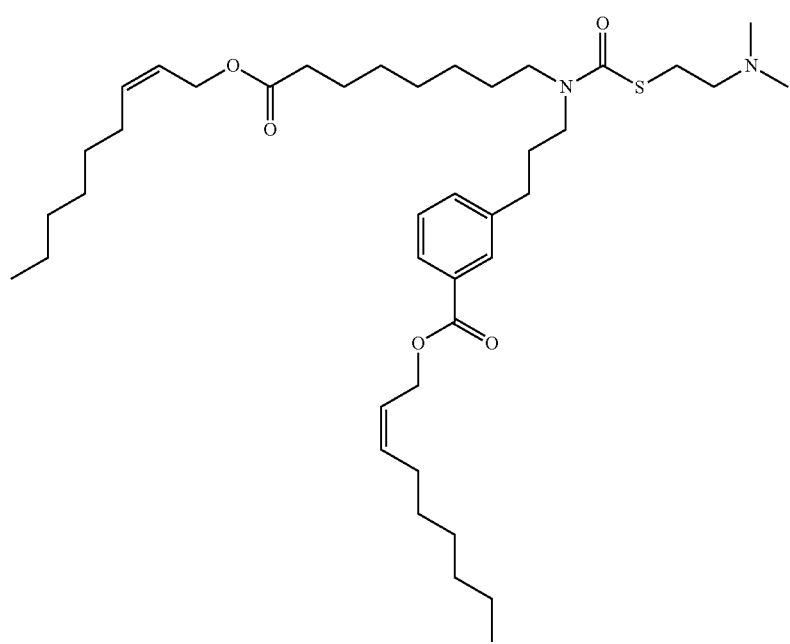

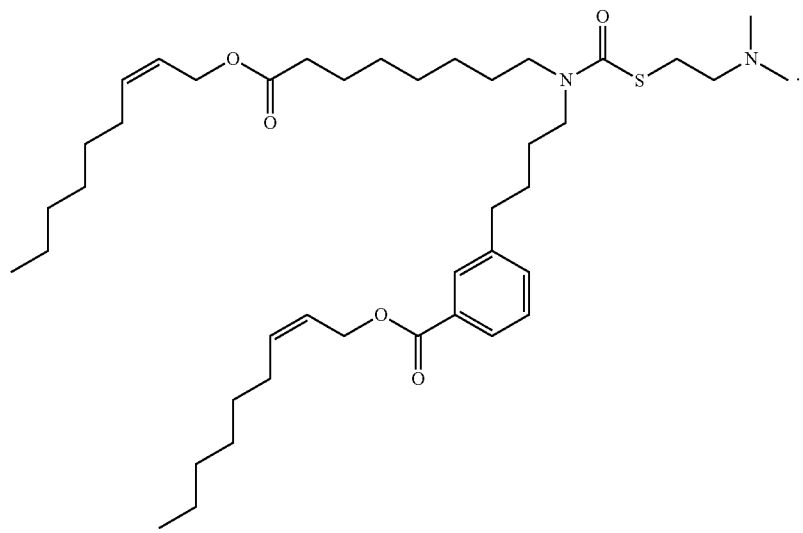
* * * * *